United States Patent
Iavarone et al.

(10) Patent No.: US 11,045,525 B2
(45) Date of Patent: Jun. 29, 2021

(54) COMPOSITIONS AND METHODS FOR REGULATING ACTIVITY OF INHIBITOR OF DNA BINDING-2 (ID2) PROTEIN AND FOR TREATING ID PROTEIN-RELATED DISEASES

(71) Applicant: THE TRUSTEES OF COLUMBIA UNIVERSITY IN THE CITY OF NEW YORK, New York, NY (US)

(72) Inventors: Antonio Iavarone, New York, NY (US); Anna Lasorella, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 176 days.

(21) Appl. No.: 16/025,668

(22) Filed: Jul. 2, 2018

(65) Prior Publication Data

US 2018/0303913 A1 Oct. 25, 2018

Related U.S. Application Data

(63) Continuation of application No. PCT/US2017/012352, filed on Feb. 5, 2017.

(60) Provisional application No. 62/274,871, filed on Jan. 5, 2016.

(51) Int. Cl.
| | |
|---|---|
| *A61K 38/45* | (2006.01) |
| *A61K 38/44* | (2006.01) |
| *A61P 35/00* | (2006.01) |

(52) U.S. Cl.
CPC .............. *A61K 38/45* (2013.01); *A61K 38/44* (2013.01); *A61P 35/00* (2018.01); *C12Y 114/11002* (2013.01); *C12Y 207/12001* (2013.01); *C12N 2510/00* (2013.01)

(58) Field of Classification Search
None
See application file for complete search history.

(56) References Cited

U.S. PATENT DOCUMENTS

| | | | | |
|---|---|---|---|---|
| 7,662,854 | B2 * | 2/2010 | Schofield ................... | A61P 3/00 514/557 |
| 7,811,595 | B2 * | 10/2010 | Kawamoto ........ | A61K 31/4418 424/401 |
| 8,778,904 | B2 * | 7/2014 | Feinstein ............. | A61K 31/713 514/44 A |
| 2002/0169117 | A1 * | 11/2002 | Maraskovsky ......... | A61P 29/00 435/69.1 |
| 2005/0208023 | A1 * | 9/2005 | Krissansen ........ | A61K 38/1709 424/93.2 |
| 2010/0004325 | A1 | 1/2010 | Yang et al. | |
| 2010/0240065 | A1 * | 9/2010 | Broadwater .... | C12Y 114/11002 435/7.1 |
| 2015/0292032 | A1 * | 10/2015 | Vilenchik ............... | A61P 25/00 514/19.3 |
| 2017/0296541 | A1 * | 10/2017 | Vilenchik ............ | A61K 31/519 |

FOREIGN PATENT DOCUMENTS

| | | |
|---|---|---|
| WO | WO 02/074981 A2 | 9/2002 |
| WO | WO 2007/005504 A2 | 1/2007 |

OTHER PUBLICATIONS

Lasorella et al., The ID proteins: master regulators of cancer stem cells and tumour aggressiveness, Nature Reviews, Cancer, vol. 14, Feb. 2014 (Year: 2014).*
Zelm, (ID2 (Inhibitor of DNA Binding 2, Dominant Negative Helix-Loop-Helix Protein), Atlas of Genetics and Cytogenetics in Oncology and Haematology, Webpage, Jun. 2014 (Year: 2014).*
Miyazaki et al., Id2 and Id3 maintain the regulatory T cell pool to suppress inflammatory disease, Nat Immunol. Aug. 2014; 15(8): 767-776 (Year: 2014).*
Havrda et al., Behavioral abnormalities and Parkinson's-like histological changes resulting from Id2 inactivation in mice, Disease Models & Mechanisms 6, 819-827 (2013) (Year: 2013).*
Subhani et al., HIF inhibitors for ischemic retinopathies and cancers: options beyond anti-VEGF therapies, Angiogenesis (2016) 19: 257-273 (Year: 2016).*
Burroughs et al., Hypoxia inducible factor pathway inhibitors as anticancer therapeutics, Future Med Chem. Apr. 2013 ; 5(5) (Year: 2013).*
Pozo et al., Inhibition of DYRK1A destabilizes EGFRand reduces EGFR dependent glioblastoma growth, J Clin Invest. 2013; 123(6):2475-2487 (Year: 2013).*
Fernandez-Martinez et al., DYRK1A: the double-edged kinase as a protagonist in cell growth and tumorigenesis, Molecular & Cellular Oncology, 2:1, e970048, 2015 (Year: 2015).*
Fong et al., Id genes and proteins as promising targets in cancer therapy, TRENDS in Molecular Medicine vol. 10 No. 8 Aug. 8, 2004 (Year: 2004).*

(Continued)

*Primary Examiner* — Louise W Humphrey
*Assistant Examiner* — Srikanth Patury
(74) *Attorney, Agent, or Firm* — Baker Botts, L.L.P.

(57) ABSTRACT

The present disclosure provides, in one embodiment, a method of treating or preventing an ID2 protein-related disease in a patient at risk of developing or having such a disease by administering to the patient a composition in an amount and for a time sufficient to increase degradation of HIFα in a cell affected by the ID2 protein-related disease in the patent and/or to decrease half-life of HIFα in the cell affected by the ID2 protein-related disease in the patient, as compared to an untreated cell affected by the ID2 protein-related disease.

8 Claims, 34 Drawing Sheets
Specification includes a Sequence Listing.

(56) References Cited

OTHER PUBLICATIONS

Albertoni et al., "Anoxia induces macrophage inhibitory cytokine-1 (MIC-1) in glioblastoma cells independently of p53 and HIF-1," Oncogene 21:4212-4219 (2002).
Bayin et al., "GPR133 (ADGRD1), an adhesion G-protein-coupled receptor, is necessary for glioblastoma growth," Oncogenesis 5:e263 (2016).
Benezra et al., "Induction of Complete Regressions of Oncogene-induced Breast Tumors in Mice," Cold Spring Harbor Symposia on Quantitative Biology 70:375-381 (2005).
Fong et al., "ID genes and proteins as promising targets in cancer therapy," Trends in Molecular Medicine 10(8):387-392 (2004).
Sanchez Gomez et al., "DYRK1a Modulates the Self-renewal Capacity of Neural Stem Cells and Tumor Initiating Cells: Targetting the Achilles Heels of EGFR Addicted Glioblastomas," European Journal of Cancer 48(Suppl. 5):S60 (2012).
Subhani et al., "HIF inhibitors for ischemic retinopathies and cancers: options beyond anti-VEGF therapies," Angiogenesis 19:257-273 (2016).
Supplementary European Search Report dated Aug. 20, 2019 in Application No. EP17736345.
Abagyan, Ruben, and Maxim Totrov. "Biased probability Monte Carlo conformational searches and electrostatic calculations for peptides and proteins." *Journal of molecular biology* 235.3 (1994): 983-1002; 21 pages.
Almond, David, and Timothy Cardozo. "Assessment of immunologically relevant dynamic tertiary structural features of the HIV-1 V3 loop crown R2 sequence by ab initio folding." *Journal of visualized experiments: JoVE* 43 (2010); 3 pages.
Alvarez. Mariano J., Federico Giorgi, and Andrea Califano. "Using viper, a package for Virtual Inference of Protein-activity by Enriched Regulon analysis." *Bioconductor* (2014): 1-14; 15 pages.
Aranda, Sergi, Ariadna Laguna, and Susana de la Luna. "DYRK family of protein kinases: evolutionary relationships, biochemical properties, and functional roles." *The FASEB Journal* 25.2 (2011): 449-462; 14 pages.
Becker, Walter. "Emerging role of DYRK family protein kinases as regulators of protein stability in cell cycle control." *Cell Cycle* 11.18 (2012): 3389-3391; 14 pages.
Bordner, Andrew J., and Ruben Abagyan. "Ab initio prediction of peptide-MHC binding geometry for diverse class I MHC allotypes." *Proteins: Structure Function, and Bioinformatics* 63.3 (2006): 512-526; 15 pages.
Carro, Maria Stella, et al. "The transcriptional network for mesenchymal transformation of brain tumours." *Nature* 463.7279 (2010): 318; 24 pages.
Cawthorne, Christopher, et al. "Comparison of doxycycline delivery methods for Tet-inducible gene expression in a subcutaneous xenograft model." *Journal of biomolecular techniques: JBT* 18.2 (2007): 120; 4 pages.
Chakrabarti, Lina, Zvgmunt Galdzicki, and Tarik F. Haydar. "Defects in embryonic neurogenesis and initial synapse formation in the forebrain of the Ts65Dn mouse model of Down syndrome." *Journal of Neuroscience* 27.43 (2007): 11483-11495; 13 pages.
Chamboredon, Sandrine, et al. "Hypoxia-inducible factor-1α mRNA: a new target for destabilization by tristetraprolin in endothelial cells." *Molecular biology of the cell* 22.18 (2011): 3366-3378; 13 pages.
Contestabile, Andrea, et al. "Cell cycle alteration and decreased cell proliferation in the hippocampal dentate gyrus and in the neocortical germinal matrix of fetuses with Down syndrome and in Ts65Dn mice." *Hippocampus* 17.8 (2007): 665-678 (Abstract); 1 page.
Deleyrolle, Loic P., et al. "Determination of somatic and cancer stem cell self-renewing symmetric division rate using sphere assays." *PloS one* 6.1 (2011): e15844; 11 pages.
Giorgi, Federico M., et al. "Inferring protein modulation from gene expression data using conditional mutual information." *PloS one* 9.10 (2014): e109569; 9 pages.

Göckler, Nora, et al. "Harmine specifically inhibits protein kinase DYRK1A and interferes with neurite formation," *The FEBS journal* 276.21 (2009): 6324-6337; 14 pages.
Gordan, John D., et al. "HIF-2α promotes hypoxic cell proliferation by enhancing c-myc transcriptional activity." *Cancer cell* 11.4 (2007): 335-347; 13 pages.
Guimerd, Jordi, et al. "A human homologue of *Drosophila* minibrain (MNB) is expressed in the neuronal regions affected in Down syndrome and maps to the critical region." *Human molecular genetics* 5.9 (1996): 1305-1310; 6 pages.
Hämmerle, Barbara, et al. "Transient expression of Mnb/Dyrk1a couples cell cycle exit and differentiation of neuronal precursors by inducing p27KIP1 expression and suppressing NOTCH signaling." *Development* 138.12 (2011): 2543-2554; 12 pages.
Hara, Eiji, Marcia Hall, and Gordon Peters. "Cdk2-dependent phosphorylation of Id2 modulates activity of E2A-related transcription factors." *The EMBO journal* 16.2 (1997): 332-342; 11 pages.
Hibaoui, Youssef, et al. "Modelling and rescuing neurodevelopmental defect of Down syndrome using induced pluripotent stem cells from monozygotic twins discordant for trisomy 21." *EMBO molecular medicine* (2013); 19 pages.
Himpel, Sunke, et al. "Identification of the autophosphorylation sites and characterization of their effects in the protein kinase DYRK1A." *Biochemical Journal* 359.3 (2001): 497-505; 9 apges.
Himpel, Sunke, et al. "Specificity determinants of substrate recognition by the protein kinase DYRK1A." *Journal of Biological Chemistry* 275.4 (2000): 2431-2438; 9 pages.
International Search Report and Written Opinion for PCT Patent Application No. PCT/US17/12352, dated Apr. 28, 2017; 11 pages.
Kaelin Jr, William G., and Peter J. Ratcliffe. "Oxygen sensing by metazoans: the central role of the HIF hydroxylase pathway." *Molecular cell* 30.4 (2008): 393-402; 10 pages.
Kamura. T., et al. "Rbx1, a component of the VHL tumor suppressor complex and SCF ubiquitin ligase." *Science* 284.5414 (1999): 657-661; 6 pages.
Keith, Brian, Randall S. Johnson, and M. Celeste Simon. "HIF1α and HIF2α: sibling rivalry in hypoxic tumour growth and progression." *Nature Reviews Cancer* 12.1 (2012); 28 pages.
Kershaw, Nadia J., and Jeffrey J. Babon. "VHL: cullin-g the hypoxic response." *Structure* 23.3 (2015): 435-436; 2 pages.
Kondo, Keiichi, et al. "Inhibition of HIF2α is sufficient to suppress pVHL-defective tumor growth." *PLoS biology* 1.3 (2003); 6 pages.
Lasorella, Anna, et al. "Id2 mediates tumor initiation, proliferation, and angiogenesis in Rb mutant mice." *Molecular and cellular biology* 25.9 (2005): 3563-3574; 12 pages.
Lasorella, Anna, Robert Benezra, and Antonio Iavarone. "The ID proteins: master regulators of cancer stem cells and tumour aggressiveness." *Nature Reviews Cancer* 14.2 (2014); 2 pages.
Lauth, Matthias, et al. "DYRK1B-dependent autocrine-to-paracrine shift of Hedgehog signaling by mutant RAS." *Nature structural & molecular biology* 17.6 (2010); 9 pages.
Lee, Kangmoon, Xiaobing Deng, and Eileen Friedman. "Mirk protein kinase is a mitogen-activated protein kinase substrate that mediates survival of colon cancer cells." *Cancer research* 60.13 (2000): 3631-3637; 8 pages.
Li, Zhizhong, et al. "Hypoxia-inducible factors regulate tumorigenic capacity of glioma stem cells." *Cancer cell* 15.6 (2009): 501-513; 13 pages.
Litovchick, Larisa, et al. "DYRK1A protein kinase promotes quiescence and senescence through DREAM complex assembly." *Genes & development* 25.8 (2011): 801-813; 14 pages.
Löfstedt, Tobias, et al. "Induction of ID2 expression by hypoxia-inducible factor-1: A Role in dedifferentiation of hypoxic neuroblastoma cells." *Journal of Biological Chemistry* (2004); 39 pages.
Mao, Junhao, et al. "Regulation of Gli1 transcriptional activity in the nucleus by Dyrk1." *Journal of Biological Chemistry* (2002); 28 pages.
Miinea, Cristinel P., and Gustav E. Lienhard. "Stoichiometry of site-specific protein phosphorylation estimated with phosphopeptide-specific antibodies." *Biotechniques* 34.4 (2003): 828-831; 11 pages.
Nam, Hyung-song, and Robert Benezra. "High levels of Id1 expression define B1 type adult neural stem cells." *Cell stem cell* 5.5 (2009): 515-526; 12 pages.

(56) References Cited

OTHER PUBLICATIONS

Nguyen, Henry C., et al. "Insights into Cullin-RING E3 ubiquitin ligase recruitment: structure of the VHL-EloBC-Cul2 complex." *Structure* 23.3 (2015): 441-449; 10 pages.

Niola, Francesco, et al. "Id proteins synchronize stemness and anchorage to the niche of neural stein cells." *Nature cell biology* 14.5 (2012); 28 pages.

Niola, Francesco, et al. "Mesenchymal high-grade glioma is maintained by the ID-RAP1 axis." *The Journal of clinical investigation* 123.1 (2013): 405-417; 13 pages.

Ohta, Tomohiko, et al. "ROC1, a homolog of APC11, represents a family of cullin partners with an associated ubiquitin ligase activity." *Molecular cell* 3.4 (1999): 535-541; 7 pages.

Park, Joongkyu, et al. "Dyrk1A phosphorylates p53 and inhibits proliferation of embryonic neuronal cells," *Journal of Biological Chemistry* (2010); 23 pages.

Perk, Jonathan, Antonio Iavarone, and Robert Benezra., "Id family of helix-loop-helix proteins in cancer," *Nature Reviews Cancer* 5.8 (2005); 12 pages.

Pietras, Alexander, et al. "HIF-2α maintains an undifferentiated state in neural crest-like human neuroblastoma tumor-initiating cells." *Proceedings of the National Academy of Sciences* 106.39 (2009): 16805-16810; 6 pages.

Pozo, Natividad, et al. "Inhibition of DYRK1A destabilizes EGFR and reduces EGFR-dependent glioblastoma growth." *The Journal of clinical investigation* 123.6 (2013): 2475-2487; 13 pages.

Reynolds, Brent A., and Samuel Weiss. "Clonal and population analyses demonstrate that an EGF-responsive mammalian embryonic CNS precursor is a stem cell." *Developmental biology* 175.1 (1996); 13 pages.

Semenza, Gregg L. "HIF-1, O2, and the 3 PHDs: how animal cells signal hypoxia to the nucleus." *Cell* 107.1 (2001); 3 pages.

Sullivan, Jaclyn M., et al. "Phosphorylation regulates Id2 degradation and mediates the proliferation of neural precursor cells," *Stem Cells* 34.5 (2016): 1321-1331; 26 pages.

Tropepe, Vincent, et al. "Distinct neural stein cells proliferate in response to EGF and FGF in the developing mouse telencephalon." *Developmental biology* 208.1 (1999); 23 pages.

Vandeputte, Dmitri AA, et al. "Expression and distribution of id helix-loop-helix proteins in human astrocytic tumors." *Glia* 38.4 (2002), (Abstract only); 1 page.

Wang, Kai, et al. "Genome-wide identification of post-translational modulators of transcription factor activity in human B cells." *Nature biotechnology* 27.9 (2009); 28 pages.

Warnecke, C. et al. Differentiating the functional role of hypoxia-inducible factor (HIF)-1α and HIF-2α (EPAS-1) by the use of RNA interference: erythropoietin is a HIF-2α target gene in Hcp3B and Kelly cells. FASEB J. 18, 1462-1464 (2004); 3 pages.

Yabut, Odessa, Jason Domogauer, and Gabriellla D'Arcangelo. "Dyrk1A overexpression inhibits proliferation and induces premature neuronal differenctiation of neural progenitor cells," *Journal of Neuroscience* 30.11 (2011); 11 pages.

Eskilsson et al., "EGFR heterogeneity and implications for therapeutic intervention in glioblastoma", (2018) Neuro-Oncology 20:743-752, advance access date Oct. 10, 2017.

Westphal et al., "EGFR as a Target for Glioblastoma Treatment: An Unfulfilled Promise", (2017) CNS Drugs 31:723-735, Published online: Aug. 8, 2017.

Szerlip et al., "Intratumoral heterogeneity of receptor tyrosine kinases EGFR and PDGFRA amplification in glioblastoma defines subpopulations with distinct growth factor response", (2011) PNAS 109:3041-3046.

\* cited by examiner

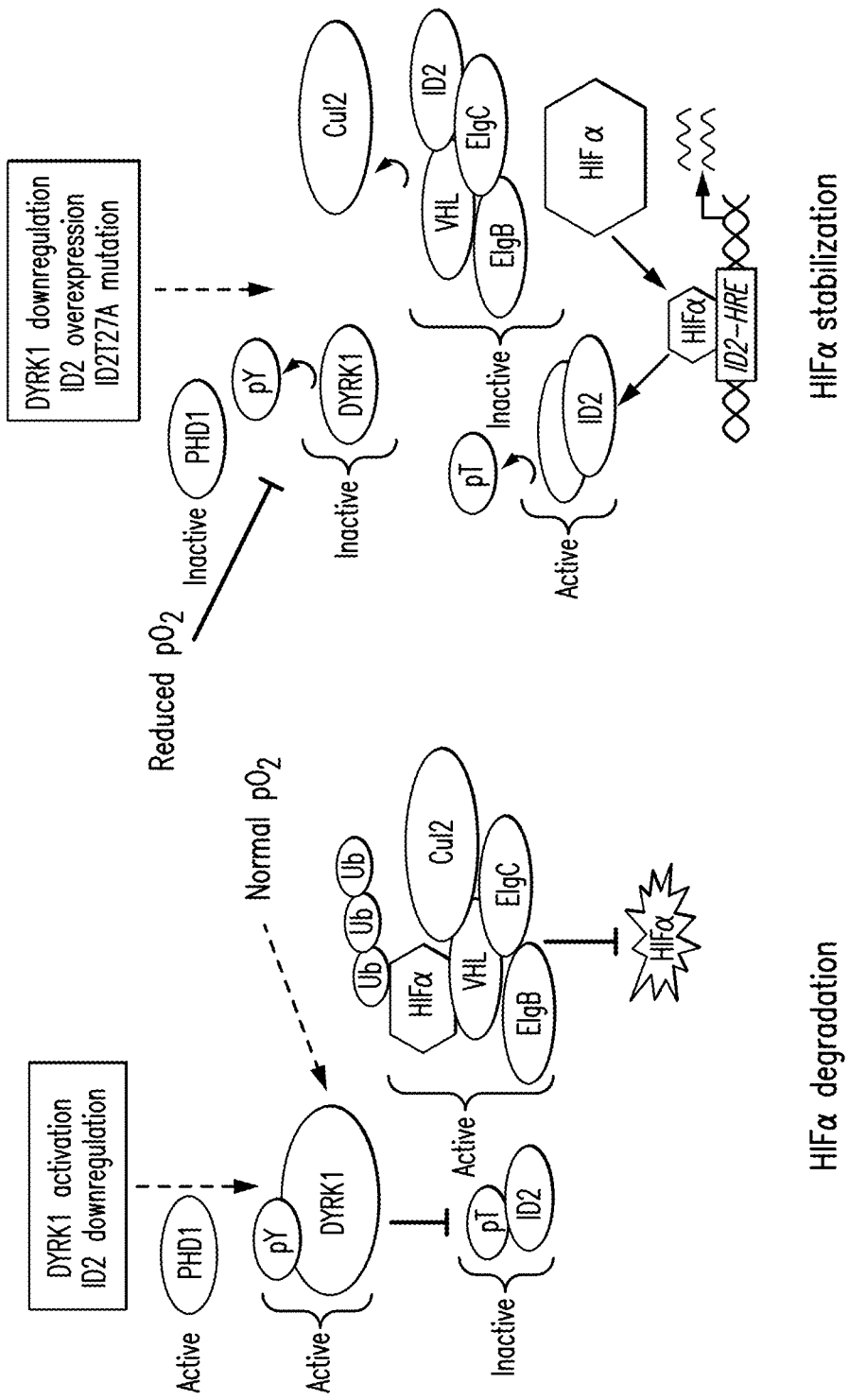

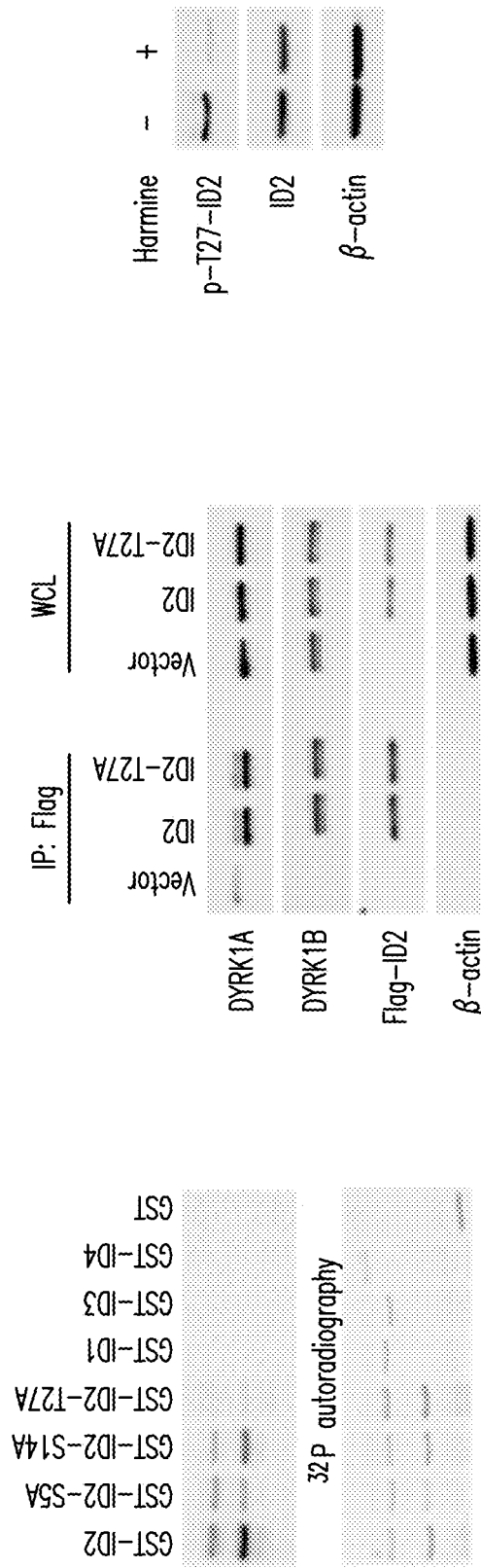

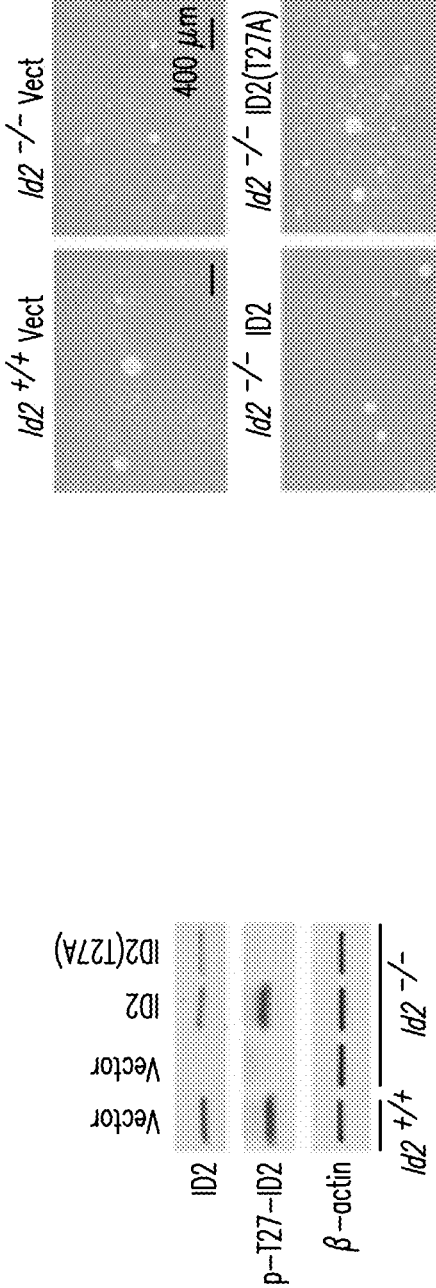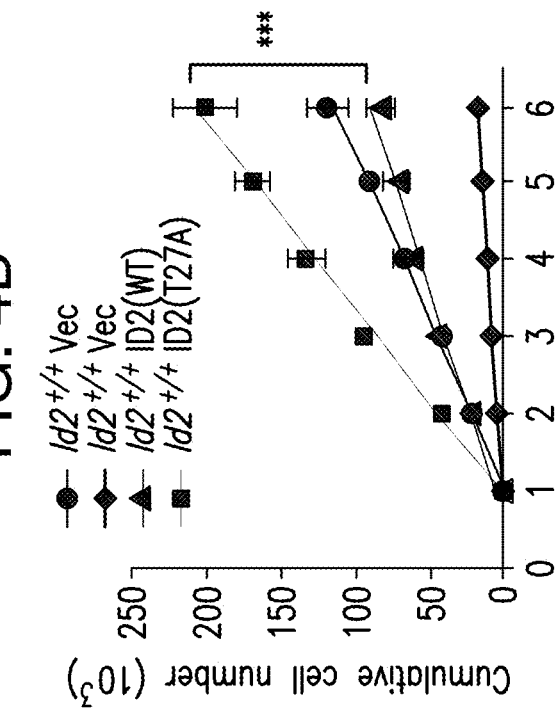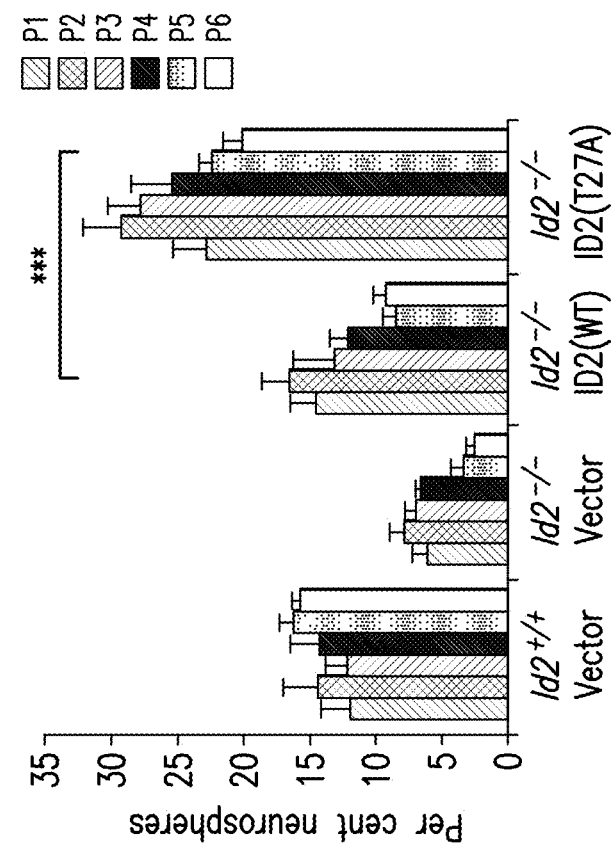
FIG. 4A
FIG. 4B
FIG. 4C
FIG. 4D

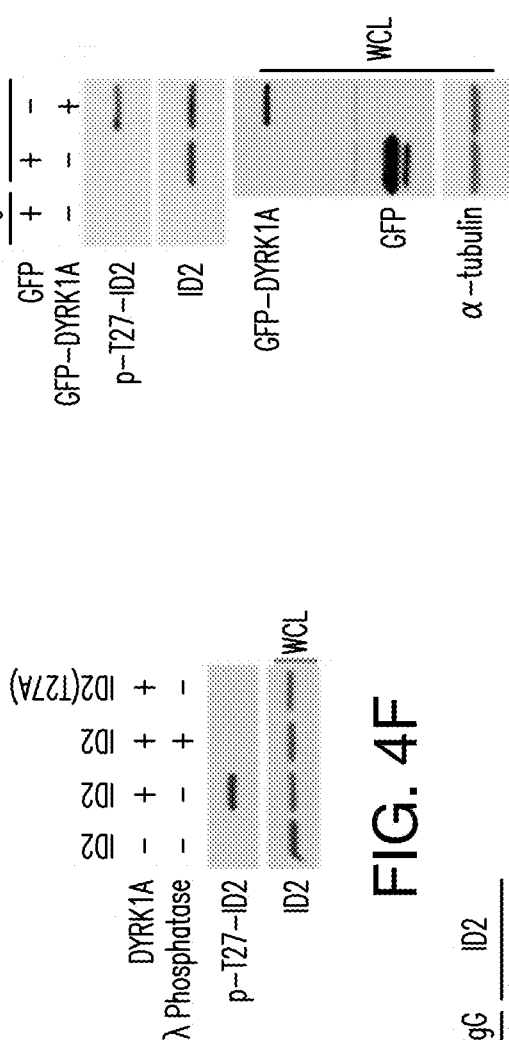
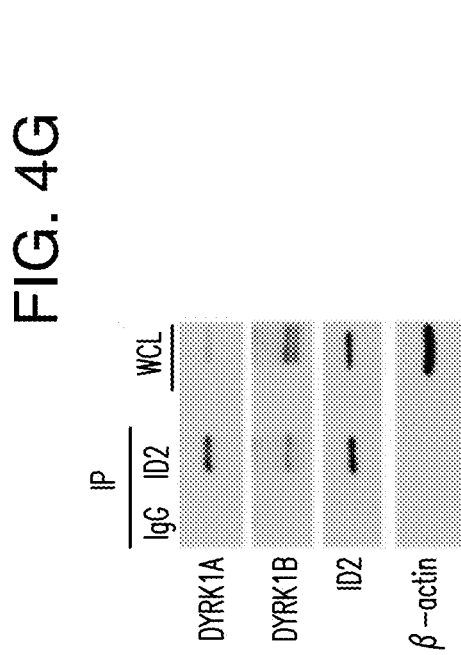
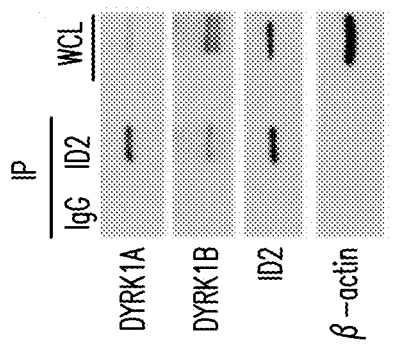
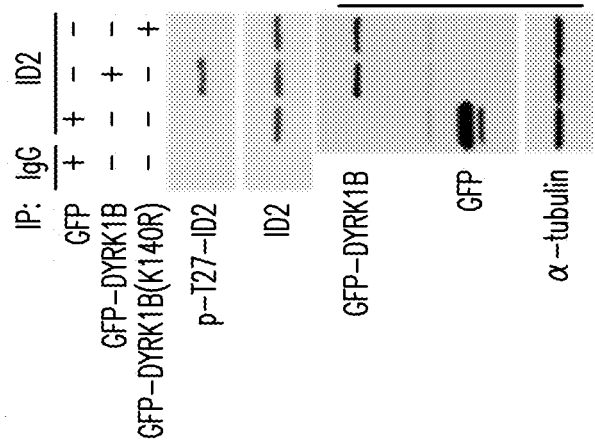
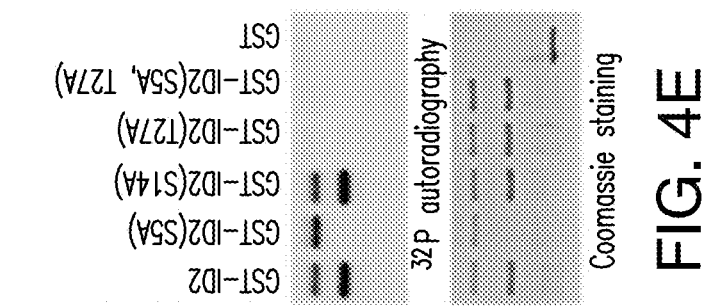

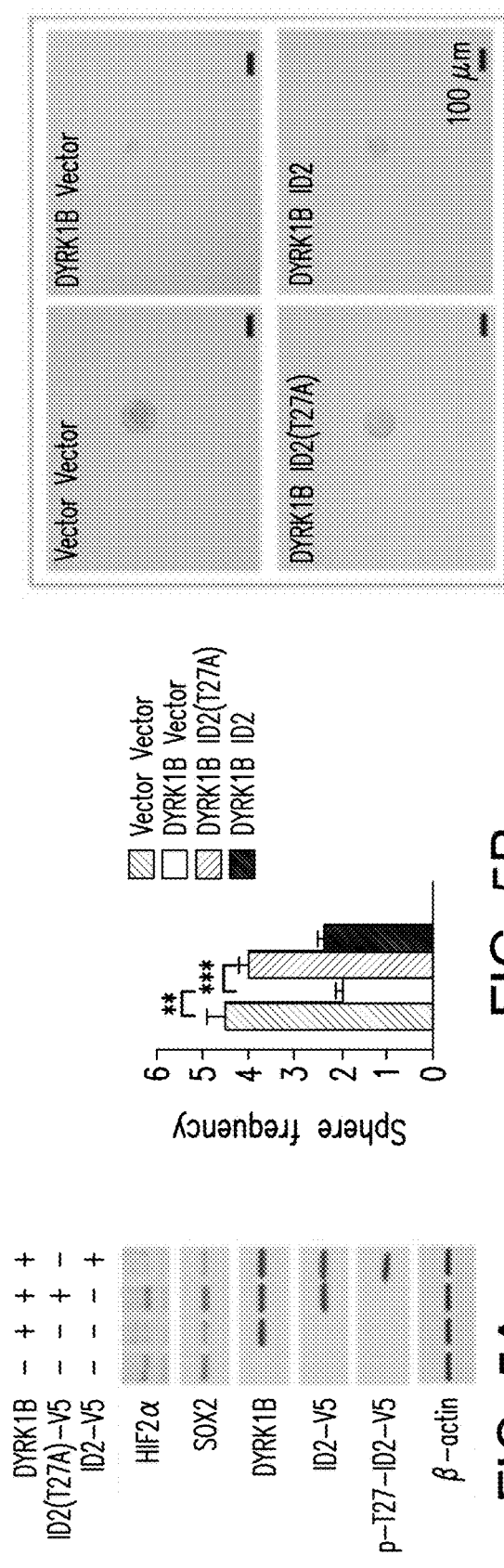
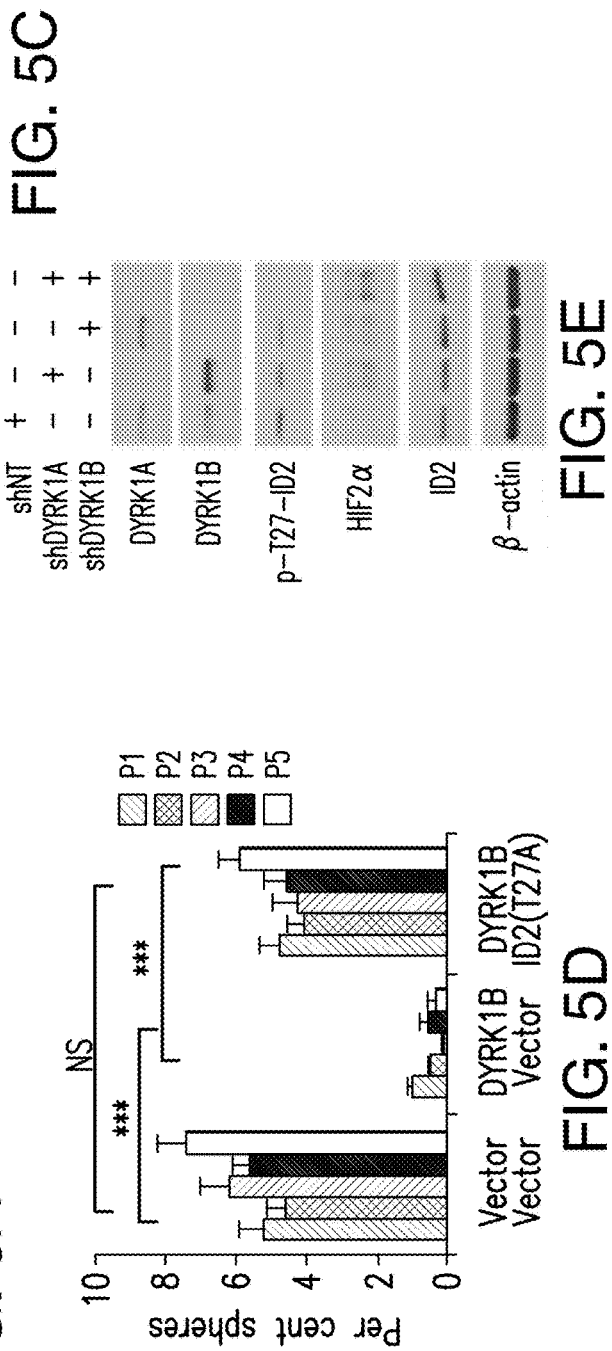

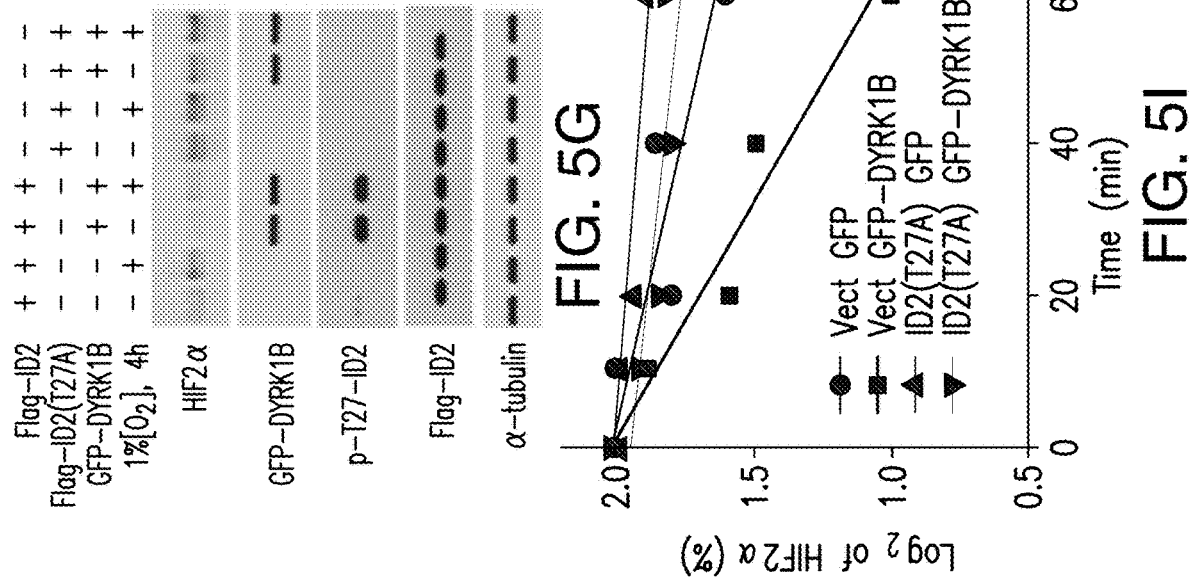
FIG. 5G
FIG. 5I
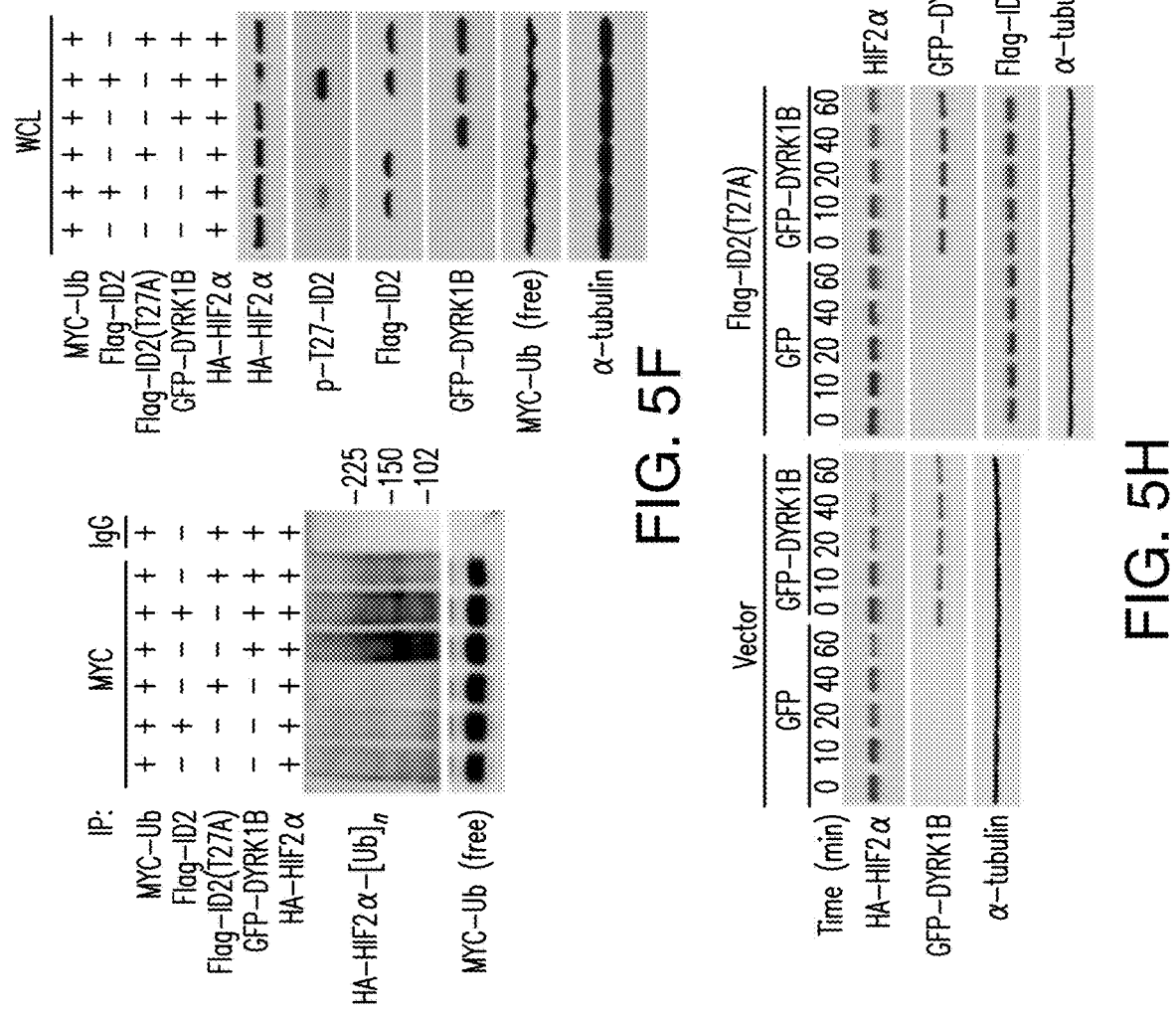
FIG. 5F
FIG. 5H

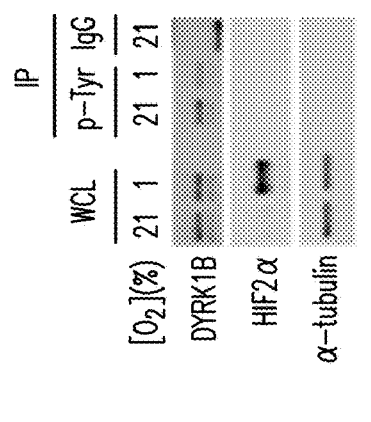
FIG. 6A
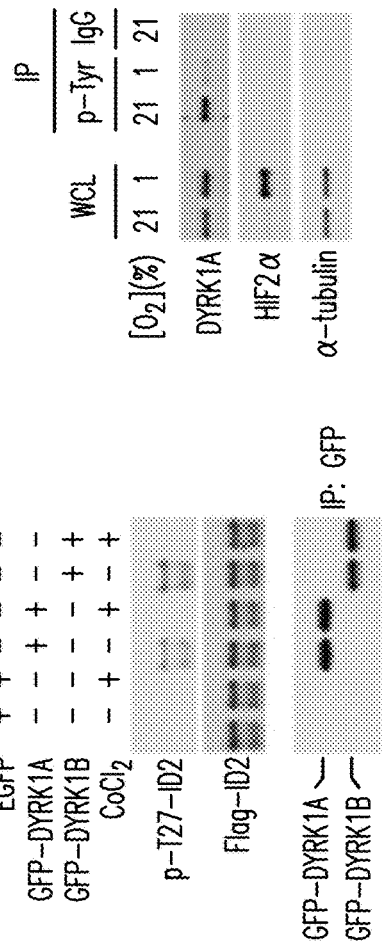
FIG. 6B
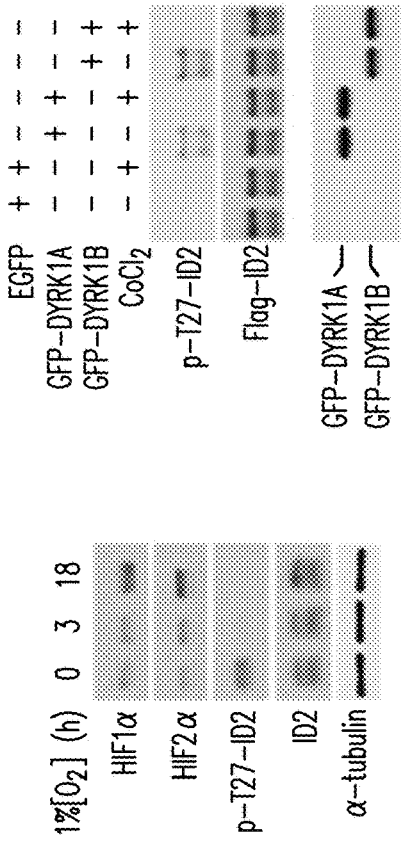
FIG. 6C
FIG. 6D
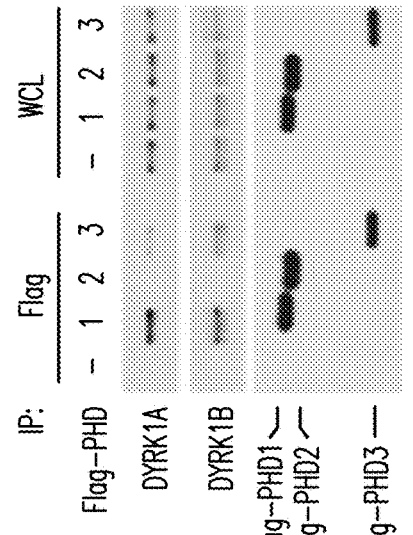
FIG. 6E
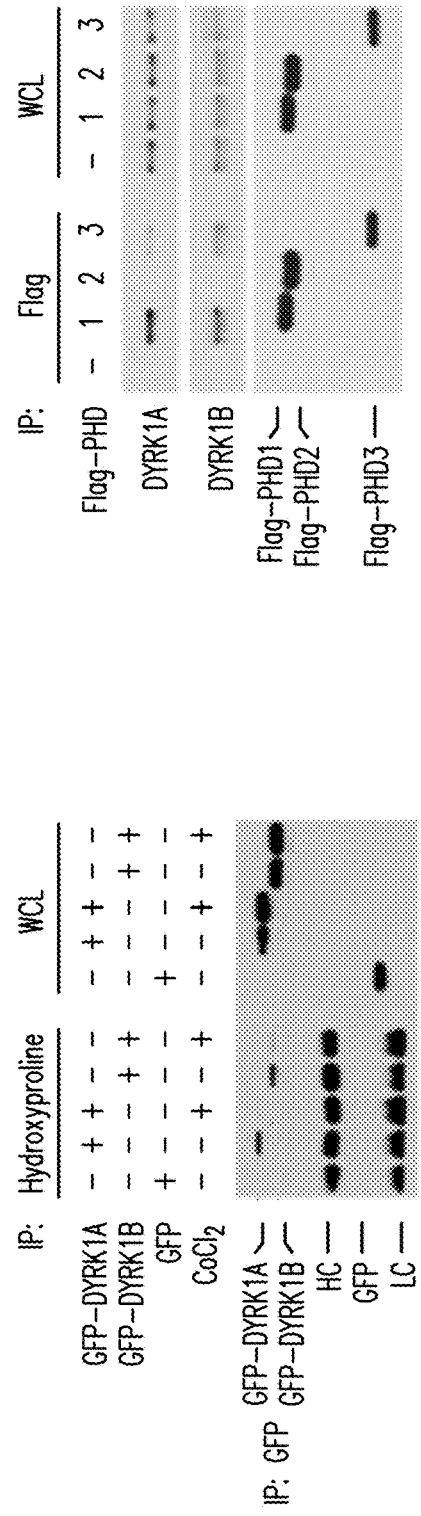
FIG. 6F

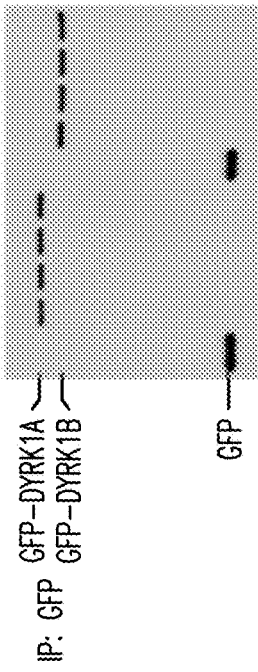
FIG. 6G
FIG. 6H
FIG. 6I

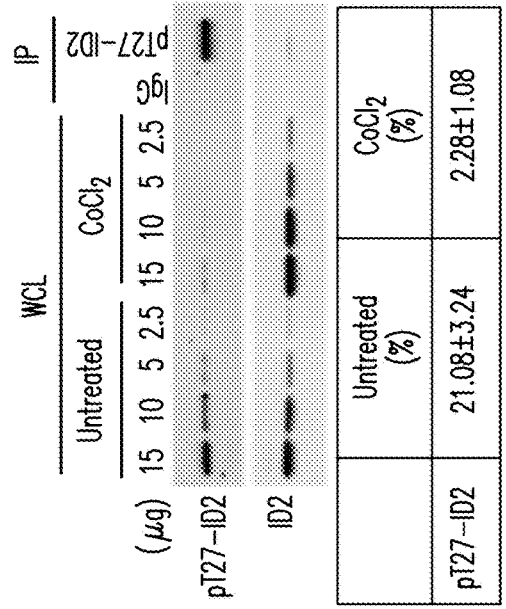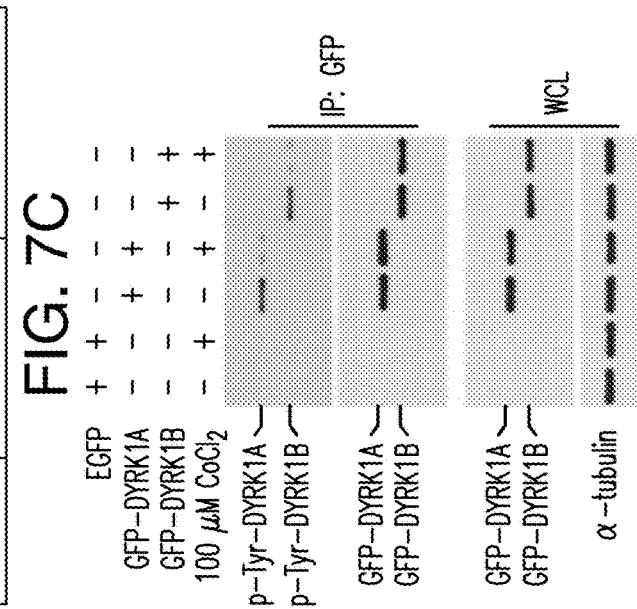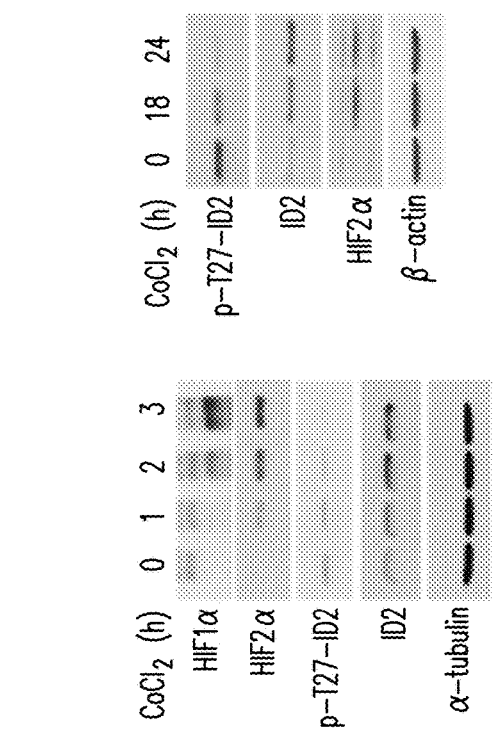
FIG. 7A
FIG. 7B
FIG. 7C
FIG. 7D
FIG. 7E

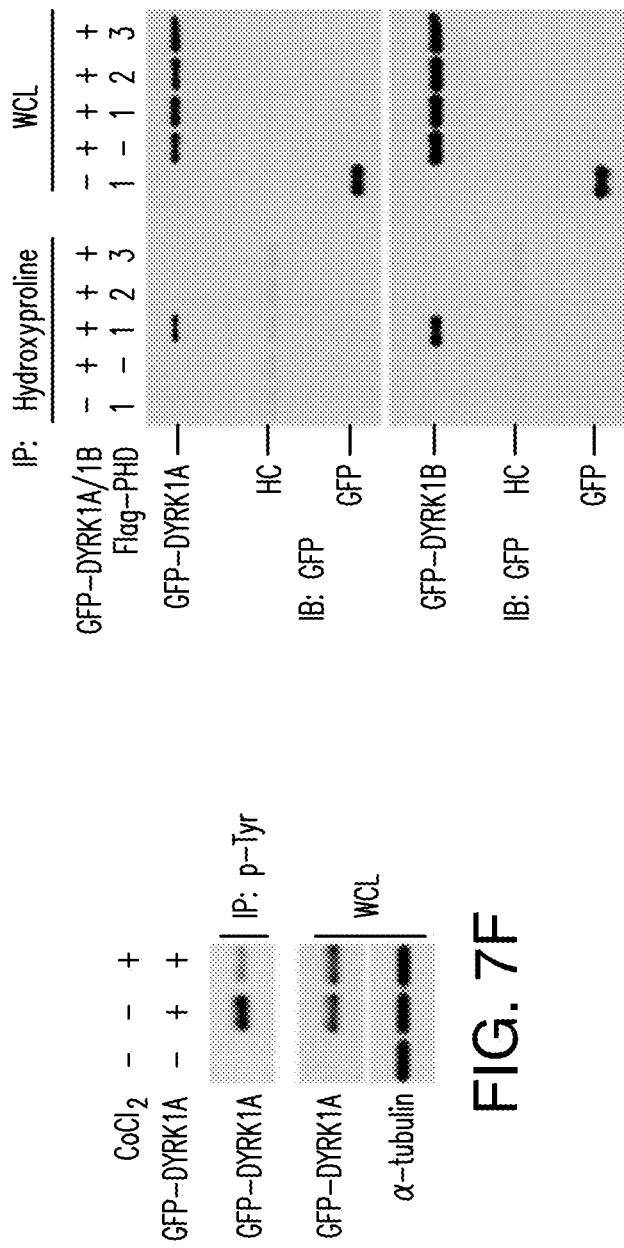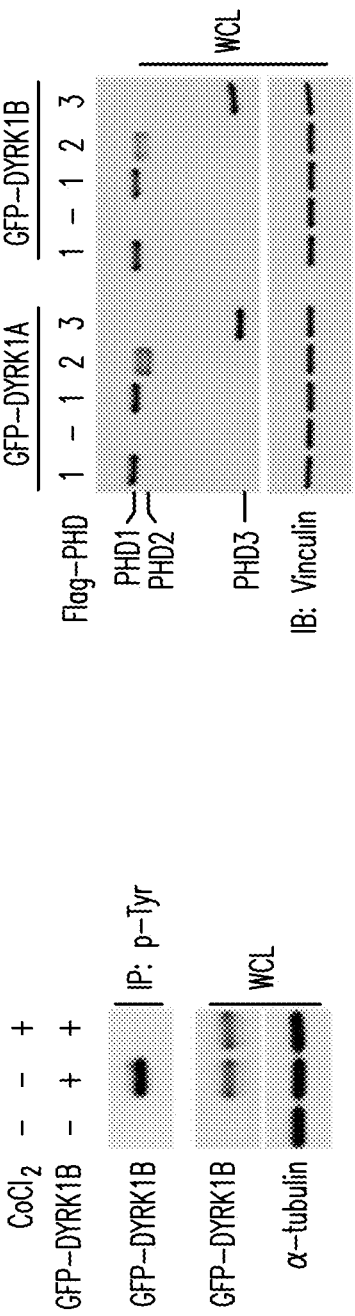
FIG. 7F  FIG. 7G  FIG. 7H

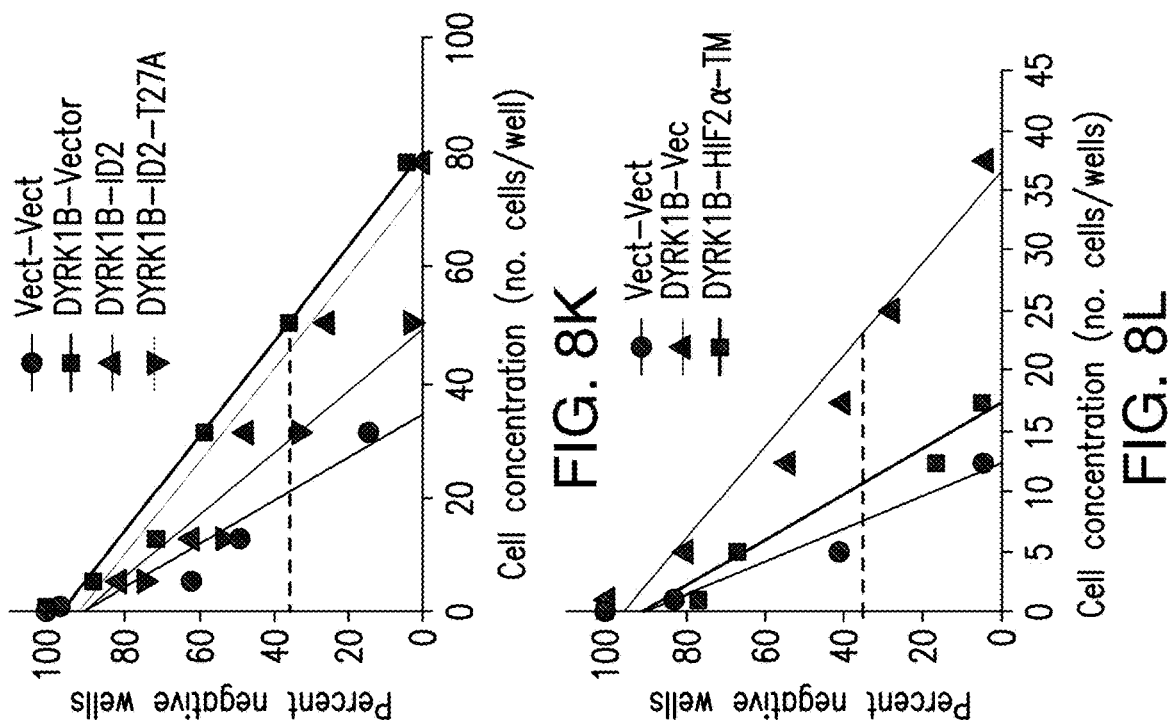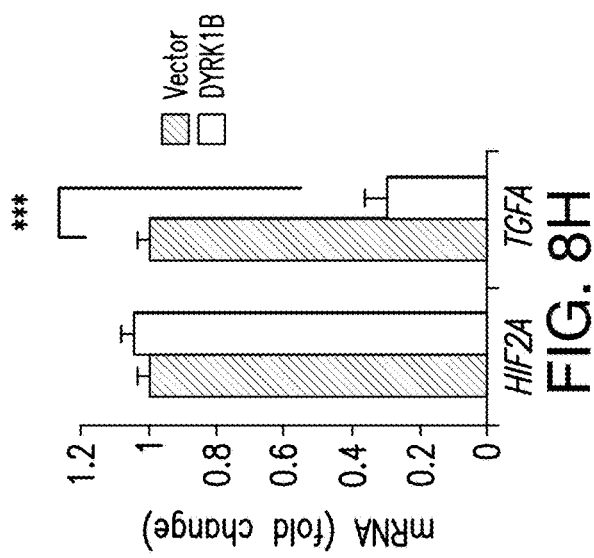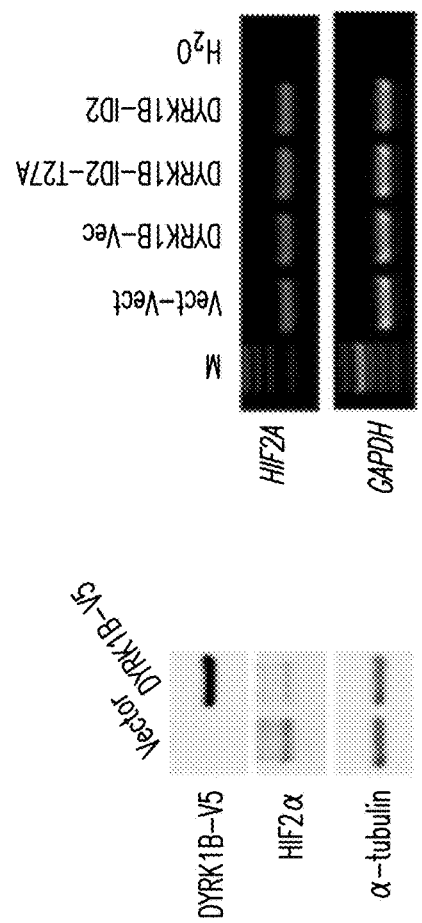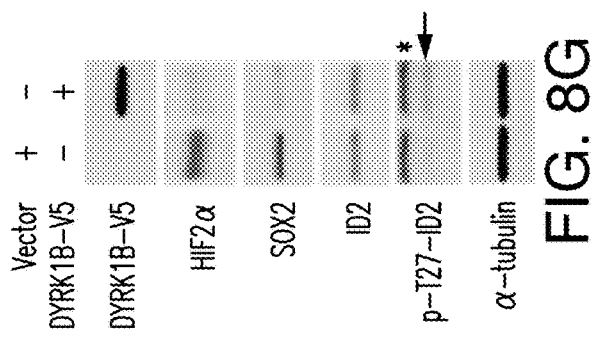

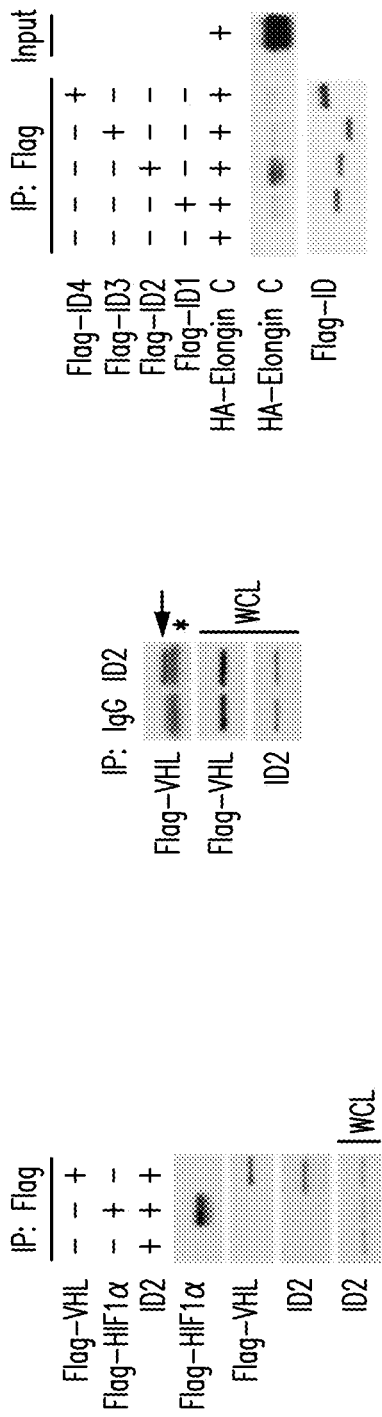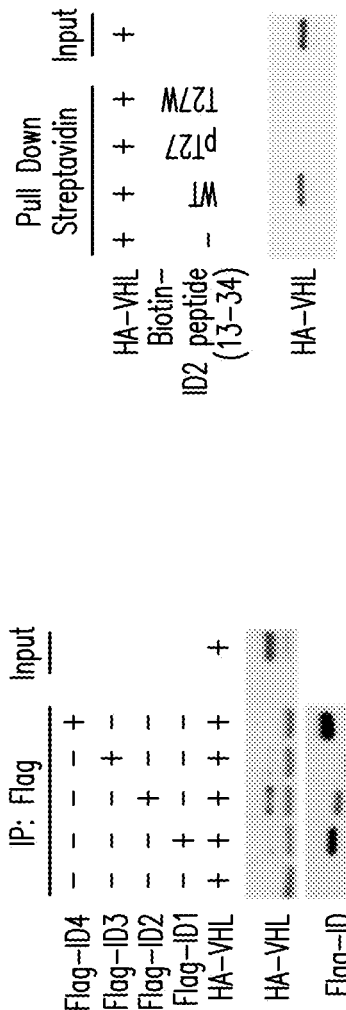
FIG. 9D  FIG. 9E  FIG. 9F  FIG. 9G  FIG. 9H

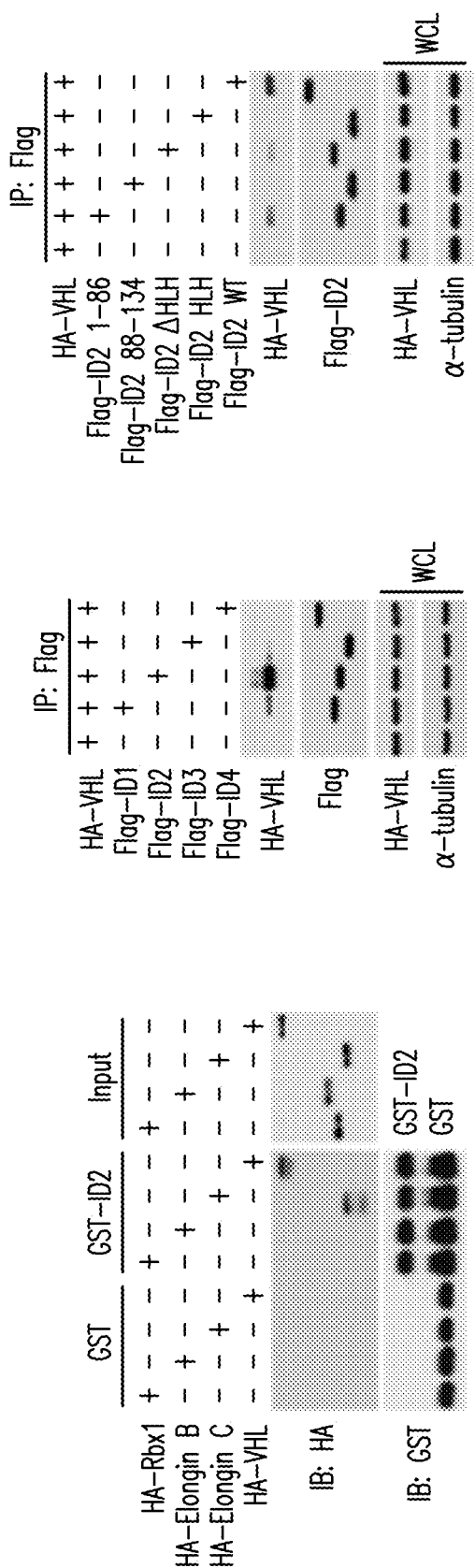
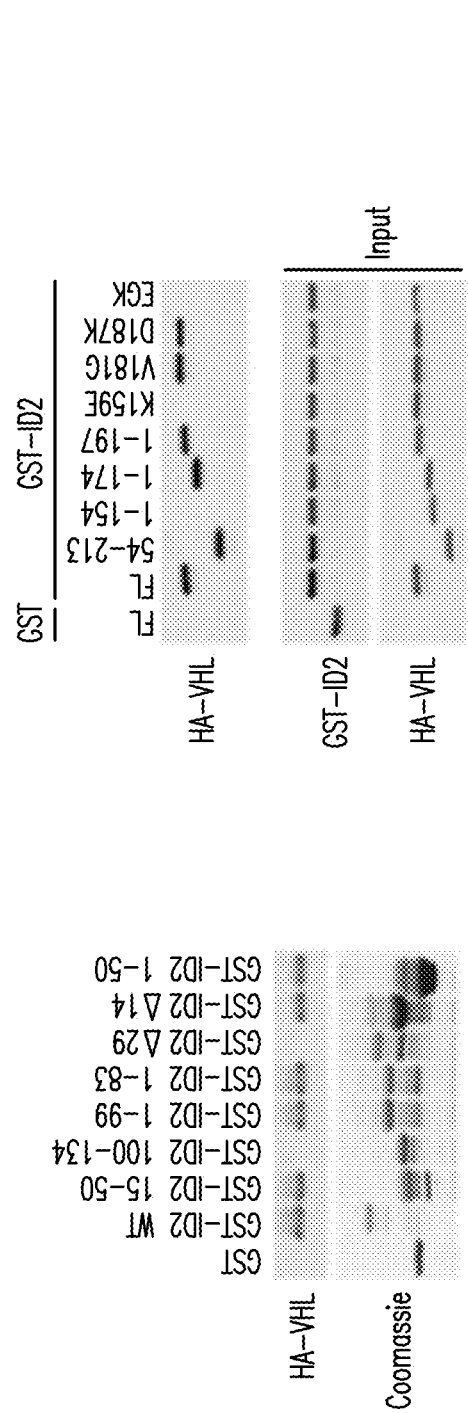
FIG. 10A
FIG. 10B
FIG. 10C
FIG. 10D
FIG. 10E

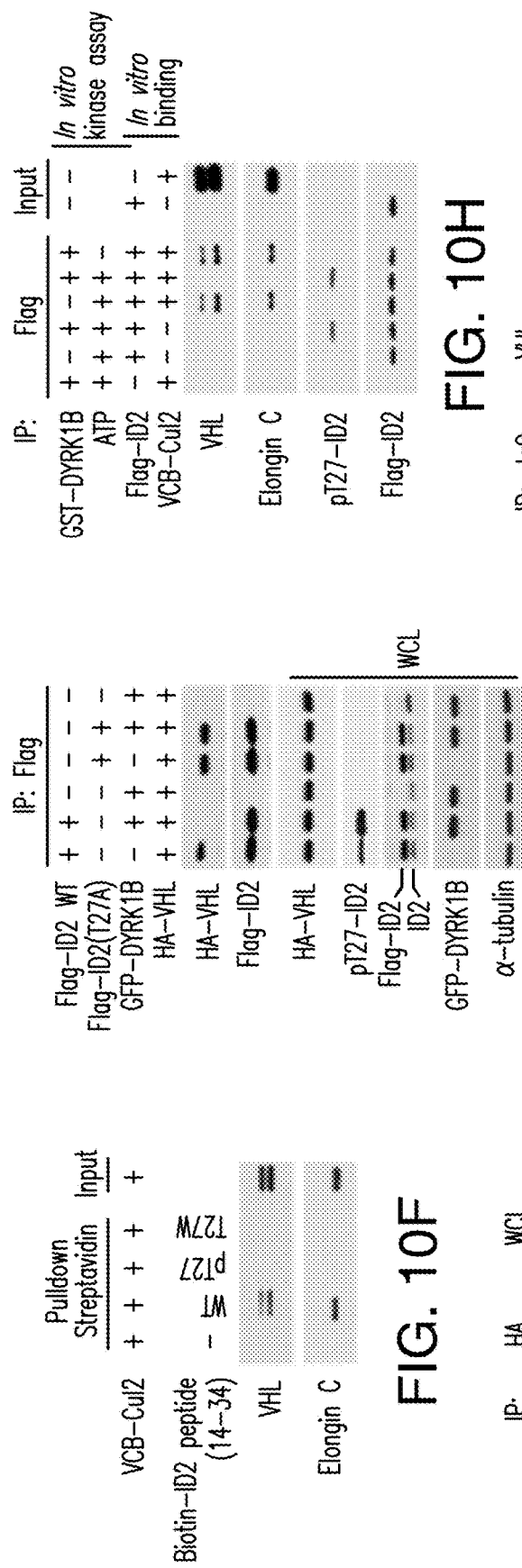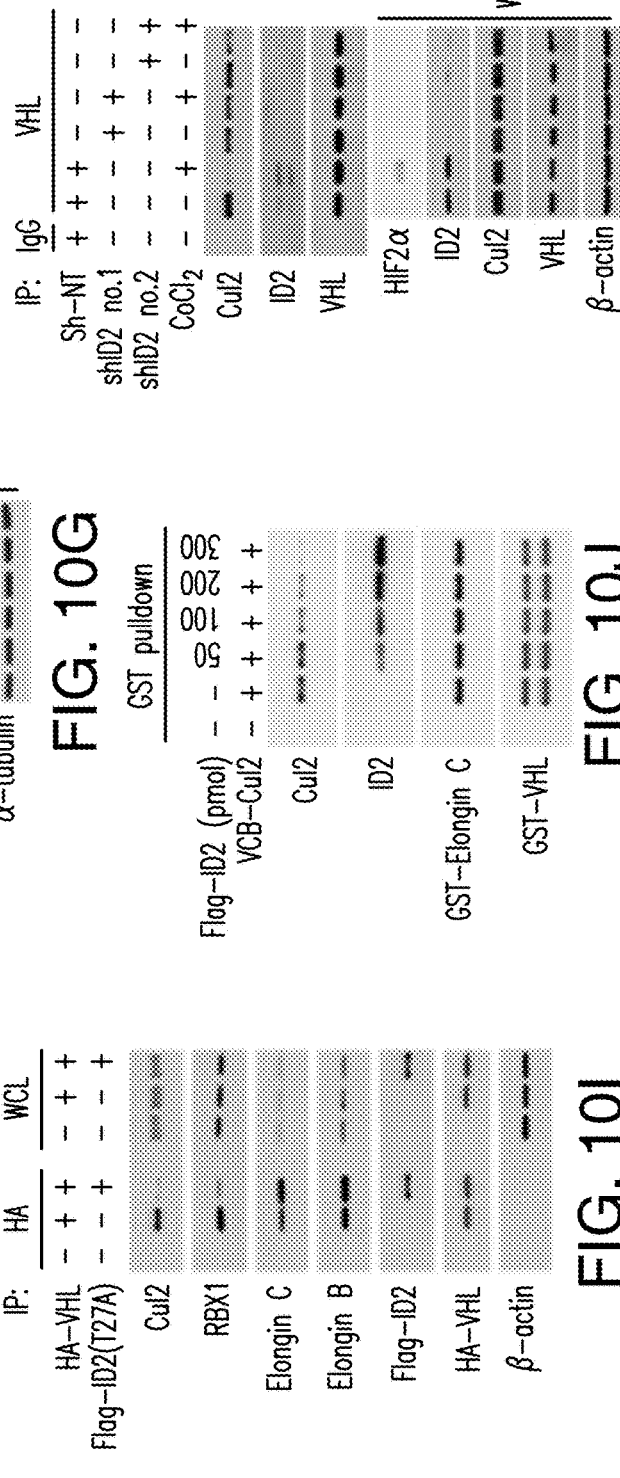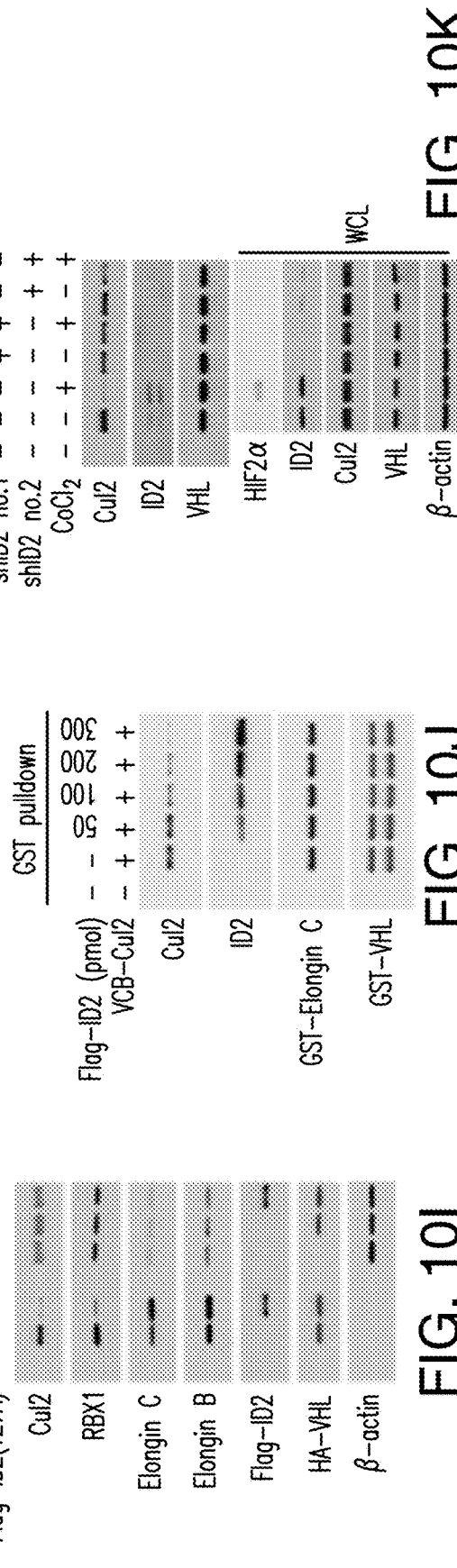
FIG. 10F
FIG. 10G
FIG. 10H
FIG. 10I
FIG. 10J
FIG. 10K

| | Protein (pg/cell±SEM) | Protein (fmol/cell±SEM) |
|---|---|---|
| ID2 | 4.959±0.514 | 0.332±0.034 |
| VHL | 1.393±0.144 | 0.058±0.006 |
| ID2:VHL | | 5.724 |

SEQUENCE LISTING

```
<160> NUMBER OF SEQ ID NOS: 141

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcctactgaa tgctgtgtat actcgagtat acacagcatt cagtaggc                 48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cccactattg tcagcctgca tctcgagatg caggctgaca atagtggg                 48

<210> SEQ ID NO 3
<211> LENGTH: 48
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 3
caggttgtaa aggcatatga tctcgagatc atatgccttt acaacctg                  48

<210> SEQ ID NO 4
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gacctacaag cacatcaatg actcgagtca ttgatgtgct tgtaggtc                  48

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Gly Ile Ser Arg Ser Lys Thr Pro Val Asp Asp Pro Met Ser
1               5                   10                  15

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gtgctcccac ggcctgta                                                    18

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttgtcacacc tatggcatat caca                                             24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
agaaggctgg ggctcatttg                                                  20

<210> SEQ ID NO 9
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
aggggccatc cacagtcttc                                                   20

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ttgctgcctc tttaagacta gga                                               23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ctggggctca aacttctctc                                                   20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
atgcctcaca cggagactgt                                                   20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagtgggttg tttgcctttg                                                   20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtggaggaag ctgacaacaa                                                   20

<210> SEQ ID NO 15
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 15
attctccagg ttgcctctca                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcccataaa tggtctttgc                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gtggtttgct tgagctgtgt                                                  20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tgcaaagaat cagaacaatg cc                                               22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cacggaggca ttctaaagtc a                                                21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
aatccccacc tgatgtgtgt                                                  20

<210> SEQ ID NO 21
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 21
gctggtctcc aggtaacgaa                                                   20

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gaaggtgaag gtcggagtca ac                                                22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cagagttaaa agcagccctg gt                                                22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgccgctaga ggtgaaattc                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctttcgctct ggtccgtctt                                                   20

<210> SEQ ID NO 26
<211> LENGTH: 14
<212> TYPE: PRT
<213> ORGANISM: Homo sapiens

<400> SEQUENCE: 26

Ala Lys Ile His Asp Ile Val Leu Val Gly Gly Ser Thr Arg
1               5                   10

<210> SEQ ID NO 27
<211> LENGTH: 17
<212> TYPE: PRT
<213> ORGANISM: Homo sapiens

<400> SEQUENCE: 27

Ser Gln Ile Phe Ser Thr Ala Ser Asp Asn Gln Pro Thr Val Thr Ile
```

1               5                   10                  15

Lys

<210> SEQ ID NO 28
<211> LENGTH: 21
<212> TYPE: PRT
<213> ORGANISM: Homo sapiens

<400> SEQUENCE: 28

Leu Tyr Gly Ser Ala Gly Pro Pro Thr Gly Glu Glu Asp Thr Ala
1               5                   10                  15

Glu Lys Asp Glu Leu
            20

<210> SEQ ID NO 29
<211> LENGTH: 16
<212> TYPE: PRT
<213> ORGANISM: Homo sapiens

<400> SEQUENCE: 29

Ile Glu Trp Leu Glu Ser His Gln Asp Ala Asp Ile Glu Asp Phe Lys
1               5                   10                  15

<210> SEQ ID NO 30
<211> LENGTH: 11
<212> TYPE: PRT
<213> ORGANISM: Homo sapiens

<400> SEQUENCE: 30

Asn Glu Leu Glu Ser Tyr Ala Tyr Ser Leu Lys
1               5                   10

<210> SEQ ID NO 31
<211> LENGTH: 15
<212> TYPE: PRT
<213> ORGANISM: Homo sapiens

<400> SEQUENCE: 31

Asn Gln Leu Thr Ser Asn Pro Glu Asn Thr Val Phe Asp Ala Lys
1               5                   10                  15

<210> SEQ ID NO 32
<211> LENGTH: 12
<212> TYPE: PRT
<213> ORGANISM: Homo sapiens

<400> SEQUENCE: 32

Glu Leu Glu Glu Ile Val Gln Pro Ile Ile Ser Lys
1               5                   10

<210> SEQ ID NO 33
<211> LENGTH: 14
<212> TYPE: PRT
<213> ORGANISM: Homo sapiens

<400> SEQUENCE: 33

Ile Thr Pro Ser Tyr Val Ala Phe Thr Pro Glu Gly Glu Arg
1               5                   10

<210> SEQ ID NO 34
<211> LENGTH: 12
<212> TYPE: PRT
<213> ORGANISM: Homo sapiens

<400> SEQUENCE: 34

Asp Ala Gly Thr Ile Ala Gly Leu Asn Val Met Arg
1               5                   10

<210> SEQ ID NO 35
<211> LENGTH: 14
<212> TYPE: PRT
<213> ORGANISM: Homo sapiens

<400> SEQUENCE: 35

Asn Gln Thr Ala Glu Lys Glu Glu Phe Glu His Gln Gln Lys
1               5                   10

<210> SEQ ID NO 36
<211> LENGTH: 11
<212> TYPE: PRT
<213> ORGANISM: Homo sapiens

<400> SEQUENCE: 36

Asn Ser Leu Glu Ser Tyr Ala Phe Asn Met Lys
1               5                   10

<210> SEQ ID NO 37
<211> LENGTH: 22
<212> TYPE: PRT
<213> ORGANISM: Homo sapiens

<400> SEQUENCE: 37

Ser Ala Lys Pro Val Gly Pro Glu Asp Met Gly Ala Thr Ala Val Tyr
1               5                   10                  15

Glu Leu Asp Thr Glu Lys
            20

<210> SEQ ID NO 38
<211> LENGTH: 12
<212> TYPE: PRT
<213> ORGANISM: Homo sapiens

<400> SEQUENCE: 38

Glu Val Asp Glu Gln Met Leu Asn Val Gln Asn Lys
1               5                   10

<210> SEQ ID NO 39
<211> LENGTH: 15
<212> TYPE: PRT
<213> ORGANISM: Homo sapiens

<400> SEQUENCE: 39

Ala Val Leu Val Asp Leu Glu Pro Gly Thr Met Asp Ser Val Arg
1               5                   10                  15

<210> SEQ ID NO 40
<211> LENGTH: 17
<212> TYPE: PRT
<213> ORGANISM: Homo sapiens

<400> SEQUENCE: 40

Glu Ile Val His Leu Gln Ala Gly Gln Cys Gly Asn Gln Ile Gly Ala
1               5                   10                  15

Lys

<210> SEQ ID NO 41
<211> LENGTH: 14

```
<212> TYPE: PRT
<213> ORGANISM: Homo sapiens

<400> SEQUENCE: 41

Leu His Phe Phe Met Pro Gly Phe Ala Pro Leu Thr Ser Arg
1               5                   10

<210> SEQ ID NO 42
<211> LENGTH: 12
<212> TYPE: PRT
<213> ORGANISM: Homo sapiens

<400> SEQUENCE: 42

Ile Asn Val Tyr Tyr Asn Glu Ala Thr Gly Gly Lys
1               5                   10

<210> SEQ ID NO 43
<211> LENGTH: 8
<212> TYPE: PRT
<213> ORGANISM: Homo sapiens

<400> SEQUENCE: 43

Ile Arg Glu Glu Tyr Pro Asp Arg
1               5

<210> SEQ ID NO 44
<211> LENGTH: 15
<212> TYPE: PRT
<213> ORGANISM: Homo sapiens

<400> SEQUENCE: 44

Ala Val Leu Val Asp Leu Glu Pro Gly Thr Met Asp Ser Val Arg
1               5                   10                  15

<210> SEQ ID NO 45
<211> LENGTH: 19
<212> TYPE: PRT
<213> ORGANISM: Homo sapiens

<400> SEQUENCE: 45

Thr Arg Pro Thr Thr Leu Gly Ser Ser Gln Phe Ser Gly Ser Gly Ile
1               5                   10                  15

Asp Glu Arg

<210> SEQ ID NO 46
<211> LENGTH: 16
<212> TYPE: PRT
<213> ORGANISM: Homo sapiens

<400> SEQUENCE: 46

Gly Gly Leu Gln Ser Gln Ser Gly Thr Val Val Thr Thr Glu Ile Lys
1               5                   10                  15

<210> SEQ ID NO 47
<211> LENGTH: 22
<212> TYPE: PRT
<213> ORGANISM: Homo sapiens

<400> SEQUENCE: 47

Lys Val Pro Pro Gly Leu Pro Ser Ser Val Tyr Ala Pro Ser Pro Asn
1               5                   10                  15

Ser Asp Asp Phe Asn Arg
                20
```

```
<210> SEQ ID NO 48
<211> LENGTH: 16
<212> TYPE: PRT
<213> ORGANISM: Homo sapiens

<400> SEQUENCE: 48

Gln Asp Leu Gly Leu Gly Ser Pro Ala Gln Leu Ser Ser Ser Gly Lys
 1               5                  10                  15

<210> SEQ ID NO 49
<211> LENGTH: 9
<212> TYPE: PRT
<213> ORGANISM: Homo sapiens

<400> SEQUENCE: 49

Leu Asp Asp Ala Ile His Val Leu Arg
 1               5

<210> SEQ ID NO 50
<211> LENGTH: 27
<212> TYPE: PRT
<213> ORGANISM: Homo sapiens

<400> SEQUENCE: 50

Gly Ser Thr Ser Ser Ser Pro Tyr Val Ala Ala Ser His Thr Pro Pro
 1               5                  10                  15

Ile Asn Gly Ser Asp Ser Ile Leu Gly Thr Arg
            20                  25

<210> SEQ ID NO 51
<211> LENGTH: 29
<212> TYPE: PRT
<213> ORGANISM: Homo sapiens

<400> SEQUENCE: 51

Val Ser Ala Val Ser Ala Glu Pro Pro Thr Thr Leu Pro Gly Thr His
 1               5                  10                  15

Pro Gly Leu Ser Glu Thr Thr Asn Pro Met Gly His Met
            20                  25

<210> SEQ ID NO 52
<211> LENGTH: 13
<212> TYPE: PRT
<213> ORGANISM: Homo sapiens

<400> SEQUENCE: 52

Asp Thr Gly Leu Pro Gly Cys Gln Ser Ser Leu Leu Arg
 1               5                  10

<210> SEQ ID NO 53
<211> LENGTH: 14
<212> TYPE: PRT
<213> ORGANISM: Homo sapiens

<400> SEQUENCE: 53

Pro Gly Thr Ala Tyr Tyr Ser Phe Ser Ala Thr Ser Ser Arg
 1               5                  10

<210> SEQ ID NO 54
<211> LENGTH: 13
<212> TYPE: PRT
<213> ORGANISM: Homo sapiens

<400> SEQUENCE: 54
```

```
Ile Glu Asp His Leu Asp Glu Ala Ile His Val Leu Arg
1               5                   10

<210> SEQ ID NO 55
<211> LENGTH: 20
<212> TYPE: PRT
<213> ORGANISM: Homo sapiens

<400> SEQUENCE: 55

Val Pro Pro Gly Leu Pro Ser Ser Val Tyr Pro Pro Ser Ser Gly Glu
1               5                   10                  15

Asp Tyr Gly Arg
            20

<210> SEQ ID NO 56
<211> LENGTH: 14
<212> TYPE: PRT
<213> ORGANISM: Homo sapiens

<400> SEQUENCE: 56

Gly Thr Ser Gln Tyr Tyr Pro Ser Tyr Ser Gly Ser Ser Arg
1               5                   10

<210> SEQ ID NO 57
<211> LENGTH: 21
<212> TYPE: PRT
<213> ORGANISM: Homo sapiens

<400> SEQUENCE: 57

Lys Val Pro Pro Gly Leu Pro Ser Ser Val Tyr Pro Pro Ser Ser Gly
1               5                   10                  15

Glu Asp Tyr Gly Arg
            20

<210> SEQ ID NO 58
<211> LENGTH: 16
<212> TYPE: PRT
<213> ORGANISM: Homo sapiens

<400> SEQUENCE: 58

Thr Ser Pro Asp Glu Asp Glu Asp Leu Leu Pro Pro Glu Gln Lys
1               5                   10                  15

<210> SEQ ID NO 59
<211> LENGTH: 11
<212> TYPE: PRT
<213> ORGANISM: Homo sapiens

<400> SEQUENCE: 59

Ala Gly Ala Thr Ala Ala Ala Ser Glu Ile Lys
1               5                   10

<210> SEQ ID NO 60
<211> LENGTH: 29
<212> TYPE: PRT
<213> ORGANISM: Homo sapiens

<400> SEQUENCE: 60

Val Ser Gly Val Val Gly Asp Pro Gln Met Val Leu Ser Ala Pro His
1               5                   10                  15

Pro Gly Leu Ser Glu Ala His Asn Pro Ala Gly His Met
            20                  25
```

```
<210> SEQ ID NO 61
<211> LENGTH: 11
<212> TYPE: PRT
<213> ORGANISM: Homo sapiens

<400> SEQUENCE: 61

Ile Gly Gly Ile Gly Thr Val Pro Val Gly Arg
1               5                   10

<210> SEQ ID NO 62
<211> LENGTH: 8
<212> TYPE: PRT
<213> ORGANISM: Homo sapiens

<400> SEQUENCE: 62

Leu Pro Leu Gln Asp Val Tyr Lys
1               5

<210> SEQ ID NO 63
<211> LENGTH: 19
<212> TYPE: PRT
<213> ORGANISM: Homo sapiens

<400> SEQUENCE: 63

Thr Pro Val Asp Asp Pro Met Ser Leu Leu Tyr Asn Met Asn Asp Cys
1               5                   10                  15

Tyr Ser Lys

<210> SEQ ID NO 64
<211> LENGTH: 19
<212> TYPE: PRT
<213> ORGANISM: Homo sapiens

<400> SEQUENCE: 64

Thr Pro Val Asp Asp Pro Met Ser Leu Leu Tyr Asn Met Asn Asp Cys
1               5                   10                  15

Tyr Ser Lys

<210> SEQ ID NO 65
<211> LENGTH: 21
<212> TYPE: PRT
<213> ORGANISM: Homo sapiens

<400> SEQUENCE: 65

Ser Lys Thr Pro Val Asp Asp Pro Met Ser Leu Leu Tyr Asn Met Asn
1               5                   10                  15

Asp Cys Tyr Ser Lys
            20

<210> SEQ ID NO 66
<211> LENGTH: 19
<212> TYPE: PRT
<213> ORGANISM: Homo sapiens

<400> SEQUENCE: 66

Thr Pro Val Asp Asp Pro Met Ser Leu Leu Tyr Asn Met Asn Asp Cys
1               5                   10                  15

Tyr Ser Lys

<210> SEQ ID NO 67
<211> LENGTH: 12
<212> TYPE: PRT
```

```
<213> ORGANISM: Homo sapiens

<400> SEQUENCE: 67

Asn Ser Leu Ser Asp His Ser Leu Gly Ile Ser Arg
1               5                   10

<210> SEQ ID NO 68
<211> LENGTH: 12
<212> TYPE: PRT
<213> ORGANISM: Homo sapiens

<400> SEQUENCE: 68

Leu Lys Glu Leu Val Pro Ser Ile Pro Gln Asn Lys
1               5                   10

<210> SEQ ID NO 69
<211> LENGTH: 19
<212> TYPE: PRT
<213> ORGANISM: Homo sapiens

<400> SEQUENCE: 69

Thr Pro Val Asp Asp Pro Met Ser Leu Leu Tyr Asn Met Asn Asp Cys
1               5                   10                  15

Tyr Ser Lys

<210> SEQ ID NO 70
<211> LENGTH: 10
<212> TYPE: PRT
<213> ORGANISM: Homo sapiens

<400> SEQUENCE: 70

Glu Leu Val Pro Ser Ile Pro Gln Asn Lys
1               5                   10

<210> SEQ ID NO 71
<211> LENGTH: 21
<212> TYPE: PRT
<213> ORGANISM: Homo sapiens

<400> SEQUENCE: 71

Ser Lys Thr Pro Val Asp Asp Pro Met Ser Leu Leu Tyr Asn Met Asn
1               5                   10                  15

Asp Cys Tyr Ser Lys
                20

<210> SEQ ID NO 72
<211> LENGTH: 14
<212> TYPE: PRT
<213> ORGANISM: Homo sapiens

<400> SEQUENCE: 72

Ser Asn Ser Phe Phe Glu Gly Val Asp Trp Glu His Ile Arg
1               5                   10

<210> SEQ ID NO 73
<211> LENGTH: 11
<212> TYPE: PRT
<213> ORGANISM: Homo sapiens

<400> SEQUENCE: 73

Glu Arg Pro Ala Ala Ile Ser Ile Glu Ile Lys
1               5                   10
```

-continued

```
<210> SEQ ID NO 74
<211> LENGTH: 10
<212> TYPE: PRT
<213> ORGANISM: Homo sapiens

<400> SEQUENCE: 74

Asp Trp Val Phe Ile Asn Tyr Thr Tyr Lys
1               5                   10

<210> SEQ ID NO 75
<211> LENGTH: 16
<212> TYPE: PRT
<213> ORGANISM: Homo sapiens

<400> SEQUENCE: 75

Ile Ile Asn Glu Pro Thr Ala Ala Ile Ala Tyr Gly Leu Asp Arg
1               5                   10                  15

<210> SEQ ID NO 76
<211> LENGTH: 15
<212> TYPE: PRT
<213> ORGANISM: Homo sapiens

<400> SEQUENCE: 76

Asn Gln Val Ala Leu Asn Pro Gln Asn Thr Val Phe Asp Ala Lys
1               5                   10                  15

<210> SEQ ID NO 77
<211> LENGTH: 12
<212> TYPE: PRT
<213> ORGANISM: Homo sapiens

<400> SEQUENCE: 77

Asp Ala Gly Val Ile Ala Gly Leu Asn Val Leu Arg
1               5                   10

<210> SEQ ID NO 78
<211> LENGTH: 14
<212> TYPE: PRT
<213> ORGANISM: Homo sapiens

<400> SEQUENCE: 78

Ala Gln Ile His Asp Leu Val Leu Val Gly Gly Ser Thr Arg
1               5                   10

<210> SEQ ID NO 79
<211> LENGTH: 11
<212> TYPE: PRT
<213> ORGANISM: Homo sapiens

<400> SEQUENCE: 79

Asn Ala Leu Glu Ser Tyr Ala Phe Asn Met Lys
1               5                   10

<210> SEQ ID NO 80
<211> LENGTH: 10
<212> TYPE: PRT
<213> ORGANISM: Homo sapiens

<400> SEQUENCE: 80

Leu Val Asn His Phe Val Glu Glu Phe Lys
1               5                   10

<210> SEQ ID NO 81
<211> LENGTH: 31
```

<212> TYPE: PRT
<213> ORGANISM: Homo sapiens

<400> SEQUENCE: 81

Glu Leu Glu Gln Val Cys Asn Pro Ile Ile Ser Gly Leu Tyr Gln Gly
1               5                   10                  15

Ala Gly Gly Pro Gly Pro Gly Phe Gly Ala Gln Gly Pro Lys
            20                  25                  30

<210> SEQ ID NO 82
<211> LENGTH: 13
<212> TYPE: PRT
<213> ORGANISM: Homo sapiens

<400> SEQUENCE: 82

Thr Thr Pro Ser Tyr Val Ala Phe Thr Asp Thr Glu Arg
1               5                   10

<210> SEQ ID NO 83
<211> LENGTH: 11
<212> TYPE: PRT
<213> ORGANISM: Homo sapiens

<400> SEQUENCE: 83

Phe Gly Asp Pro Val Val Gln Ser Asp Met Lys
1               5                   10

<210> SEQ ID NO 84
<211> LENGTH: 16
<212> TYPE: PRT
<213> ORGANISM: Homo sapiens

<400> SEQUENCE: 84

Cys Gln Glu Val Ile Ser Trp Leu Asp Ala Asn Thr Leu Ala Glu Lys
1               5                   10                  15

<210> SEQ ID NO 85
<211> LENGTH: 10
<212> TYPE: PRT
<213> ORGANISM: Homo sapiens

<400> SEQUENCE: 85

Phe Glu Glu Leu Cys Ser Asp Leu Phe Arg
1               5                   10

<210> SEQ ID NO 86
<211> LENGTH: 9
<212> TYPE: PRT
<213> ORGANISM: Homo sapiens

<400> SEQUENCE: 86

Leu Leu Gln Asp Phe Phe Asn Gly Arg
1               5

<210> SEQ ID NO 87
<211> LENGTH: 14
<212> TYPE: PRT
<213> ORGANISM: Homo sapiens

<400> SEQUENCE: 87

Ala Phe Tyr Pro Glu Glu Ile Ser Ser Met Val Leu Thr Lys
1               5                   10

<210> SEQ ID NO 88

<211> LENGTH: 12
<212> TYPE: PRT
<213> ORGANISM: Homo sapiens

<400> SEQUENCE: 88

Lys Phe Gly Asp Pro Val Val Gln Ser Asp Met Lys
1               5                   10

<210> SEQ ID NO 89
<211> LENGTH: 16
<212> TYPE: PRT
<213> ORGANISM: Homo sapiens

<400> SEQUENCE: 89

Ile Ile Asn Glu Pro Thr Ala Ala Ile Ala Tyr Gly Leu Asp Lys
1               5                   10                  15

<210> SEQ ID NO 90
<211> LENGTH: 15
<212> TYPE: PRT
<213> ORGANISM: Homo sapiens

<400> SEQUENCE: 90

Asn Gln Val Ala Met Asn Pro Thr Asn Thr Val Phe Asp Ala Lys
1               5                   10                  15

<210> SEQ ID NO 91
<211> LENGTH: 31
<212> TYPE: PRT
<213> ORGANISM: Homo sapiens

<400> SEQUENCE: 91

Ser Glu Asn Val Gln Asp Leu Leu Leu Asp Val Thr Pro Leu Ser
1               5                   10                  15

Leu Gly Ile Glu Thr Ala Gly Gly Val Met Thr Val Leu Ile Lys
                20                  25                  30

<210> SEQ ID NO 92
<211> LENGTH: 11
<212> TYPE: PRT
<213> ORGANISM: Homo sapiens

<400> SEQUENCE: 92

Phe Asp Asp Ala Val Val Gln Ser Asp Met Lys
1               5                   10

<210> SEQ ID NO 93
<211> LENGTH: 12
<212> TYPE: PRT
<213> ORGANISM: Homo sapiens

<400> SEQUENCE: 93

Arg Phe Asp Asp Ala Val Val Gln Ser Asp Met Lys
1               5                   10

<210> SEQ ID NO 94
<211> LENGTH: 18
<212> TYPE: PRT
<213> ORGANISM: Homo sapiens

<400> SEQUENCE: 94

Thr Val Thr Asn Ala Val Val Thr Val Pro Ala Tyr Phe Asn Asp Ser
1               5                   10                  15

Gln Arg

<210> SEQ ID NO 95
<211> LENGTH: 12
<212> TYPE: PRT
<213> ORGANISM: Homo sapiens

<400> SEQUENCE: 95

Asp Ala Gly Thr Ile Ala Gly Leu Asn Val Leu Arg
1               5                   10

<210> SEQ ID NO 96
<211> LENGTH: 14
<212> TYPE: PRT
<213> ORGANISM: Homo sapiens

<400> SEQUENCE: 96

Ser Phe Tyr Pro Glu Glu Val Ser Ser Met Val Leu Thr Lys
1               5                   10

<210> SEQ ID NO 97
<211> LENGTH: 14
<212> TYPE: PRT
<213> ORGANISM: Homo sapiens

<400> SEQUENCE: 97

Ser Gln Ile His Asp Ile Val Leu Val Gly Gly Ser Thr Arg
1               5                   10

<210> SEQ ID NO 98
<211> LENGTH: 12
<212> TYPE: PRT
<213> ORGANISM: Homo sapiens

<400> SEQUENCE: 98

Glu Leu Glu Glu Ile Val Gln Pro Leu Ile Ser Lys
1               5                   10

<210> SEQ ID NO 99
<211> LENGTH: 15
<212> TYPE: PRT
<213> ORGANISM: Homo sapiens

<400> SEQUENCE: 99

Ser Asp Gly Ala Leu Leu Leu Gly Ala Ser Ser Leu Ser Gly Arg
1               5                   10                  15

<210> SEQ ID NO 100
<211> LENGTH: 12
<212> TYPE: PRT
<213> ORGANISM: Homo sapiens

<400> SEQUENCE: 100

Asp Ser Val Phe Leu Ser Cys Ser Glu Asp Asn Arg
1               5                   10

<210> SEQ ID NO 101
<211> LENGTH: 14
<212> TYPE: PRT
<213> ORGANISM: Homo sapiens

<400> SEQUENCE: 101

Glu Trp Asn Leu Pro Pro Asn Ala Pro Ala Cys Met Glu Arg
1               5                   10

```
<210> SEQ ID NO 102
<211> LENGTH: 21
<212> TYPE: PRT
<213> ORGANISM: Homo sapiens

<400> SEQUENCE: 102

Ala Gly Ala Asp Thr His Gly Arg Leu Leu Gln Gly Asn Ile Cys Asn
1               5                   10                  15
Asp Ala Val Thr Lys
            20

<210> SEQ ID NO 103
<211> LENGTH: 13
<212> TYPE: PRT
<213> ORGANISM: Homo sapiens

<400> SEQUENCE: 103

Ala Ala Ile Leu Pro Thr Ser Ile Phe Leu Thr Asn Lys
1               5                   10

<210> SEQ ID NO 104
<211> LENGTH: 20
<212> TYPE: PRT
<213> ORGANISM: Homo sapiens

<400> SEQUENCE: 104

Val Pro Glu Glu Glu Lys Asp Thr Asn Val Gln Val Leu Met Val Leu
1               5                   10                  15
Gly Ala Gly Arg
            20

<210> SEQ ID NO 105
<211> LENGTH: 20
<212> TYPE: PRT
<213> ORGANISM: Homo sapiens

<400> SEQUENCE: 105

Asp Asp Ile Ile Glu Asn Ala Pro Thr Thr His Thr Glu Glu Tyr Ser
1               5                   10                  15
Gly Glu Glu Lys
            20

<210> SEQ ID NO 106
<211> LENGTH: 10
<212> TYPE: PRT
<213> ORGANISM: Homo sapiens

<400> SEQUENCE: 106

Val Pro Leu Val Ala Pro Glu Asp Leu Arg
1               5                   10

<210> SEQ ID NO 107
<211> LENGTH: 21
<212> TYPE: PRT
<213> ORGANISM: Homo sapiens

<400> SEQUENCE: 107

Asp Asp Gly Val Ser Ile Pro Gly Glu Tyr Thr Ser Phe Leu Ala Pro
1               5                   10                  15
Ile Ser Ser Ser Lys
            20

<210> SEQ ID NO 108
```

-continued

```
<211> LENGTH: 17
<212> TYPE: PRT
<213> ORGANISM: Homo sapiens

<400> SEQUENCE: 108

Asp Leu Asn Cys Val Pro Glu Ile Ala Asp Thr Leu Gly Ala Val Ala
1               5                   10                  15

Lys

<210> SEQ ID NO 109
<211> LENGTH: 9
<212> TYPE: PRT
<213> ORGANISM: Homo sapiens

<400> SEQUENCE: 109

Asp Trp Asn Thr Leu Ile Val Gly Lys
1               5

<210> SEQ ID NO 110
<211> LENGTH: 15
<212> TYPE: PRT
<213> ORGANISM: Homo sapiens

<400> SEQUENCE: 110

Ala Val Phe Val Asp Leu Glu Pro Thr Val Ile Asp Glu Val Arg
1               5                   10                  15

<210> SEQ ID NO 111
<211> LENGTH: 13
<212> TYPE: PRT
<213> ORGANISM: Homo sapiens

<400> SEQUENCE: 111

Ser Ile Gln Phe Val Asp Trp Cys Pro Thr Gly Phe Lys
1               5                   10

<210> SEQ ID NO 112
<211> LENGTH: 9
<212> TYPE: PRT
<213> ORGANISM: Homo sapiens

<400> SEQUENCE: 112

Glu Ile Ile Asp Leu Val Leu Asp Arg
1               5

<210> SEQ ID NO 113
<211> LENGTH: 21
<212> TYPE: PRT
<213> ORGANISM: Homo sapiens

<400> SEQUENCE: 113

Asp Tyr Glu Glu Val Gly Val Asp Ser Val Glu Gly Glu Gly Glu Glu
1               5                   10                  15

Glu Gly Glu Glu Tyr
                20

<210> SEQ ID NO 114
<211> LENGTH: 17
<212> TYPE: PRT
<213> ORGANISM: Homo sapiens

<400> SEQUENCE: 114

Met Ala Val Thr Phe Ile Gly Asn Ser Thr Ala Ile Gln Glu Leu Phe
1               5                   10                  15
```

Lys

<210> SEQ ID NO 115
<211> LENGTH: 15
<212> TYPE: PRT
<213> ORGANISM: Homo sapiens

<400> SEQUENCE: 115

Ala Leu Thr Val Pro Glu Leu Thr Gln Gln Val Phe Asp Ala Lys
1               5                   10                  15

<210> SEQ ID NO 116
<211> LENGTH: 12
<212> TYPE: PRT
<213> ORGANISM: Homo sapiens

<400> SEQUENCE: 116

Ile Ser Val Tyr Tyr Asn Glu Ala Thr Gly Gly Lys
1               5                   10

<210> SEQ ID NO 117
<211> LENGTH: 17
<212> TYPE: PRT
<213> ORGANISM: Homo sapiens

<400> SEQUENCE: 117

Glu Ile Val His Ile Gln Ala Gly Gln Cys Gly Asn Gln Ile Gly Ala
1               5                   10                  15

Lys

<210> SEQ ID NO 118
<211> LENGTH: 19
<212> TYPE: PRT
<213> ORGANISM: Homo sapiens

<400> SEQUENCE: 118

Ser Thr Asn Gly Asp Thr Phe Leu Gly Gly Glu Asp Phe Asp Gln Ala
1               5                   10                  15

Leu Leu Arg

<210> SEQ ID NO 119
<211> LENGTH: 14
<212> TYPE: PRT
<213> ORGANISM: Homo sapiens

<400> SEQUENCE: 119

Thr Thr Pro Ser Val Val Ala Phe Thr Ala Asp Gly Glu Arg
1               5                   10

<210> SEQ ID NO 120
<211> LENGTH: 18
<212> TYPE: PRT
<213> ORGANISM: Homo sapiens

<400> SEQUENCE: 120

Asn Leu Asn His Ser Leu Pro Ser Asp Phe Thr Phe Gln Asn Met Asn
1               5                   10                  15

Ser Lys

<210> SEQ ID NO 121
<211> LENGTH: 11
<212> TYPE: PRT

<213> ORGANISM: Homo sapiens

<400> SEQUENCE: 121

Leu Ser Asp Phe Gly Leu Cys Thr Gly Leu Lys
1               5                   10

<210> SEQ ID NO 122
<211> LENGTH: 10
<212> TYPE: PRT
<213> ORGANISM: Homo sapiens

<400> SEQUENCE: 122

Leu Gly Leu Glu Asp Phe Glu Ser Leu Lys
1               5                   10

<210> SEQ ID NO 123
<211> LENGTH: 12
<212> TYPE: PRT
<213> ORGANISM: Homo sapiens

<400> SEQUENCE: 123

Asp Ile Lys Pro Asp Asn Leu Leu Asp Ser Lys
1               5                   10

<210> SEQ ID NO 124
<211> LENGTH: 10
<212> TYPE: PRT
<213> ORGANISM: Homo sapiens

<400> SEQUENCE: 124

Ile Gly Ala Pro Gly Val Glu Glu Ile Lys
1               5                   10

<210> SEQ ID NO 125
<211> LENGTH: 14
<212> TYPE: PRT
<213> ORGANISM: Homo sapiens

<400> SEQUENCE: 125

Glu Thr Leu Thr Phe Pro Pro Glu Val Pro Ile Ser Glu Lys
1               5                   10

<210> SEQ ID NO 126
<211> LENGTH: 19
<212> TYPE: PRT
<213> ORGANISM: Homo sapiens

<400> SEQUENCE: 126

Glu Phe Asp Glu Asp Val Tyr Asn His Lys Thr Pro Glu Ser Asn Ile
1               5                   10                  15

Lys Met Lys

<210> SEQ ID NO 127
<211> LENGTH: 20
<212> TYPE: PRT
<213> ORGANISM: Homo sapiens

<400> SEQUENCE: 127

Ala Met Leu Ser Gly Pro Gly Gln Phe Ala Glu Asn Glu Thr Asn Glu
1               5                   10                  15

Val Asn Phe Arg
            20

<210> SEQ ID NO 128
<211> LENGTH: 18
<212> TYPE: DNA
<213> ORGANISM: Homo sapiens

<400> SEQUENCE: 128
cggagcaaaa ccctgtg                                                    18

<210> SEQ ID NO 129
<211> LENGTH: 18
<212> TYPE: DNA
<213> ORGANISM: Homo sapiens

<400> SEQUENCE: 129
cggagcaaag ccctgtg                                                    18

<210> SEQ ID NO 130
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 130 cgg agc aaa acc cct gtg                                               18
Arg Ser Lys Thr Pro Val
1               5

<210> SEQ ID NO 131
<211> LENGTH: 6
<212> TYPE: PRT
<213> ORGANISM: Homo sapiens

<400> SEQUENCE: 131

Arg Ser Lys Thr Pro Val
1               5

<210> SEQ ID NO 132
<211> LENGTH: 18
<212> TYPE: DNA
<213> ORGANISM: Homo sapiens
<220> FEATURE:
<221> NAME/KEY: CDS
<222> LOCATION: (1)..(18)

<400> SEQUENCE: 132 cgg agc aaa gcc cct gtg                                               18
Arg Ser Lys Ala Pro Val
1               5

<210> SEQ ID NO 133
<211> LENGTH: 6
<212> TYPE: PRT
<213> ORGANISM: Homo sapiens

<400> SEQUENCE: 133

Arg Ser Lys Ala Pro Val
1               5

<210> SEQ ID NO 134
<211> LENGTH: 50
<212> TYPE: PRT
<213> ORGANISM: Homo sapiens

<400> SEQUENCE: 134

-continued

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val
    50

<210> SEQ ID NO 135
<211> LENGTH: 50
<212> TYPE: PRT
<213> ORGANISM: Macaca mulatta

<400> SEQUENCE: 135

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val
    50

<210> SEQ ID NO 136
<211> LENGTH: 50
<212> TYPE: PRT
<213> ORGANISM: Bos taurus

<400> SEQUENCE: 136

Met Lys Ala Phe Ser Pro Val Arg Ser Val Arg Lys Asn Ser Leu Ser
1               5                   10                  15

Asp His Gly Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val
    50

<210> SEQ ID NO 137
<211> LENGTH: 50
<212> TYPE: PRT
<213> ORGANISM: Mus musculus

<400> SEQUENCE: 137

Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
            20                  25                  30

Met Ser Leu Leu Tyr Asn Met Asn Asp Cys Tyr Ser Lys Leu Lys Glu
        35                  40                  45

Leu Val
    50

<210> SEQ ID NO 138
<211> LENGTH: 50
<212> TYPE: PRT
<213> ORGANISM: Rattus norvegicus

<400> SEQUENCE: 138
```

```
Met Lys Ala Phe Ser Pro Val Arg Ser Val Arg Lys Asn Ser Leu Ser
1               5                   10                  15

Asp His Ser Leu Gly Ile Ser Arg Ser Lys Thr Pro Val Asp Asp Pro
                20                  25                  30

Met Ser Leu Leu Tyr Asn Met Asn Asp Cys Tyr Ser Lys Leu Lys Glu
        35                  40                  45

Leu Val
    50

<210> SEQ ID NO 139
<211> LENGTH: 50
<212> TYPE: PRT
<213> ORGANISM: Gallus gallus

<400> SEQUENCE: 139

Met Lys Ala Phe Ser Pro Val Arg Ser Val Arg Lys Asn Gly Leu Ser
1               5                   10                  15

Glu His Asn Leu Gly Ile Ser Arg Ser Lys Thr Pro Val Asp Asp Pro
                20                  25                  30

Met Ser Leu Leu Tyr Asn Met Asn Asp Cys Tyr Ser Lys Leu Lys Glu
        35                  40                  45

Leu Val
    50

<210> SEQ ID NO 140
<211> LENGTH: 50
<212> TYPE: PRT
<213> ORGANISM: Xenopus tropicalis

<400> SEQUENCE: 140

Met Lys Ala Phe Ser Pro Val Arg Ser Val Arg Lys Ser Ser Leu Thr
1               5                   10                  15

Glu His Ser Leu Gly Ile Ala Arg Ser Lys Thr Pro Val Asp Asp Pro
                20                  25                  30

Met Ser Leu Leu Tyr Asn Met Asn Asp Cys Tyr Ser Lys Leu Lys Glu
        35                  40                  45

Leu Val
    50

<210> SEQ ID NO 141
<211> LENGTH: 54
<212> TYPE: PRT
<213> ORGANISM: Danio rerio

<400> SEQUENCE: 141

Met Lys Ala Ile Ser Pro Val Arg Ser Phe Arg Lys Ser Ser Ala Ser
1               5                   10                  15

Val Thr Thr Thr Glu His Ser Leu Gly Ile Ser Arg Ser Lys Thr Pro
                20                  25                  30

Val Asp Asp Pro Leu Ser Leu Leu Tyr Asn Met Asn Asp Cys Tyr Ser
        35                  40                  45

Lys Leu Lys Glu Leu Val
    50
```

COMPOSITIONS AND METHODS FOR REGULATING ACTIVITY OF INHIBITOR OF DNA BINDING-2 (ID2) PROTEIN AND FOR TREATING ID PROTEIN-RELATED DISEASES

PRIORITY CLAIM

The present application is a continuation of PCT Application Serial No. PCT/US2017/012352 filed Jan. 5, 2017; which claims priority to U.S. Provisional Patent Application Ser. No. 62/274,871, filed Jan. 5, 2016 and titled "AN INHIBITOR OF DNA BINDING-2 (ID-2) PROTEIN-DEPENDENT MECHANISM FOR VHL INACTIVATION IN CANCER," the entirety of which are incorporated by reference herein.

STATEMENT OF GOVERNMENT INTEREST

This invention was made with government support under CA101644, CA131126, CA178546, and NS061776 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Feb. 17, 2017, is named 6121SequenceListing.txt and is 31,000 bytes in size.

TECHNICAL FIELD

The present disclosure relates to compositions and methods for regulating the activity of the Inhibitor of DNA Binding-2 (ID2) protein and for treating an ID protein-related disease, such as a tumor or cancer.

BACKGROUND

Inhibitor of DNA Binding (ID) proteins are transcriptional regulators that control the timing of cell fate determination and differentiation in stem and progenitor cells during normal development and adult life. ID proteins have the ability to control specific genes which regulate cell proliferation and cell-cycle progression in a variety of mature and embryonic cell types, including vascular smooth muscle cell and endothelial cells. ID genes are frequently dysregulated in many types of human neoplasms, and they endow cancer cells with biological features hijacked from normal stem cells that often prove very detrimental to the cancer patient. ID proteins frequently coordinate of multiple cancer hallmarks, such that they are even recognized as important biomarkers in some types of tumors, including human tumors.

Although the pro-tumorigenic role of ID proteins has been linked to the accumulation of mRNAs and proteins, it remains unclear whether other mechanisms exist that dysregulate ID activity in cancer cells. Among ID proteins, ID2 is essential for tumor angiogenesis and glioma stemness and it is a component of the biomarker signature that predicts poor outcome in patients with high-grade glioma.

The Hypoxia-Inducible Factor-$\alpha$ (HIF$\alpha$) transcription factors are the key mediators of the hypoxia response, but HIF$\alpha$ protein dysregulation in cancer can be triggered by mutation of the von-Hippel Lindau (VHL) gene. Mutation of the VHL gene hinders the negative control of HIF$\alpha$ protein stability through the ubiquitin ligase activity of VHL. This idea has been validated for HIF2$\alpha$, the HIF isoform preferentially upregulated in VHL-mutant tumors and has recently been implicated as a driver of cancer stem cells. However, signaling events that link the stem cell-intrinsic transcriptional machinery to pivotal mechanisms of HIF2$\alpha$ regulation in cancer are presently unknown.

Dual-Specificity Tyrosine-Phosphorylation-Regulated Protein Kinase 1A and 1B (collectively referred to herein as DYRK1), are two forms or a protein associated with Down Syndrome. The gene coding for DYRK1A is gained in Down syndrome, a disease characterized by impaired neural proliferation during development, reduced self-renewal and premature withdrawal from the cell cycle. However, DYRK1 has not previously been linked to ID2 or HIF$\alpha$ activity.

SUMMARY

The present disclosure provides, in one embodiment, a method of treating or preventing an ID2 protein-related disease in a patient at risk of developing or having such a disease by administering to the patient a composition in an amount and for a time sufficient to increase degradation of HIF$\alpha$ in a cell affected by the ID2 protein-related disease in the patent and/or to decrease half-life of HIF$\alpha$ in the cell affected by the ID2 protein-related disease in the patient, as compared to an untreated cell affected by the ID2 protein-related disease.

The disclosure further provides the following additional embodiments, which can be combined with the above method and with one another unless clearly mutually exclusive:

i) the HIF$\alpha$ can include HIF2$\alpha$;

ii) the method can include increasing degradation of HIF$\alpha$ or decreasing half-life of HIF$\alpha$ by increasing phosphorylation of ID2 protein on Thr27 in the cell as compared to an untreated cell affected by the ID2 protein-related disease;

iii) the method can include increasing the amount or activity of DYRK1 in the cell as compared to an untreated cell affected by the ID2 protein-related disease;

iv) the method can include increasing phosphorylation of ID2 protein on Thr27 by increasing the amount or activity of DYRK1 in the cell as compared to an untreated cell affected by the ID2 protein-related disease;

v) the method can include increasing dissociation of ID2 from a VHL protein in the cell as compared to an untreated cell affected by the ID2 protein-related disease;

vi) the method can include increasing ubiquitylation of the HIF$\alpha$ in the cell as compared to an untreated cell affected by the ID2 protein-related disease;

vii) the ID2 protein-related disease can be a cancer, a tumor, a metabolic disease, a vascular disease, a neurodegernative disease, and/or a renal disease;

a) a cancer or tumor can be a glioma, a retinoblastoma, an ewings sarcoma, and/or a lymphoma;

viii) preventing can include delaying or preventing the onset of one or more symptoms of an ID2 protein-related disease for at least a set period of time;

ix) treating can include delaying or preventing the progression of one or more symptoms of an ID2 protein-related disease for at least a set period time, causing a regression of one or more symptoms of an ID2 protein-related disease for at least a set period of time, and/or causing the disappearance of one or more symptoms of and ID2 protein-related disease for at least a set period of time;

x) the composition can include an isolated DYRK1 protein, an isolated prolyl hydroxylase (PHD) protein, a tetracycline, receptor activator of nuclear factor kappa-B ligand (RANKL) cytokine, homocysteine, or any combinations thereof;
   a) the DYRK1 protein can be a recombinant DYRK1 protein;
   b) the PHD protein can be a recombinant PHD protein.

The present disclosure further includes the use of a composition to prevent or treat an ID2 protein-related disease via any of the steps described above. The composition can include an isolated DYRK1 protein, including a recombinant DYRK1 protein, an isolated prolyl hydroxylase (PHD) protein, including a recombinant PHD protein, a tetracycline, receptor activator of nuclear factor kappa-B ligand (RANKL) cytokine, homocysteine, or any combinations thereof.

The present disclosure further includes a composition for preventing or treating an ID2 protein-related disease including an isolated DYRK1 protein, including a recombinant DYRK1 protein, an isolated prolyl hydroxylase (PHD) protein, including a recombinant PHD protein, a tetracycline, receptor activator of nuclear factor kappa-B ligand (RANKL) cytokine, homocysteine, or any combinations thereof. The composition can further include a pharmaceutically acceptable carrier.

BRIEF DESCRIPTION OF THE DRAWINGS

For a more complete understanding of the present invention and its features and advantages, reference is now made to the following description, taken in conjunction with the accompanying drawings, in which like numerals refer to like features, and in which:

FIG. 1A is a schematic diagram for the degradation of HIFα by the DYRK1 kinase and ID2 pathways;

FIG. 1B is a schematic diagram for the stabilization of HIFα by the DYRK1 kinase and ID2 pathways;

FIG. 2A shows chromatographic results specific for the peptide identified as ID2 A3-R8 and phosphorylation of Ser 5; FIG. 2B shows chromatographic results specific for the peptide identified as ID2 K12-R24 and phosphorylation of Ser 14; FIG. 2C shows chromatographic results specific for the peptide identified as ID2 S25-L36 and phosphorylation of Thr 27;

FIG. 3A-3F present data relating to a T27A missense mutation in the ID2 gene in human cancer cells, conservation of the ID2 gene, and characterization of DYRK1's phosphorylation of ID2; FIG. 3A presents sequence analysis results of genomic DNA from the neuroblastoma cell line IMR32 and the wild-type sequence for ID2; FIG. 3B presents sequence analysis of genomic DNA from the colon cancer cell line HRT-18 and the wild type sequence for ID; FIG. 3C presents ID2 wild type sequence data from a variety of organisms; FIG. 3D presents a western blot f the results of an in vitro kinase assay using bacterially expressed GST-ID proteins and recombinant DYRK1A; FIG. 3E presents a western blot of U87 cells transfected with Flag-ID2, Flag-ID2(T27A) or the empty vector were immunoprecipitated, WCL represents whole cellular lysate; FIG. 3F presents a western blot of U87 cells transfected with Flag-ID2 were treated with harmine;

FIG. 4A-4I present data related to the DYRK1-mediated phosphorylation of ID2 at Thr 27 and its effects on neural stem cell (NSC) properties; FIG. 4A is a western blot of lysates of NSCs ID2$^{-/-}$ reconstituted with ID2, the ID2 (T27A) mutant, or an empty vector; FIG. 4B is a set of micropictographs representative of cultures from a neurosphere-forming assay using NSCs with various ID2 genes; FIG. 4C is a graph of the percent of neurospheres generated in serial clonal assays (means of 3 biological replicates±s.d.; *P=0.00883-0.000229 for ID2$^{-/-}$ ID2(T27A) compared with ID2$^{-/-}$ID2(WT)); FIG. 4D is a graph of the cumulative cell number of cultures as in FIG. 4C (means of 3 biological replicates±s.d. *P=<0.0001 for ID2$^{-/-}$ID2(T27A) compared with ID2$^{-/-}$ID2(WT)); FIG. 4E is a western blot to detect phosphorylation of GST-ID2 protein by recombinant DYRK1B in an in vitro kinase assay; FIG. 4F is a western blot of lysates of IMR32 cells to detect phosphorylation of ID2 an ID2(T27A) by DYRK1B; FIG. 4G is a western blot of U87 cell lysates to detect phosphorylation of endogenous ID2 by DYRK1A; FIG. 4H is a western blot of lysates to U87 cells to detect phosphorylation of endogenous ID2 by DYRK1B and kinase inactive GFP-DYRK1B(K140R); FIG. 4I is a western blot of biding between endogenous DYRK1A or DYRK1B and ID2, WCL represents whole cellular lysate;

FIG. 5A-5I present data relating to the DYRK1-ID2-Thr 27 pathway and regulation of controlling GSCs and HIF2α; FIG. 5A shows the effects of phosphorylation of ID2 but not ID2(T27A) by GFP-DYRK1B on HIF2α and SOX2 in GSC #31; FIG. 5B shows in vitro LDA of parallel cultures and effects on frequency of gliomaspheres by DYRK1 when rescued by ID2(T27A); FIG. 5C shows a set of microphotographs of representative cultures of FIG. 5B; FIG. 5D presents the results of serial clonal experiments of cells from FIG. 5B; B; FIG. 5E shows the results of silencing of DYRK1 on phospho-Thr 27 of ID2 and HIF2α in U87 cells; FIG. 5F shows the effects on ubiquitylation of HIF2α is by DYRK1B and reduced by ID2(T27A), as evaluated by in vivo ubiquitylation (left panels, MYC-Ub immunoprecipitation/HA-HIF2α western blot; right panels, whole cellular lysates, WCL); FIG. 5G shows the effects of ID2(T27A) on HIF2α and DYRK1B-mediated reduction of HIF2α during hypoxia; FIG. 5H shows the effects of ID2(T27A) on DYRK1B-mediated decrease of HIF2α half-life during recovery from exposure to $CoCl_2$; FIG. 5I presents quantification of HIF1α protein from FIG. 5H;

FIG. 6A-6I show the effects on DYRK1 kinases and ID2 Thr 27 phosphorylation by hypoxia and PHD1; FIG. 6A shows the effects of hypoxia on phosphorylation of ID2 Thr 27 in GSC #1123; FIG. 6B shows the effects of $CoCl_2$ on DYRK1 kinase; FIG. 6C shows the effects of hypoxia on tyrosine phosphorylation of DYRK1A; FIG. 6D shows the effects of hypoxia on tyrosine phosphorylation of DYRK1B; FIG. 6E shows the effects of $CoCl_2$ on proline hydroxylation of DYRK1A and DYRK1B as shown by anti-hydroxyproline immunoprecipitation in U87 glioma cells (HC, IgG heavy chain; LC, IgG light chain); FIG. 6F shows the interaction of endogenous DYRK1A and DYRK1B with Flag-PHD1 in U87 cells; FIG. 6G shows the interactions of the kinase domain (KD) and the N- or the C-terminal domains of DYRK1B with PHD1 in co-immunoprecipitation assay; FIG. 6H shows the effects of expression of PHD1 on cellular DYRK1 kinase activity in an in vitro phosphorylation assay using recombinant ID2; FIG. 6I shows the effects of expression of PHD1 on DYRK1 kinase activity towards ID2 Thr 27 in vivo;

FIG. 7A-7H show the effects of hypoxia on DYRK1 kinase activity and Thr 27 phosphorylation of ID2; FIG. 7A presents western blots of lysates of U87 glioma cells treated with 100 mM $CoCl_2$ for the indicated times; FIG. 7B shows western blots of lystes of SK—N—SH cells treated with 300 mM CoCl$_2$ for the indicated times; FIG. 7C shows a western blot of lystes of \and stoichiometric evaluation of pThr-27-ID2 in SK—N—SH cells untreated or treated with CoCl$_2$ for 24 h; FIG. 7D shows a western blot of lysates of 293T cells expressing GFP-DYRK1 proteins untreated or treated with 100 mM CoCl$_2$ for 12 h; FIG. 7E shows a western blot of lysates from U251 cells expressing GFP-DYRK1 proteins untreated or treated with of 100 mM CoCl$_2$ for 6 h and immunoprecipitated using GFP antibodies; FIG. 7F shows a western blot of lysates from 293T cells expressing GFP-DYRK1A untreated or treated with 100 mM CoCl$_2$ for 12 h are immunoprecipitates with anti-p-Tyr antibodies; FIG. 7G shows a western blot of lysates from 293T cells expressing GFP-DYRK1B untreated or treated with 100 mM CoCl$_2$ for 12 h and immunoprecipitated with anti-p-Tyr antibodies; FIG. 7H shows western blots of lysates from U87 cells transfected with GFP-DYRK1A, GFP-DYRK1B or GFP and Flag-PHD1, Flag-PHD2, or Flag-PHD3 and immunoprecipitated using anti-hydroxyproline antibody;

FIG. 8A-8L show effect of the DYRK1-ID2 Thr 27 pathway on GSCs and HIF2α; FIG. 8A is a western blot of lystes from GSC #48 cells transduced with lentiviruses expressing ID2-WT, ID2(T27A), or the empty vector; FIG. 8B present analysis by in vitro LDA; FIG. 8C shows the frequency of cells capable of forming gliomaspheres by in vitro LD; FIG. 8D presents a set of microphotographs of representative gliomasphere cultures of cells from FIG. 8A; FIG. 8E presents semi-quantitative RT-PCR analysis of HIF2α mRNAs from cells from FIG. 8A; FIG. 8F presents a western blot of lystes of U87 cells stably expressing Flag-ID2 or Flag-ID2(T27W); FIG. 8G presents a western blot of lysates of GSC #34 cells transduced with lentiviruses expressing DYRK1B-V5 or empty vector; FIG. 8H presents qRT-PCR from cells if FIG. 8G; FIG. 8I presents a western blot of lysates of GSC #31 transduced with lentiviruses expressing DYRK1B-V5 or empty vector; FIG. 8J presents semiquantitative RT-PCR for HIF2α. mRNA; FIG. 8K presents LDA results of GSC #31 cells transduced with lentiviruses expressing DYRK1B and ID2, ID2(T27A), or the empty vector; FIG. 8L presents in vitro LDA results for GSC #31 cells transduced with lentiviruses expressing DYRK1B or the empty vector in the absence or in the presence of undegradable HIF2α (HIF2α-TM).

FIG. 9A-9H show the effects of the DYRK1-ID2-Thr 27 pathway on HIFα stability by regulating the interaction between ID2 and VHL; FIG. 9A is a western blot of U87 cell lysates to show in vivo ubiquitylation of HIF2α protein; FIG. 9B is western blot of lysates of U87 cells co-transfected with plasmids expressing HA-HIF2α and GFP-DYRK1B or GFP-vector; FIG. 9C is a graph of HIF2α protein in cells were treated with 50 mg ml$^{-1}$ of CHX for the indicated times; FIG. 9D is a western blot of lysates of IMR32 cells co-transfected with ID2 and Flag-VHL or Flag-HIF1α expression vectors; FIG. 9E is a western blot of lysates of IMR32 cells transfected with Flag-VHL expression vector and used for IgG or ID2 antibody immunoprecipitation; FIG. 9F is a western blot of Flag immunoprecipitation of binding reactions of in vitro translated Flag-ID and HA-elongin C proteins; FIG. 9G is a western blot of Flag-ID proteins and HA-VHL that were translated and incubated in vitro; FIG. 9H is western blot of an in vitro streptavidin pulldown assay of biotinylated ID2 peptides (amino acid 14-34 WT, pT27, and T27A) and in vitro translated HA-VHL;

FIG. 10A-10K show the effects of unphosphorylated ID2 on the VCB-Cul2 complex; FIG. 10A is a western blot of recombinant ID2 interaction with elongin C and VHL in a GST pulldown assay; FIG. 10B is a western blot of co-immunoprecipitation of VHL and ID2; FIG. 10C is a western blot of the effects of the N terminus of ID2 on the interaction with VHL as determined by immunoprecipitation; FIG. 10D is a western blot of the effects of the N terminus of GST-ID2 is on the interaction with in vitro translated HA-VHL; FIG. 10E is a western blot of the effects of amino acids 154-174 of in vitro translated HA-VHL on interaction with GST-ID2; FIG. 10F is a western blot to detect the effects of phosphorylation of ID2 Thr 27 or the ID2(T27W) mutation on the ID2-VHL interaction as analyzed by in vitro streptavidin pull down of biotinylated ID2 peptides in the presence of recombinant VCB-Cul2; FIG. 10G is a western blot of co-immunoprecipitated proteins to determine the effect of DYRK1B-mediated phosphorylation of ID2 on ID2 interaction with VHL in vivo; FIG. 10H is a western blot showing the effects of in vitro phosphorylation of recombinant ID2 by purified DYRK1B on ID2 interaction with VHL and elongin C in the reconstituted VCB-Cul2 complex; FIG. 10I is a western blot of U87 cell lysates showing the effects of ID2(T27A) on Cul2 in the VCB complex in a co-immunoprecipitation assay; FIG. 10J is a western blot of dissociation of Cul2 from recombinant VCB complex as affected by increasing concentration of purified Flag-ID2; FIG. 10K is a western blot of U87 cell lysate showing the effects of silencing of ID2 on CoCl$_2$-mediated dissociation of Cul2 from VHL as evaluated by Co-IP-WB;

FIG. 11A shows a ribbon representation of the backbone of the VHL-Elongin C complex and the predicted binding conformation of the ID2 peptide; FIG. 11B shows the docking result for the phospho-Thr-27-ID2 peptide shown from the same perspective as FIG. 11A; FIG. 11C shows the complex of FIG. 11A rotated 90 degrees around an axis parallel to the page so that the perspective is from the arrow shown in FIG. 11A; FIG. 11D shows an electrostatic molecular surface representation of the VHL-elongin C complex with the docked ID2 peptide. The perspective is the same as FIG. 11C.

FIG. 12A is a western blot of U87 cell lysates in an in vivo binding assay using lysates from U87 cells co-transfected with HA-VHL and Flag-ID2 or Flag-ID2 (T27E) expression vectors; FIG. 12B is a western blot of U87 lysates from cells were transfected with Flag-ID2, Flag-ID2(T27A) or Flag-ID2(T27E) plasmids; FIG. 12C shows a western blot of in vitro binding between purified Flag-ID2 and His-VHL following in vitro kinase reaction using recombinant DYRK1B and Flag-ID2; FIG. 12D is a western blot of U87 cell lysates in an analysis of the HA-Elongin C immunocomplexes in U87 cells transfected with HA-Elongin C in the absence or presence of Flag-ID2 (T27A); FIG. 12E is a western blot of U87 cell lysates in an analysis of the Flag-SOCS2 immunocomplexes in U87 cells transfected with ID2, ID2(T27A) or the empty vector; FIG. 12F is a western blot of U87 cell lysates and stoichiometric analysis of ID2 and VHL in cellular lysates; FIG. 12G is a western blot of U87 cell lysates showing immunoprecipitation of endogenous VHL in U87 cells in the presence and in the absence of CoCl$_2$.

FIG. 13A is a graph of significant and positive targets of HIF2α that correlate with HIF2α in GBM with high ID2 activity compared to a set of random genes by GSEA; FIG. 13B is a graph of correlations in GBM with low ID2 activity; FIG. 13C is a western blot of U87 cell lystes that shows the effects of inducible expression of DYRK1B in U87 of ID2 Thr 27 phosphorylation and HIF2α; FIG. 13D presents qRT-PCR results from the cells of FIG. 13C; FIG. 13E presents micrographs with immunostaining to show the effects of inducible expression of DYRK1B on HIF2α in subcutaneous xenografts of U87 cells; FIG. 13F is a graph of the effects of inducible expression of DYRK1B on tumor growth inhibition in mice treated as in FIG. 13E; FIG. 13G is a micrograph graph of the effects of expression of DYRK1B WT and DYRK1B(K140R) on orthotopic growth of U87 (haematoxylin & eosin staining of brain cross-sections); FIG. 13H is a graph of a Kaplan-Meier analysis of mice in G (n=7 animals per group); FIG. 13I is a graph of the use of expression of DYRK1A and DYRK1B in predicting survival in GBM patients;

FIG. 14A is a set of micrographs of malignant gliomas; FIG. 14B is a western blot of U87 cell lysates for analysis of DYRK1B in U87 cells stably expressing a doxycycline inducible DYRK1B or the empty vector; FIG. 14C is a micrograph of tissue sections; FIG. 14D is a quantification of BrdU positive cells from FIG. 14C; FIG. 14E is a western blot of U87 cell lysates to analyze ectopically expressed V5-DYRK1B, V5-DYRK1B-K140R; FIG. 14F is a series of immunofluorescence micrographs of brain cross-sections of mice intracranially injected with U87 cells in FIG. 14E;

FIG. 15A is a scatter plot showing the expression of DYRK1A and DYRK1B in GBM; and FIG. 15B is a Kaplan-Meier survival analysis of the prognostic power of the expression of DYRK1A and DYRK1B with the distribution of $\Delta ES_{rand}$, representing the null model, for ID2 activity (left) and ID2 expression (right).

DETAILED DESCRIPTION

Figure 2A:
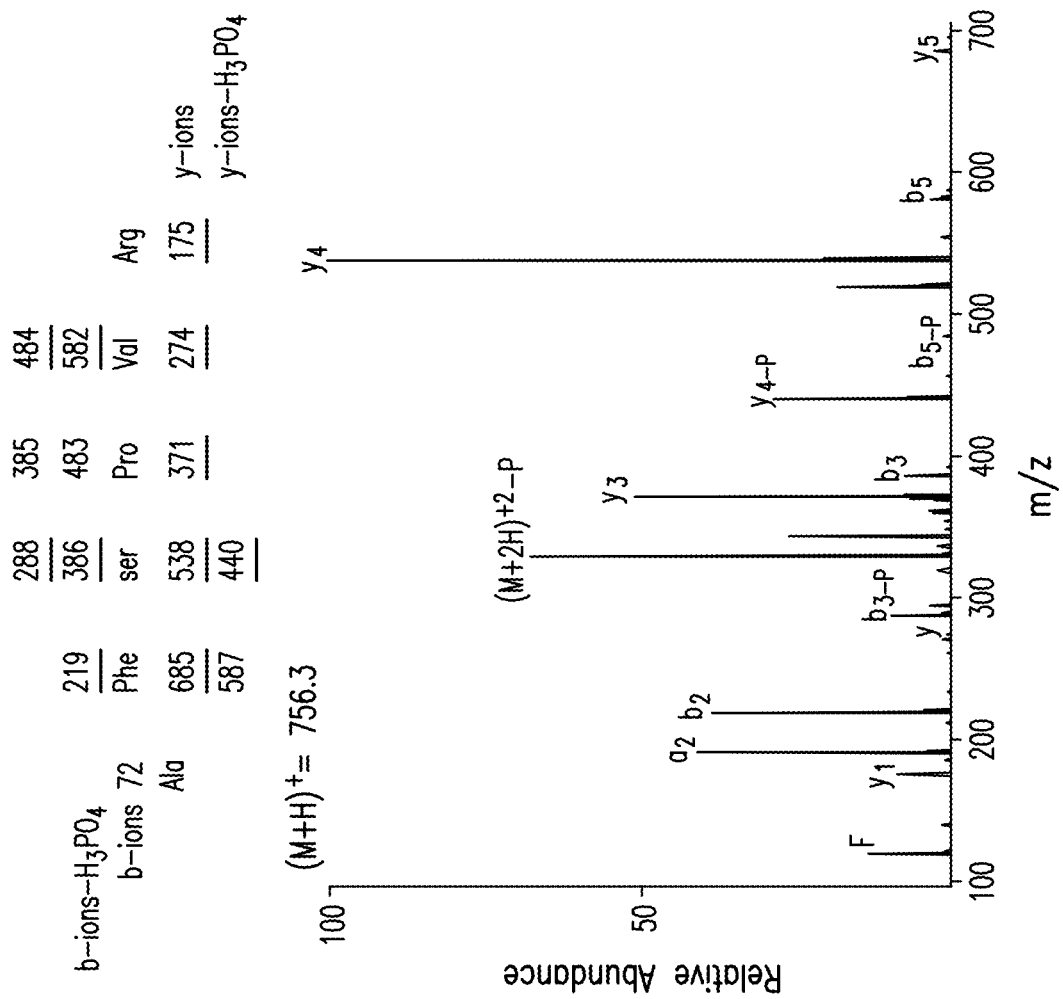
FIG. 2A-2C present chromatographic results of mass spectrometry analysis of ID2 protein immunoprecipitated from IMR32 human neuroblastoma cells.

The present disclosure relates to compositions and methods for regulating the activity of the ID2 protein and for treating an ID protein-related disease, such as a tumor or cancer. The compositions and methods generally operate by regulating the activity of a DYRK1. In particular, the compositions and methods can regulate the phosphorylation of Thr 27 of ID2 by DYRK1.

Although the present disclosure is not limited to the models of FIG. 1A and FIG. 1B, these figures illustrate potential pathways for the interactions of ID2 and DYRK1 and their effects on HIFα stability. It will be understood by one of skill in the art that complete activation and complete inactivation of all proteins of a given type in a cell is uncommon, such that both pathways can be taking place in a given cell at any time. Compositions and methods disclosed herein can simply increase the prevalence of one pathway or a similar pathway over another.

As illustrated in FIG. 1A, HIFα degradation can occur when prolyl hydroxylases (PHD1) are active causing DYRK1 to be phosphorylated (pY) and active. Active DYRK1 phosphorylates ID2 (pT) on Thr 27 of ID2, which has an inhibitory effect. When ID2 is inhibited, the VHL-elongin B (ElgB)-elongin C (ElgC) (VCB)-cullin 2 (Cul2) complex effectively ubiquitinates HIFα, leading to its degradation as a ubiquitinated protein. This pathway can occur in the presence of normal oxygen levels ($pO_2$) and can also be triggered by activating DYRK1 or increasing its expression or by deactivating, downregulating, or decreasing expression of ID2.

As illustrated in FIG. 1B, HIFα stabilization can occur when PHD1 is not active, such that DYRK1 is not phosphorylated and is inactive. Inactive DYRK1 does not phosphorylate ID2 on Thr 27. As a result, ID2 is able to bind directly to VHL and Elg-C, displacing Cul2. A VCB-Cul2 complex is no longer present and HIFα is no longer ubiquitinated. As a result, HIFα is not degraded and is able to accumulate and increase transcription of HIFα target genes. One such target gene is the ID2 gene, setting up a feed-forward ID2-HIFα loop. This pathway can occur in the presence of reduced $pO_2$ and can also be triggered by DYRK1 downregulation or deactivation, ID2 overexpression or activation, and an ID2 mutation that prevents its inhibition by DYRK1, such as mutation at Thr 27, particularly a Thr27Ala mutation.

Human HIFα as used herein can have the sequence provided in Genbank ID: 3091. Human HIF2α as used herein can have the sequence provided in Genbank ID: 2034. Human ID2 as used herein can have the sequence provided in Genbank ID: 3398. Human DYRK1A as used herein can have the sequence provided in Genbank ID: 1859. Human DYRK1B as used herein can have the sequence provided in Genbank ID: 9149. Human VHL as used herein can have the sequence provided in Genbank ID: 7428. Human Elg-B as used herein can have the sequence provided in Genbank ID: 6923. Human Elg-C as used herein can have the sequence provided in Genbank ID: 6921. Human Cul2 as used herein can have the sequence provided in Genbank ID: 8453. Human PHD1 as used herein can have the sequence provided in Genbank ID: 12398. Human PHD2 as used herein can have the sequence provided in Genbank ID: 54583. Human PHD3 as used herein can have the sequence provided in Genbank ID: 112399.

Compositions for Regulating ID2 Activity

The present disclosure provides various compositions that regulate the activity of ID-2 such that HIFα, particularly HIF2α degradation is accelerated in a cell, such as a cancer or tumor cell, or HIFα, particularly HIF2α half-life in a cell, such as a cancer or tumor cell, is decreased as compared to in the absence of such a composition. The compositions function by ultimately increasing the phosphorylation of ID2 on Thr 27.

Increasing the amount or activity of DYRK1 in a cell accelerates the degradation of HIFα and decreases its half-life in the cell. Accordingly, some compositions of the present disclosure include DYRK1, such as biologics containing DYRK1. DYRK1 contained in such compositions can be produced by any suitable method of protein production, such as via culture of a DYRK1-producing cell, including a recombinant cell containing exogenous nucleic acids encoding DYRK1 or increasing its expression.

Other compositions of the present disclosure increase DYRK1 expression in a cell in a patient. These compositions can include exogenous nucleic acids encoding DYRK1 or increasing its expression. Such compositions can be administered to the patient, such as a patient with a cancer or tumor. Such compositions can target delivery of the nucleic acid to cancer or tumor cells or other cells involved in an ID2 protein-related disease.

Other compositions of the present disclosure that increase DYRK1 expression in a cell in a patient can include agents that induce the expression of DYRK1 in the cell. Suitable agents include tetracycline, receptor activator of nuclear factor kappa-B ligand (RANKL) cytokine, homocysteine, and combinations thereof.

Compositions of the present disclosure can further include a PHD, such as PHD1, PHD2, PHD3, and combinations thereof, such as biologics containing a PHD. Increased amounts of PHD can increase phosphorylation and activity of DYRK1. The PHD can be produced by any suitable method of protein production, such as via culture of a PHD-producing cell, including a recombinant cell containing exogenous nucleic acids encoding a PHD or increases the expression of a PHD.

Any of the above compositions for providing DYRK1 to a cell can be present in a combined composition or a combined therapeutic plan in which more than one of the above compositions is administered to the cell in the patient.

The present disclosure further provides for pharmaceutical compositions which include a therapeutic composition as described herein. Such pharmaceutical compositions can further include at least one other agent, such as a stabilizing compound or additional therapeutic agent, and can be administered in any sterile, biocompatible pharmaceutical carrier, including, but not limited to, saline, buffered saline, dextrose, and water. The pharmaceutical compositions can also further include an excipient. The composition can be in a liquid or lyophilized form and includes a diluent (Tris, citrate, acetate or phosphate buffers) having various pH values and ionic strengths, solubilizer such as Tween® or polysorbate, carriers such as human serum albumin or gelatin, preservatives such as thimerosal, parabens, benzylalconium chloride or benzyl alcohol, antioxidants such as ascorbic acid or sodium metabisulfite, and other components such as lysine or glycine. Selection of a particular composition will depend upon a number of factors, including the condition being treated, the route of administration and the pharmacokinetic parameters desired. A more extensive survey of components suitable for pharmaceutical compositions is found in *Remington's Pharmaceutical Sciences*, 18*th* ed. A. R. Gennaro, ed. Mack, Easton, Pa. (1980).

The pharmaceutical compositions of the present invention can be formulated using pharmaceutically acceptable carriers well known in the art in dosages suitable for oral, parenteral, such as intravenous, or topical administration. Such carriers enable the pharmaceutical compositions to be formulated as tablets, pills, capsules, liquids, gels, syrups, slurries, suspensions, enema formulations, stabilized injectable formulations, and the like, for oral, parenteral, such as intravenous, or topical administration to a patient to be treated. Formulations can include, for example, polyethylene glycol, cocoa butter, glycerol, saline, a protein stabilizing agent, a pH control agent, and the like.

Pharmaceutical compositions suitable for use in the present invention include where the active ingredients are contained in an effective amount to achieve the intended purpose. The amount can vary from one individual to another and will depend upon a number of factors.

Single or multiple administrations of formulations can be given depending on the dosage and frequency as required and tolerated by the patient. In certain embodiments, the formulations should provide a sufficient quantity of an active agent to effectively treat and ID2 protein-related disease, such as cancer or a tumor by accelerating HIFα degradation in an affected cell or decreasing HIFα half-life in an affected cell as compared to in the absence of such a composition.

Methods of ID2 Protein-Related Disease Treatment

The present disclosure further relates to methods of treating an ID2 protein-related disease and uses of compositions for treating an ID2 protein-related disease by increasing the degradation of HIFα, particularly HIF2α, in a cell affected by the disease, such as a cancer or tumor cell, or by decreasing HIFα, particularly HIF2α, half-life in a cell affected by the disease, such as a cancer or tumor cell, as compared to an untreated cell. The methods and uses can operate by increasing the phosphorylation of ID2 on Thr 27. The methods and uses can increase the amount or activity of DYRK1 in a cell, such that phosphorylation of ID2 on Thr 27 is increased.

Effects on untreated cells can be estimated from other data and information regarding the ID2 protein-related disease and need not be untreated cells from the same patent administered the composition.

The cell may be located in a patient, who can be a human patient or a non-human patient. A non-human patient can be a mammal or a non-mammal with an anlogof human Tyr 27 in ID2 that regalates VHC-binding based on phosphorylation. In certain embodiments, a non-human can be a dog, a cat, a cow, a horse, a sheep, a goat, or a pig.

The methods or uses can include administering to a patient having an ID2 protein-related disease any composition described herein in any formulation described herein and by any method described herein in an amount and for a time sufficient to increase the degradation of HIFα, particularly HIF2α, in a cell affected by the disease, such as a cancer or tumor cell, decrease HIFα, particularly HIF2α, half-life in a cell affected by the disease, such as a cancer or tumor cell, as compared to an untreated cell, increase the phosphorylation of ID2 on Thr 27 in a cell affected by the disease, such as a cancer or tumor cell, as compared to an untreated cell, or increase the amount or activity of DYRK1 in a cell affected by the disease, such as a cancer or tumor cell, as compared to an untreated cell.

The methods or uses can include oral, parenteral, such as intravenous, or topical administration.

The methods or uses can prevent or treat and ID2 protein-related disease and can achieve a more favorable outcome for the patient than if the method or use were not employed. In the preventative context, the method or use can delay or prevent the onset of one or more symptoms of an ID2 protein-related disease for at least a set period of time. In the treatment context, the method or use can delay or prevent the progression of one or more symptoms of an ID2 protein-related disease for at least a set period time, cause a regression of one or more symptoms of an ID2 protein-related disease for at least a set period of time, and/or cause the disappearance of one or more symptoms of and ID2 protein-related disease for at least a set period of time. In each instance described above the set period of time can be at least one month, at least one year, at least five years, or at least ten years.

Methods or uses described herein can be used to treat cancer, a tumor, metabolic diseases, vascular diseases, neurodegenerative diseases, and/or renal diseases. In particular, methods and uses described herein can be used to treat gliomas, particularly malignant gliomas, such as a glioblastoma. The methods and uses described herein can also be used to treat a retinoblastoma, a ewings sarcoma, or a lymphoma. In particular, methods and uses described herein can be used to treat Alzheimer's disease.

In one example method or use increased phosphorylation of ID2 can occur via activation of DYRK1. Such phosphorylated ID2 can disassociate from the VHL ubiquitin ligase complex, increasing the binding of cullin 2 to VHL, and thereby increasing the ubiquitylation and degradation of HIF2α.

In another example method or use, a composition containing one or more DYRK1 activator can be used to increase phosphorylation of ID2, thereby restraining ID2 activity and increasing the ubiquitylation and degradation of HIF2α. Such activators can be selected from: prolyl hydroxylases (PHDs), tetracycline, receptor activator of nuclear factor kappa-B ligand (RANKL) cytokine, homocysteine, nucleic acids encoding DYRK1, and combinations thereof. DYRK1 protein can also be administered, as can reagents useful to increase the expression of DYRK1.

In certain embodiments, the methods and uses can involve deletion of the Id1 and Id2 genes in malignant glioma to result in a marked reduction of HIF2α protein. Accordingly, deletion of said genes or inactivation, e.g., via RNAi or other methods known in the art, of the genes can be employed to regulate the degradation of HIF2α. Tetracycline-induced expression of DYRK1B at levels comparable to normal brain can downregulates HIF2α in cells, such as, but not limited to, glioma cells, and can reduce HIF2α targets that promote stem cell functions. Expression of DYRK1B can also inhibit tumor cell proliferation in vivo, resulting in tumor reduction. Increasing the expression of wild-type DYRK1B in cells, such as, but not limited to glioma cells, can significantly increases survival and tumor latency.

EXAMPLES

The presently disclosed subject matter will be better understood by reference to the following Examples, which are provided as exemplary of the invention, and not by way of limitation.

Example 1: Materials and Methods

The following materials and methods were used throughout the following Examples.

Plasmids, Cloning and Lentivirus Production

A constitutively stabilized mutant of HIF2α (HIF2α-TM) was as described in Warnecke, C. et al. Differentiating the functional role of hypoxia-inducible factor (HIF)-1α and HIF-2α (EPAS-1) by the use of RNA interference: erythropoietin is a HIF-2α target gene in Hep3B and Kelly cells. FASEB J. 18, 1462-1464 (2004). The HIF2α-TM (triple mutant) construct harbored the following mutations in the prolyl and asparagyl hydroxylation sites: P405A, P530G and N851A. Polypeptide fragments of DYRK1B were cloned into pcDNA3-HA and included DYRK1B N terminus, N-Ter (amino acids 1-110), DYRK1B kinase domain, KD (amino acids 111-431), and DYRK1B C terminus, C-Ter (amino acids 432-629). cDNAs for RBX1, elongin B and Elongin C were provided by Michele Pagano (New York University) and cloned into the pcDNA vector by PCR. HA-tagged HIF1α and HIF2α were obtained from Addgene. GFP-tagged DYRK1A and DYRK1B were cloned into pcDNA vector. pcDNA-HA-VHL was provided by Kook Hwan Kim (Sungkyunkwan University School of Medicine, Korea). Site-directed mutagenesis was performed using QuickChange or QuickChange Multi Site-Directed mutagenesis kit (Agilent) and resulting plasmids were sequence verified. Lentivirus was generated by co-transfection of the lentiviral vectors with pCMV-ΔR8.1 and pMD2.G plasmids into HEK293T cells as described in Niola, F. et al. Mesenchymal high-grade glioma is maintained by the ID-RAP1 axis. J. Clin. Invest. 123, 405-417 (2013) and Carro, M. S. et al. The transcriptional network for mesenchymal transformation of brain tumors. Nature 463, 318-325 (2010).

ShRNA sequences were:

```
ID2-1:
GCCTACTGAATGCTGTGTATACTCGAGTATACACAGCATTCAGTAGGC;

ID2-2:
CCCACTATTGTCAGCCTGCATCTCGAGATGCAGGCTGACAATAGTGGG;

DYRK1A:
CAGGTTGTAAAGGCATATGATCTCGAGATCATATGCCTTTACAACCTG;

DYRK1B:
GACCTACAAGCACATCAATGACTCGAGTCATTGATGTGCTTGTAGGTC.
```

Cell Culture and Hypoxia Induction

IMR-32 (ATCC CCL-127), SK—N—SH (ATCC HTB-11), U87 (ATCC HTB-14), NCI-H1299 (ATCC CRL-5803), HRT18 (ATCC CCL-244), and HEK293T (ATCC CRL-11268) cell lines were acquired through American Type Culture Collection. U251 (Sigma, catalogue number 09063001) cell line was obtained through Sigma. Cell lines were cultured in DMEM supplemented with 10% fetal bovine serum (FBS, Sigma). Cells were routinely tested for mycoplasma contamination using Mycoplasma Plus PCR Primer Set (Agilent, Santa Clara, Calif.) and were found to be negative. Cells were transfected with Lipofectamine 2000 (Invitrogen) or calcium phosphate. Mouse NSCs were grown in Neurocult medium (StemCell Technologies) containing 1× proliferation supplements (StemCell Technologies), and recombinant FGF-2 and EGF (20 ng ml$^{-1}$ each; Peprotech). GBM-derived glioma stem cells were obtained by de-identified brain tumor specimens from excess material collected for clinical purposes at New York Presbyterian-Columbia University Medical Center. Donors (patients diagnosed with glioblastoma) were anonymous. Progressive numbers were used to label specimens coded in order to preserve the confidentiality of the subjects. Work with these materials was designated as IRB exempt under paragraph 4 and it is covered under IRB protocol #IRB-AAAI7305. GBM-derived GSCs were grown in DMEM:F12 containing 1×N2 and B27 supplements (Invitrogen) and human recombinant FGF-2 and EGF (20 ng m=l$^{-1}$ each; Peprotech). Cells at passage (P) 4 were transduced using lentiviral particle in medium containing 4 ∝g ml$^{-1}$ of polybrene (Sigma). Cells were cultured in hypoxic chamber with 1% $O_2$ ($O_2$ Control Glove Box, Coy Laboratory Products, MI) for the indicated times or treated with a final concentration of 100-300 ∝M of $CoCl_2$ (Sigma) as specified in figure legends.

Mouse neurosphere assay was performed by plating 2,000 cells in 35 mm dishes in collagen containing NSC medium to ensure that distinct colonies were derived from single cells and therefore clonal in origin as described in Reynolds, B. A. & Weiss, S. Clonal and population analyses demonstrate that an EGF-responsive mammalian embryonic CNS precursor is a stem cell. Dev. Biol. 175, 1-13 (1996). Neurosphere formation was observed over serial clonal passages in limiting dilution semi-solid cultures and the cell expansion rate over passages, which is a direct indication of self-renewing symmetric cell divisions as described in Deleyrolle, L. P. et al. Determination of somatic and cancer stem cell self-renewing symmetric division rate using sphere assays. PLoS One. 6, e15844 (2011).

For serial sub-culturing neurospheres were mechanically dissociated into single cells in bulk and re-cultured them under the same conditions for six passages. The number of spheres was scored after 14 days. Only colonies >100 ∝m in diameter were counted as spheres. Neurosphere size was determined by measuring the diameters of individual neurospheres under light microscopy. Data are presented as percent of neurospheres obtained at each passage (number of neurospheres scored/number of NSCs plated×100) in three independent experiments. P value was calculated using a multiple t-test with Holm-Sidak correction for multiple comparisons. To determine the expansion rate, 10,000 cells were plated from 3 independent P1 clonal assays in 35 mm dishes and scored the number of viable cells after 7 days by Trypan Blue exclusion. Expansion rate of NSCs was determined using a linear regression model and difference in the slopes (P value) was determined by the analysis of covariance (ANCOVA) using Prism 6.0 (GraphPad). Limiting dilution assay for human GSCs was performed as described in Tropepe, V. et al. Distinct neural stem cells proliferate in response to EGF and FGF in the developing mouse telencephalon. Dev. Biol. 208, 166-188 (1999). Briefly, spheres were dissociated into single cells and plated into 96-well plates in 0.2 ml of medium containing growth factors at increasing densities (1-100 cells per well) in triplicate. Cultures were left undisturbed for 14 days, and then the percent of wells not containing spheres for each cell dilution was calculated and plotted against the number of cells per well. Linear regression lines were plotted, and the minimal frequency of glioma cells endowed with stem cell capacity was estimated (the number of cells required to generate at least one sphere in every well=the stem cell frequency) based on the Poisson distribution and the intersection at the 37% level using Prism 6.0 software. Data represent the means of three independent experiments performed in different days for the evaluation of the effects of ID2, ID2 (T27A) in the presence or in the absence of DYRK1B. LDA for the undegradable HIF2α rescue experiment was performed by using three cultures transduced independently on the same day.

Identification of Phosphorylation Sites of ID2

Figure 2B:
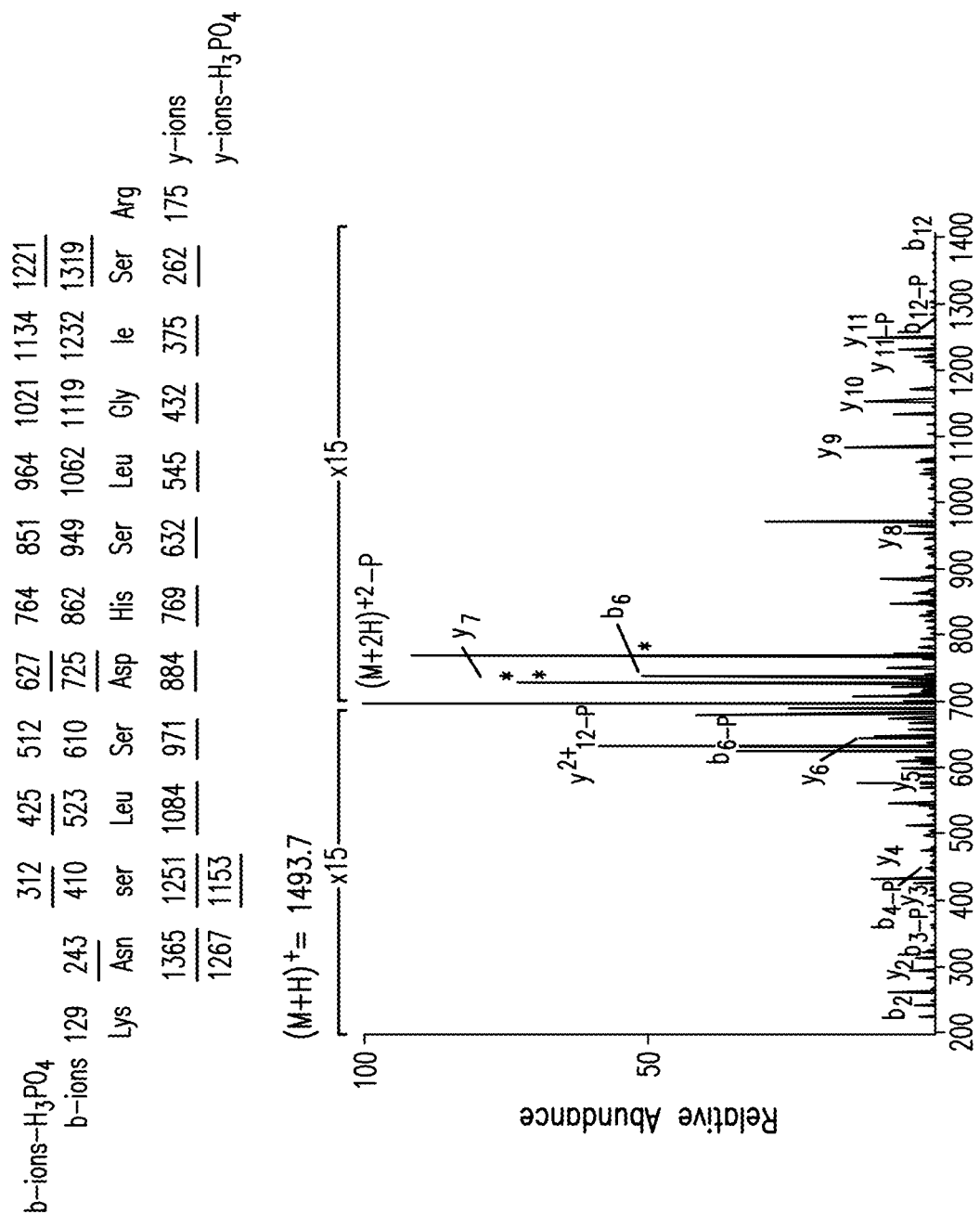
Figure 2C:
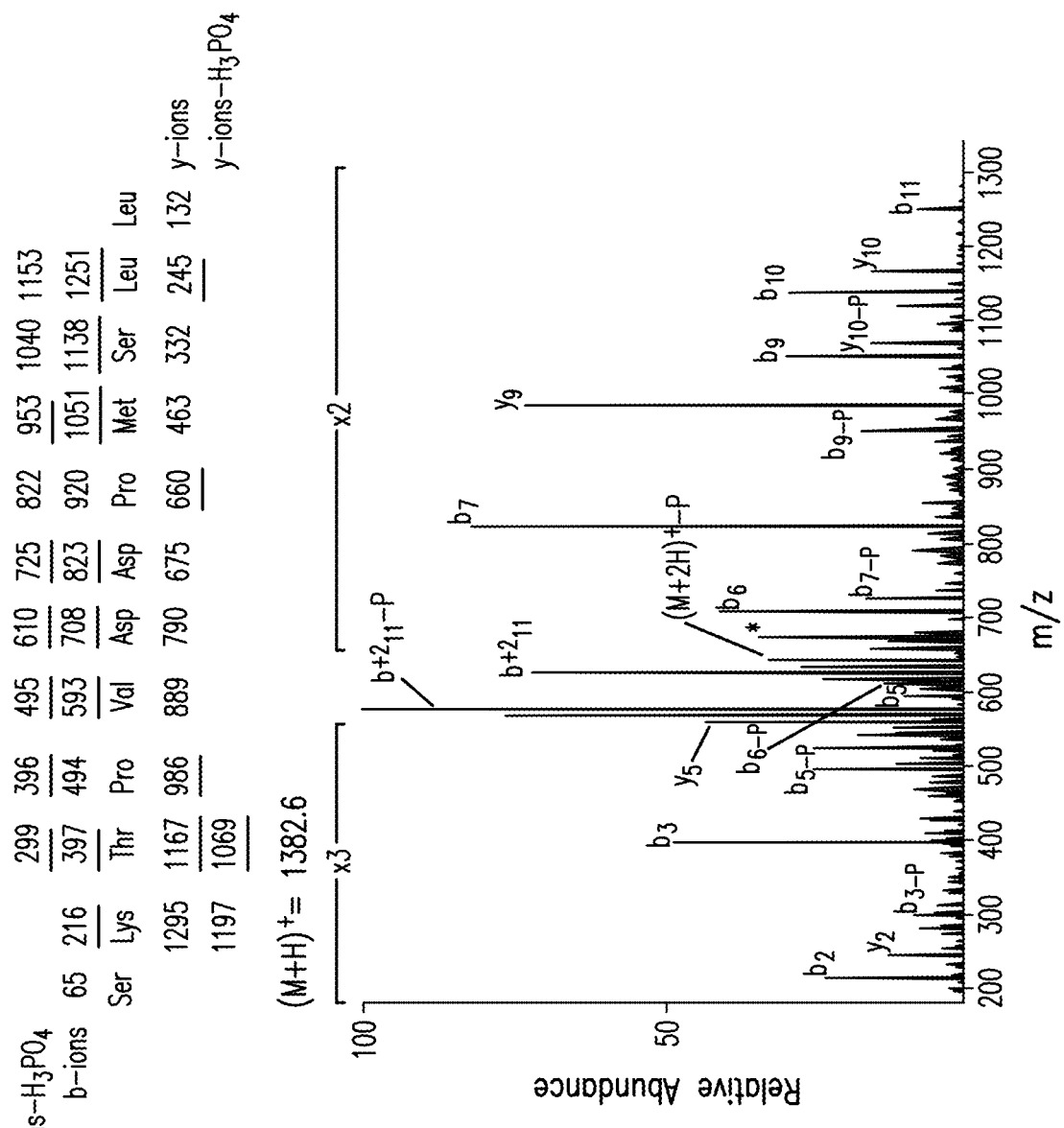

To identify the sites of ID2 phosphorylation from IMR32 human neuroblastoma cells, the immunoprecipitated ID2 protein was excised, digested with trypsin, chymotrypsin and Lys-C and the peptides extracted from the polyacrylamide in two 30 µl aliquots of 50% acetonitrile/5% formic acid. These extracts were combined and evaporated to 25 µl for MS analysis. The LC-MS system consisted of a state-of-the-art Finnigan LTQ-FT mass spectrometer system with a Protana nanospray ion source interfaced to a self-packed 8 cm×75 µm id Phenomenex Jupiter 10 µm C18 reversed-phase capillary column. 0.5-5 µl volumes of the extract were injected and the peptides eluted from the column by an acetonitrile/0.1 M acetic acid gradient at a flow rate of 0.25 µl min-1. The nanospray ion source was operated at 2.8 kV. The digest was analysed using the double play capability of the instrument acquiring full scan mass spectra to determine peptide molecular weights and product ion spectra to determine amino acid sequence in sequential scans. This mode of analysis produced approximately 1200 CAD spectra of ions ranging in abundance over several orders of magnitude. Tandem MS/MS experiments were performed on each candidate phosphopeptide to verify its sequence and locate the phosphorylation site. A signature of a phosphopeptide is the detection of loss of 98 daltons (the mass of phosphoric acid) in the MS/MS spectrum. With this method, three phosphopeptides were found to carry phosphorylations at residues Ser 5, Ser 14 and Thr 27 of the ID2 protein. (FIG. 2A, FIG. 2B and FIG. 2C.)

Generation of Phospho-ID2-T27 Antibody

The anti-phospho-T27-ID2 antibody was generated by immunizing rabbits with a short synthetic peptide containing the phosphorylated T27 (CGISRSK-pT-PVDDPMS) (Yenzym Antibodies, LLC). A two-step purification process was applied. First, antiserum was cross-absorbed against the phospho-peptide matrix to purify antibodies that recognize the phosphorylated peptide. Then, the anti-serum was purified against the un-phosphorylated peptide matrix to remove non-specific antibodies.

Immunoblot, Immunoprecipitation and In Vitro Binding Assay

Cells were lysed in NP40 lysis buffer (50 mM Tris-HCl, pH 7.5, 150 mM NaCl, 1 mM EDTA, 1% NP40, 1.5 mM Na3VO4, 50 mM sodium fluoride, 10 mM sodium pyrophosphate, 10 mM β-glycerolphosphate and EDTA-free protease inhibitor cocktail (Roche)) or RIPA buffer (50 mM Tris-HCl, pH 7.5, 150 mM NaCl, 1 mM EDTA, 1% NP40, 0.5% sodium dexoycholate, 0.1% sodium dodecyl sulphate, 1.5 mM Na3VO4, 50 mM sodium fluoride, 10 mM sodium pyrophosphate, 10 mM β-glycerolphosphate and EDTA-free protease inhibitor cocktail (Roche)). Lysates were cleared by centrifugation at 15,000 r.p.m. for 15 min at 4° C. For immunoprecipitation, cell lysates were incubated with primary antibody (hydroxyproline, Abcam, ab37067; VHL, BD, 556347; DYRK1A, Cell Signaling Technology, 2771; DYRK1B, Cell Signaling Technology, 5672) and protein G/A beads (Santa Cruz, sc-2003) or phospho-Tyrosine (P-Tyr-100) Sepharose beads (Cell Signaling Technology, 9419), HA affinity matrix (Roche, 11815016001), Flag M2 affinity gel (Sigma, F2426) at 4° C. overnight. Beads were washed with lysis buffer four times and eluted in 2×SDS sample buffer. Protein samples were separated by SDS-PAGE and transferred to polyvinyl difluoride (PVDF) or nitrocellulose (NC) membrane. Membranes were blocked in TBS with 5% non-fat milk and 0.1% Tween20, and probed with primary antibodies. Antibodies and working concentrations are: ID2 1:500 (C-20, sc-489), GFP 1:1,000 (B-2, sc-9996), HIF2α/EPAS-1 1:250 (190b, sc-13596), c-MYC (9E10, sc-40), and elongin B 1:1,000 (FL-118, sc-11447), obtained from Santa Cruz Biotechnology; phospho-Tyrosine 1:1,000 (P-Tyr-100, #9411), HA 1:1,000 (C29F4, 3724), VHL 1:500 (2738), DYRK1A 1:1,000, 2771; DYRK1B 1:1,000, 5672) and RBX1 1:2,000 (D3J5I, 11922), obtained from Cell Signaling Technology; VHL 1:500 (GeneTex, GTX101087); β-actin 1:8000 (A5441), α-tubulin 1:8,000 (T5168), and Flag M2 1:500 (F1804) obtained from Sigma; HIF1α 1:500 (H1alpha67, NB100-105) and elongin C 1:1, 000 (NB100-78353) obtained from Novus Biologicals; HA 1:1000 (3F10, 12158167001) obtained from Roche. Secondary antibodies horseradish-peroxidase-conjugated were purchased from Pierce and ECL solution (Amersham) was used for detection.

For in vitro binding assays, HA-tagged RBX1, elongin B, elongin C and VHL were in vitro translated using TNT quick coupled transcription/translation system (Promega). Active VHL protein complex was purchased from EMD Millipore. Purified His-VHL protein was purchased from ProteinOne (Rockville, Md.). GST and GST-ID2 proteins were bacterial expressed and purified using glutathione sepharose beads (GE healthcare life science). Active DYRK1B (Invitrogen) was used for in vitro phosphorylation of Flag-ID2 proteins. Biotinylated WT and modified (pT27 and T27W) ID2 peptides (amino acids 14-34) were synthesized by LifeTein (Somerset, N.J.). In vitro binding experiments between ID2 and VCB-Cul2 were performed using 500 ng of Flag-ID2 and 500 ng of VCB-Cul2 complex or 500 ng VHL protein in binding buffer (50 mM Tris-Cl, pH 7.5, 100 mM NaCl, 1 mM EDTA, 10 mM β-glycerophosphate, 10 mM sodium pyrophosphate, 50 mM sodium fluoride, 1.5 mM Na3VO4, 0.2% NP40, 10% glycerol, 0.1 mg ml-1 BSA and EDTA-free protease inhibitor cocktail (Roche)] at 4° C. for 3 h. In vitro binding between ID2 peptides and purified proteins was performed using 2 μg of ID2 peptides and 200 ng of recombinant VCB-Cul2 complex or 200 ng recombinant VHL in binding buffer (50 mM Tris-C1, pH 7.5, 100 mM NaCl, 1 mM EDTA, 10 mM β-glycerophsphate, 10 mM sodium pyrophosphate, 50 mM sodium fluoride, 1.5 mM Na3VO4, 0.4% NP40, 10% glycerol, 0.1 mg ml-1 BSA and EDTA-free protease inhibitor cocktail (Roche)) at 4° C. for 3 h or overnight. Protein complexes were pulled down using glutathione sepharose beads (GE Healthcare Life Science) or streptavidin conjugated beads (Thermo Fisher Scientific) and analysed by immunoblot.

In Vitro and In Vivo Kinase Assays

Cdk1, Cdk5, DYRK1A, DYRK1B, ERK, GSK3, PKA, CaMKII, Chk1, Chk2, RSK-1, RSK-2, aurora-A, aurora-B, PLK-1, PLK-2, and NEK2 were all purchased from Life Technology and ATM from EMD Millipore. The 18 protein kinases tested in the survey were selected because they are proline-directed S/T kinases (Cdk1, Cdk5, DYRK1A, DYRK1B, ERK) and/or because they were considered to be candidate kinases for Thr 27, Ser 14 or Ser 5 from kinase consensus prediction algorithms (NetPhosK1.0, www.cbs.dtu.dk/services/NetPhosK/; GPS Version 3.0 gps-.biocuckoo.org/#) or visual inspection of the flanking regions and review of the literature for consensus kinase phosphorylation motifs. 1 μg of bacterially purified GST-ID substrates were incubated with 10-20 ng each of the recombinant active kinases. The reaction mixture included 10 μCi of [γ-$^{32}$P]ATP (PerkinElmer Life Sciences) in 50 μl of kinase buffer (25 mM Tris-HCl, pH 7.5, 5 mM β-glycerophosphate, 2 mM dithiothreitol (DTT), 0.1 mM Na3VO4, 10 mM MgCl2, and 0.2 mM ATP). Reactions were incubated at 30° C. for 30 min. Reactions were terminated by addition of Laemmli SDS sample buffer and boiling on 95° C. for 5 min. Proteins were separated on SDS-PAGE gel and phosphorylation of proteins was visualized by autoradiography. Coomassie staining was used to document the amount of substrates included in the kinase reaction. In vitro phosphorylation of Flag-ID2 proteins by DYRK1B (Invitrogen) was performed using 500 ng of GST-DYRK1B and 200 ng of bacterially expressed purified Flag-ID2 protein.

In vivo kinase assay in GSCs and glioma cells was performed using endogenous or exogenously expressed DYRK1A and DYRK1B. Cell lysates were prepared in lysis buffer (50 mM Tris-HCl, pH 7.5, 150 mM NaCl, 1 mM EDTA, 1% NP40, 1.5 mM Na3VO4, 50 mM sodium fluoride, 10 mM sodium pyrophosphate, 10 mM β-glycerolphosphate and EDTA-free protease inhibitor cocktail (Roche)). DYRK1 kinases were immunoprecipitated using DYRK1A and DYRK1B antibodies (for endogenous DYRK1 proteins) or GFP antibody (for exogenous GFP-DYRK1 proteins) from 1 mg cellular lysates at 4° C. Immunoprecipitates were washed with lysis buffer four times followed by two washes in kinase buffer as described above and incubated with 200 ng purified Flag-ID2 protein in kinase buffer for 30 min at 30° C. Kinase reactions were separated by SDS-PAGE and analysed by western blot using p-T27-ID2 antibody.

Protein Half-Life and Stoichiometry

HIF2α half-life was quantified using ImageJ processing software (NIH). Densitometry values were analysed by Prism 6.0 using the linear regression function. Stoichiometric quantification of ID2 and VHL in U87 cells was obtained using recombinant Flag-ID2 and His-tagged-VHL as references. The chemiluminescent signal of serial dilutions of the recombinant proteins was quantified using ImageJ, plotted to generate a linear standard curve against which the densitometric signal generated by serial dilutions of cellular lysates (1×10$^6$ U87 cells) was calculated. Triplicate values±s.e.m. were used to estimate the ID2:VHL ratio per cell. The stoichiometry of pT27-ID2 phosphorylation was determined as described in Mîinea, C. P. & Lienhard, G. E. Stoichiometry of site-specific protein phosphorylation estimated with phosphopeptide-specific antibodies. Biotechniques 34, 828-831 (2003). Briefly, SK—N—SH cells were plated at density of 1×10$^6$ in 100 mm dishes. Forty-eight hours later 1.5 mg of cellular lysates from cells untreated or treated with CoCl2 during the previous 24 h were prepared in RIPA buffer and immunoprecipitated using 4 μg of pT27-ID2 antibody or rabbit IgG overnight at 4° C. Immune complexes were collected with TrueBlot anti-rabbit IgG beads (Rockland), washed 5 times in lysis buffer, and eluted in SDS sample buffer. Serial dilutions of cellular lysates, IgG and pT27-ID2 immunoprecipitates were loaded as duplicate series for SDS-PAGE and western blot analysis using ID2 or p-T27-ID2 antibodies. Densitometry quantification of the chemiluminescent signals was used to determine (1) the efficiency of the immunoprecipitation using the antibody against p-ID2-T27 and (2) the ratio between efficiency of the immunoprecipitation evaluated by western blot for p-T27-ID2 and total ID2 antibodies. This represented the percent of phosphorylated Thr 27 of ID2 present in the cell preparation.

Identification of ID2 Complexes by Mass Spectrometry

Cellular ID2 complexes were purified from the cell line NCI-H1299 stably engineered to express Flag-HA-ID2. Cellular lysates were prepared in 50 mM Tris-HCl, 250 mM NaCl, 0.2% NP40, 1 mM EDTA, 10% glycerol, protease and phosphatase inhibitors. Flag-HA-ID2 immunoprecipitates were recovered first with anti-Flag antibody-conjugated M2 agarose (Sigma) and washed with lysis buffer containing 300 mM NaCl and 0.3% NP40. Bound polypeptides were eluted with Flag peptide and further affinity purified by anti-HA antibody-conjugated agarose (Roche). The eluates from the HA beads were analysed directly on long gradient reverse phase LC-MS/MS. A specificity score of proteins interacting with ID2 was computed for each polypeptide by comparing the number of peptides identified from our mass spectrometry analysis to those reported in the CRAPome database that includes a list of potential contaminants from affinity purification-mass spectrometry experiments (<<http://www.crapome.org>>as accessed January, 2016). The specificity score was computed as [(#peptide*#xcorr)/ (AveSC*MaxSC*# of Expt.)], #peptide, identified peptide count; #xcorr, the cross-correlation score for all candidate peptides queried from the database; AveSC, averaged spectral counts from CRAPome; MaxSC, maximal spectral counts from CRAPome; and # of Expt., the total found number of experiments from CRAPome.

Ubiquitiylation Assay

U87 cells were transfected with pcDNA3-HA-HIFα (HIF1α or HIF2α), pcDNA3-Flag-ID2 (WT or T27A), pEGFP-DYRK1B and pcDNA3-Myc-Ubiquitin. 36 h after transfection, cells were treated with 20 μM MG132 (EMD Millipore) for 6 h. After washing with ice-cold PBS twice, cells were lysed in 100 μl of 50 mM Tris-HCl pH 8.0, 150 mM NaCl (TBS) containing 2% SDS and boiled at 100° C. for 10 min. Lysates were diluted with 900 μl of TBS containing 1% NP40 Immunoprecipitation was performed using 1 mg of cellular lysates. U biquitylated proteins were immunoprecipitated using anti-Myc antibody and analysed by western blot using HA antibody.

Docking of ID2 Peptide to the VCB Complex

A highly accurate flexible peptide docking method implemented in ICM software (Molsoft LLC, La Jolla Calif.) was used to dock ID2 peptides to VCB or components thereof as described in Bordner, A. J. & Abagyan, R. Ab initio prediction of peptide-MHC binding geometry for diverse class I MHC allotypes. Proteins 63, 512-526 (2006). A series of overlapping peptides of varying lengths were docked to the complex of VHL and elongin C (EloC), or VHL or EloC alone, from the crystallographic structure of the VHL-CRL ligase (Nguyen, H. C., Yang, H., Fribourgh, J. L., Wolfe, L. S. & Xiong, Y. Insights into Cullin-RING E3 ubiquitin ligase recruitment: structure of the VHL-EloBC-Cul2 complex. Structure 23, 441-449 (2015)). Briefly, an all-atom model of the peptide was docked into grid potentials derived from the X-ray structure using a stochastic global optimization in internal coordinates with pseudo-Brownian and collective 'probability-biased' random moves as implemented in the ICM program. Five types of potentials for the peptide-receptor interaction energy—hydrogen van der Waals, non-hydrogen van der Waals, hydrogen bonding, hydrophobicity and electrostatics—were precomputed on a rectilinear grid with 0.5 Å spacing that fills a 34 Å×34 Å×25 Å box containing the VHL-EloC (V-C) complex, to which the peptide was docked by searching its full conformational space within the space of the grid potentials. The preferred docking conformation was identified by the lowest energy conformation in the search. The preferred peptide was identified by its maximal contact surface area with the respective receptor.

Ab initio folding and analysis of the peptides was performed as previously described in Abagyan, R. & Totrov, M. Biased probability Monte Carlo conformational searches and electrostatic calculations for peptides and proteins. J. Mol. Biol. 235, 983-1002 (1994) and Almond, D. & Cardozo, T. Assessment of immunologically relevant dynamic tertiary structural features of the HIV-1 V3 loop crown R2 sequence by ab initio folding. J. Vis. Exp. 43, 2118 (2010). Ab initio folding of the ID2 peptide and its phospho-T27 mutant showed that both strongly prefer an α-helical conformation free (unbound) in solution, with the phospho-T27 mutant having a calculated free energy almost 50 kcal-equivalent units lower than the unmodified peptide.

RT-PCR

Total RNA was prepared with Trizol reagent (Invitrogen) and cDNA was synthesized using SuperScript II Reverse Transcriptase (Invitrogen) as described in Warnecke, C. et al. Differentiating the functional role of hypoxia-inducible factor (HIF)-1α and HIF-2α (EPAS-1) by the use of RNA interference: erythropoietin is a HIF-2α target gene in Hep3B and Kelly cells. FASEB J. 18, 1462-1464 (2004) and Zhao, X. et al. The HECT-domain ubiquitin ligase Huwel controls neural differentiation and proliferation by destabilizing the N-Myc oncoprotein. Nature Cell Biol. 10, 643-653 (2008).

Semi-quantitative RT-PCR was performed using AccuPrime Taq DNA polymerase (Invitrogen) and the following primers: for HIF2A Fw 5'_GTGCTCCCACGGCCTGTA_3' and Rv 5'_TTGTCACACCTATGGCATATCACA_3'; GAPDH Fw 5'_AGAAGGCTGGGGCTCATTTG_3' and Rv 5'_AGGGGCCATCCACAGTCTTC_3'. The quantitative RT-PCR was performed with a Roche480 thermal cycler, using SYBR Green PCR Master Mix from Applied Biosystem.

Primers used in qRT-PCR are: SOX2 Fw 5'_TTGCTGCCTCTTTAAGACTAGGA_3' and Rv 5'_CTGGGGCTCAAACTTCTCTC_3'; NANOG Fw 5'_ATGCCTCACACGGAGA CTGT_3' and Rv 5'_AAGTGGGTTGTTTGCCTTTG_3'; POU5F1 Fw 5'_GTGGAGG AAGCTGACAACAA_3' and Rv 5'_ATTCTCCAGGTTGCCTCTCA_3' FLT1 Fw 5'_AG CCCATAAATGGTCTTTGC_3' and Rv 5'_GTGGTTTGCTTGAGCTGTGT_3'; PIK3CA Fw 5'_TGCAAAGAATCAGAACAATGCC_3' and 5'_CACGGAGGCATTCTAAAGTCA_3'; BMI1 Fw 5'_AATCCCCACCTGATGTGTGT_3' and Rv 5'_GCTGGTCTCCAGGTAACGAA_3'; GAPDH Fw 5'_GAAGGTGAAGGTCGGAGTCAAC_3' and Rv 5'_CAG AGTTAAAAGCAGCCCTGGT_3'; 18S Fw 5'_CGCCGCTAGAGGTGAAATTC_3' and Rv 5'_CTTTCGCTCTGGTCCGTCTT_3'. The relative amount of specific mRNA was normalized to 18S or GAPDH. Results are presented as the mean±s.d. of three independent experiments each performed in triplicate (n=9). Statistical significance was determined by Student's t-test (two-tailed) using GraphPad Prism 6.0 software.

Subcutaneous and Intracranial Xentografr Glioma Models

Mice were housed in pathogen-free animal facility. All animal studies were approved by the IACUC at Columbia University (numbers AAAE9252; AAAE9956). Mice were 4-6-week-old male athymic nude (Nu/Nu, Charles River Laboratories). No statistical method was used to pre-determine sample size. No method of randomization was used to allocate animals to experimental groups. Mice in the same cage were generally part of the same treatment. The investigators were not blinded during outcome assessment. In none of the experiments did tumours exceed the maximum volume allowed according to our IACUC protocol, specifically 20 mm in the maximum diameter. 2×10$^5$ U87 cells stably expressing a doxycycline inducible lentiviral vector coding for DYRK1B or the empty vector were injected subcutaneously in the right flank in 100 μl volume of saline solution (7 mice per each group). Mice carrying 150-220 mm$^3$ subcutaneous tumours (21 days from injection) generated by cells transduced with DYRK1B were treated with vehicle or doxycycline by oral gavage (Vibramycin, Pfizer Labs; 8 mg ml-1, 0.2 ml/day as described in Cawthorne, C., Swindell, R., Stratford, I. J., Dive, C. & Welman, A. Comparison of doxycycline delivery methods for Tet-inducible gene expression in a subcutaneous xenograft model. J. Biomol. Tech. 18, 120-123 (2007); mice carrying tumours generated by cells transduced with the empty vector were also fed with doxycycline. Tumour diameters were measured daily with a caliper and tumour volumes estimated using the formula: width$^2$×length/2=V (mm$^3$). Mice were euthanized after 5 days of doxycycline treatment. Tumours were dissected and fixed in formalin for immunohistochemical analysis. Data are means±s.d. of 7 mice in each group. Statistical significance was determined by ANCOVA using GraphPad Prism 6.0 software package (GraphPad).

Orthotopic implantation of glioma cells was performed as described in Warnecke, C. et al. Differentiating the functional role of hypoxia-inducible factor (HIF)-1α and HIF-2α (EPAS-1) by the use of RNA interference: erythropoietin is a HIF-2α target gene in Hep3B and Kelly cells. FASEB J. 18, 1462-1464 (2004) using 5×104 U87 cells transduced with pLOC-vector, pLOC-DYRK1B WT or pLOC-DYRK1B-K140R mutant in 2 μl phosphate buffer. In brief, 5 days after lentiviral infection, cells were injected 2 mm lateral and 0.5 mm anterior to the bregma, 2.5 mm below the skull of 4-6-week-old athymic nude (Nu/Nu, Charles River Laboratories) mice. Mice were monitored daily for abnormal ill effects according to AAALAS guidelines and euthanized when neurological symptoms were observed. Tumours were dissected and fixed in formalin for immunohistochemical analysis and immunofluorescence using V5 antibody (Life technologies, 46-0705) to identify exogenous DYRK1B and an antibody against human vimentin (Sigma, V6630) to identify human glioma cells. A Kaplan-Meier survival curve was generated using the GraphPad Prism 6.0 software package (GraphPad). Points on the curves indicate glioma related deaths (n=7 animals for each group, p was determined by log rank analysis). Non-glioma related deaths were not observed. Mice injected with U87 cells transduced with pLOC-DYRK1B WT that did not show neurological signs on day 70 were euthanized for histological evaluation and shown as tumour-free mice in FIG. 13G.

Immunohistochemistry and Immunofluorescence

Tissue preparation and immunohistochemistry on tumour xenografts were performed as previously described in Warnecke, C. et al. Differentiating the functional role of hypoxia-inducible factor (HIF)-1α and HIF-2α (EPAS-1) by the use of RNA interference: erythropoietin is a HIF-2α target gene in Hep3B and Kelly cells. FASEB J. 18, 1462-1464 (2004), Almond, D. & Cardozo, T. Assessment of immunologically relevant dynamic tertiary structural features of the HIV-1 V3 loop crown R2 sequence by ab initio folding. J. Vis. Exp. 43, 2118 (2010), and Cawthorne, C., Swindell, R., Stratford, I. J., Dive, C. & Welman, A. Comparison of doxycycline delivery methods for Tet-inducible gene expression in a subcutaneous xenograft model. J. Biomol. Tech. 18, 120-123 (2007). Antibodies used in immunostaining are: HIF2α, mouse monoclonal, 1:200 (Novus Biological, NB100-132); Olig2, rabbit polyclonal, 1:200 (IBL International, JP18953); human Vimentin 1:50 (Sigma, V6630), Bromodeoxyuridine, mouse monoclonal 1:500 (Roche, 11170376001), V5 1:500 (Life technologies, 46-0705). Sections were permeabilized in 0.2% tritonX-100 for 10 min, blocked with 1% BSA-5% goat serum in PBS for 1 h. Primary antibodies were incubated at 4° C. overnight. Secondary antibodies biotinylated (Vector Laboratories) or conjugated with Alexa594 (1:500, Molecular Probes) were used. Slides were counterstained with haematoxylin for immunohistochemistry and DNA was counterstained with DAPI (Sigma) for immunofluorescence. Images were acquired using an Olympus 1×70 microscope equipped with digital camera and processed using Adobe Photoshop CS6 software. BrdU-positive cells were quantified by scoring the number of positive cells in five $4E^{-3}$ mm² images from 5 different mice from each group. Blinding was applied during histological analysis. Data are presented as means of five different mice±standard deviation (s.d.) (two-tailed Student's t-test, unequal variance).

Computational Analysis of Dependency of the HIF2α Regulon on ID2 Activity

To determine if ID2 modulates the interactions between HIF2α and its transcriptional targets a modified version of MINDy algorithm as described in Wang, K. et al. Genomewide identification of post-translational modulators of transcription factor activity in human B cells. Nature Biotechnol. 27, 829-837 (2009), called CINDy and described in Giorgi, F. M. et al. Inferring protein modulation from gene expression data using conditional mutual information. PLoS ONE 9, e109569 (2014) was used. CINDy uses adaptive partitioning method to accurately estimate the full conditional mutual information between a transcription factor and a target gene given the expression or activity of a signalling protein. Briefly, for every pair of transcription factor and target gene of interest, it estimates the mutual information that is, how much information can be inferred about the target gene when the expression of the transcription factor is known, conditioned on the expression/activity of the signalling protein. It estimates this conditional mutual information by estimating the multi-dimensional probability densities after partitioning the sample distribution using adaptive partitioning method. The CINDy algorithm was applied on gene expression data for 548 samples obtained from The Cancer Genome Atlas (TCGA). Since the activity level and not the gene expression of ID2 is the determinant of its modulatory function that is, the extent to which it modulates the transcriptional network of HIF2α, an algorithm called Virtual Inference of Protein-activity by Enriched Regulon analysis (VIPER) was used to infer the activity of ID2 protein from its gene expression profile as described in Alvarez, M. J., Giorgi, F. M. & Califano, A. Using viper, a package for virtual inference of protein-activity by enriched regulon analysis. Bioconductor, 1-14 (2014). VIPER method allows the computational inference of protein activity, on an individual sample basis, from gene expression profile data. It uses the expression of genes that are most directly regulated by a given protein, such as the targets of a transcription factor (TF), as an accurate reporter of its activity. The targets of ID2 were defined by running ARACNe algorithm on 548 gene expression profiles and use the inferred 106 targets to determine its activity as shown in Table 1.

TABLE 1

| List of ID2-regulated genes inferred from ARACNe/VIPER |
|---|
| ACSL6 |
| ACYP2 |
| AGT |
| ANXA4 |
| ANXA9 |
| APC |
| AQP1 |
| AQP4 |
| ARMCX1 |
| BAALC |
| BCAN |
| BCAS2 |
| BID |
| BNIP3L |
| C1orf165 |
| C1orf50 |
| C1orf61 |
| CD38 |
| CDK2AP1 |
| CDKL3 |
| CDO1 |
| CLDN6 |
| COL10A1 |
| CPE |
| CRYAB |
| CXCR7 |
| DPYSL2 |
| EDG1 |
| EIF1B |
| ENOPH1 |
| F7 |
| FAM110B |
| FEZ1 |
| GBAS |
| GFAP |
| GNPDA1 |
| GOLGA7 |
| GOLSYN |
| GPM6A |
| GPR19 |
| GRIA2 |
| HHLA3 |
| HIG2 |
| HOXA4 |
| ID3 |
| ID4 |
| IL17RB |
| IL33 |
| ITPR3 |
| KRT18 |
| LSAMP |
| MALL |

TABLE 1-continued

List of ID2-regulated genes inferred from ARACNe/VIPER

MAPT
MARCH3
MFAP3L
MGC70863
MSTN
MSX1
MUT
NCALD
NDP
NDUFA5
NFASC
NPAL2
NRN1
NRXN2
NSL1
OXR1
PAQR6
PCDH8
PEA15
PGAM2
PGM1
PKIA
PLSCR4
PRKAB2
RABL5
RASL12
RBM35B
RCHY1
RHEB
RNF13
RRAGD
S100B
SALL2
SAP30
SCG3
SCN3A
SCNN1A
SEPT7
SLITRK3
SNN
SPAG16
TCEAL1
TCF12
THTPA
TRIM36
TSC22D4
TSPAN12
TSPAN13
TUBA1A
UBE2E1
USP33
WDR47
ZNF107
ZNF423

CINDy was applied on 277 targets of HIF2α represented in Ingenuity pathway 110 analysis (IPA) and for which gene expression data was available as shown in Table 2.

TABLE 2

List of HI2a target genes inferred from Ingenuity Pathway Analysis

ABCF2
ABCG2
ABI1
ACACA
ACP5
ADM
AKAP12
AKAP8L
ALDOC
ANGPT2
ANGPTL4
APC
APEX1

TABLE 2-continued

List of HI2a target genes inferred from Ingenuity Pathway Analysis

APP
AR
AREG
ARG1
ARG2
ARNT
ARNT2
ARNTL
ARNTL2
ATG5
BAG2
BATF
BBC3
BBS1
BBS4
BCL7C
BIRC3
BNIP3
BRAF
C1QA
CA12
CA9
CACNA1A
CAT
CAV1
CCND1
CCR2
CCR5
CHKA
CHMP2B
CITED2
CKB
CKM
CKMT2
CLK3
CNKSR2
CNOT1
CNOT7
CORO1A
CREBBP
CTGF
CTNNB1
CXCL2
CXCR4
CYBA
CYBRD1
CYP51A1
DBP
DDIT3
DECR2
DMXL1
DNAJA2
DPF2
E2F4
EDN1
EGF
EGFR
EGLN1
EGLN2
EGLN3
EIF3E
EIF4E2
EIF5A
ELAVL1
EMD
ENO1
ENO2
EP300
EPAS1
EPO
ERBB4
ESRRA
ETS1
EWSR1
F12
FABP2
FASN
FBLN2

TABLE 2-continued

List of HI2a target genes inferred from Ingenuity Pathway Analysis

FGF2
FH
FHL1
FLG
FLT1
FMO5
FN1
FOS
FXN
GADD45B
GAL3ST1
GALR2
GBE1
GCHFR
GJA1
GPX1
GTF3C3
GYS2
HAMP
HIF1A
HIF1AN
HIF3A
HIST1H1C
HIST1H2AC
HMGCS1
HOXA5
HSP90AA1
HSPA4
HSPA5
IGF1
IGFBP3
IGFBP5
IKBKAP
IKBKG
IL13
IL1B
IL6
INHBB
IRS2
ITGA2B
ITGAV
ITGB3
ITIH5
ITPR1
JUN
KDR
KLF2
KLF5
KLHL20
L1CAM
LDHA
LDLR
LOX
LOXL2
MAFF
MAX
MB
MCM3
MCM3AP
MCM7
MED1
MED12
MED14
MED15
MED16
MED17
MED18
MED20
MED22
MED23
MED24
MED25
MED27
MED4
MED7
MED8
MEF2C
MIF
MITF
MMP14
MYC
MYOM2
NCAPD3
NDN
NDRG1
NDUFB6
NEDD8
NEFL
NEUROG1
NFE2L2
NFIL3
NFYB
NOS3
NOTCH1
NOX1
NOX4
NPM1
NRAS
NRN1
PFKFB3
PGF
PGR
PHB
PHB2
PIAS2
PIK3CA
PLOD2
PPARG
PPP1R14B
PRKCA
PSMB1
PSMC3
PSMD1
PTEN
PTPRZ1
RASSF1
RB1CC1
RBM4
RET
RUVBL1
SATB1
SCAP
SERPINE1
SF3A3
SFTPB
SFTPD
SLC11A2
SLC16A4
SLC29A1
SLC2A1
SLC2A3
SLC2A4
SLC6A8
SLC7A5
SMAD3
SMARCA2
SMARCA4
SMARCB1
SMARCC1
SMARCC2
SOD1
SOD2
SOX10
SOX15
SOX9
SP1
SPAG4
SPHK1
SPP1
SREBF1
SSBP3
STAT3
STAT5A
STC2
SUMO1
SUMO2

TABLE 2-continued

List of HI2a target genes inferred from Ingenuity Pathway Analysis

TAF9B
TCEB1
TCEB2
TEK
TERF2IP
TERT
TFAP2A
TFAP2B
TGFA
TGFB3
TMEM45A
TMPRSS6
TNFAIP3
TNFSF15
TPP2
TRIM21
TRIM28
TRIM33
UBC
UCP2
UGP2
UNG
USP8
VEGFA
WISP2
WNT1
WNT10B
WRNIP1
XPO1
YTHDF2

Of these 277 targets, 77 are significantly modulated by ID2 activity (P value≤0.05). Among the set of target genes whose expression was significantly positively correlated (P value≤0.05) with the expression of HIF2α irrespective of the activity of ID2, that is, correlation was significant for samples with both high and low activity of ID2, the average expression of target genes for a given expression of HIF2α was higher when the activity of ID2 was high. The same set of target gene were more correlated in high ID2 activity samples compared to any set of random genes of same size (FIG. 13A), whereas they were not in ID2 low activity samples (FIG. 13B). 25% of all samples with the highest/lowest ID2 activity were selected to calculate the correlation between HIF2α and its targets.

Figure 13A:
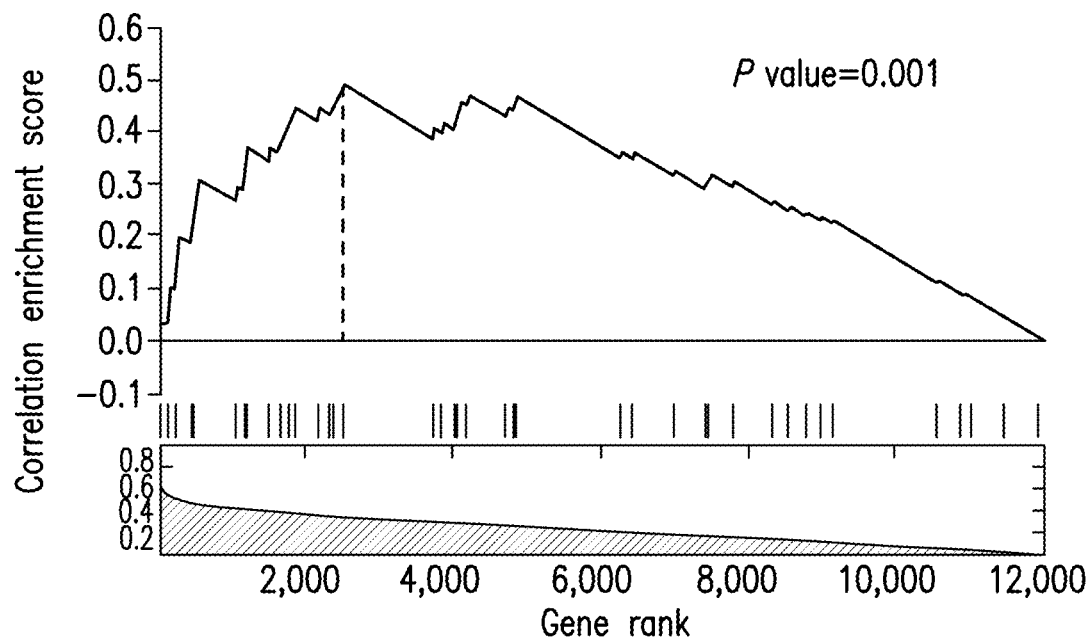
FIG. 13A-13I show the effects of DYRK1 kinases on human glioma growth by repressing an ID2-HIF2α network.
Figure 13B:
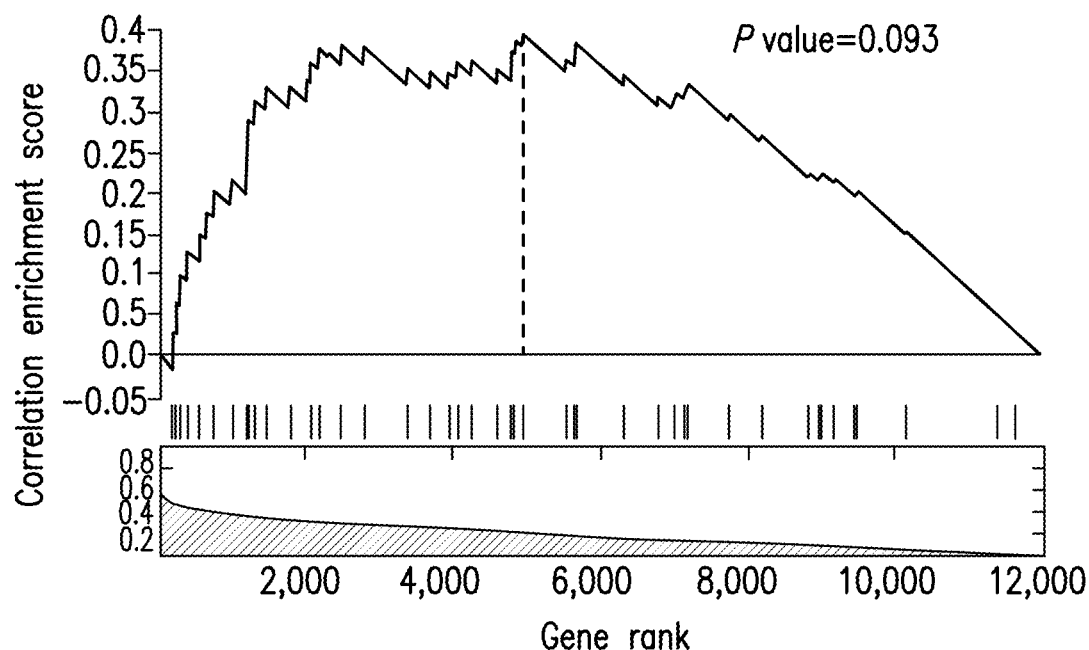

To determine whether regulation of ID2 by hypoxia might impact the correlation between high ID2 activity and HIF2α shown in FIG. 13A and FIG. 13B, the effects of ID2 activity versus ID2 expression for the transcriptional connection between HIF2α and its targets were compared. 25% of all patients (n=548) in TCGA with high ID2 activity and 25% of patients with low ID2 activity were selected the enrichment of significantly positively correlated targets of HIF2α in each of the groups was tested. This resulted in significant enrichment (P value<0.001) in high ID2 activity but showed no significant enrichment (P value=0.093) in low ID2 activity samples. Moreover, the difference in the enrichment score (ΔES) in these two groups was statistically significant (P value<0.05). This significance was calculated by randomly selecting the same number of genes as the positively correlated targets of HIF2α, and calculating the ΔES for these randomly selected genes, giving ΔESrand. This step was repeated 1,000 times to obtain 1,000 ΔESrand that are used to build the null distribution (FIG. 15B). The null distribution was used to estimate P value calculated as (number of ΔES>ΔESrand)/1,000. Enrichment was observed only when ID2 activity was high but not when ID2 activity was low, thus suggesting that ID2 activity directionally impacts the regulation of targets of HIF2α by HIF2α. Consistently, the significant ΔES using ID2 activity suggests that ID2 activity is determinant of correlation between HIF2α and its targets.

Conversely, when a similar analysis was performed using ID2 expression instead of ID2 activity, significant enrichment of positively correlated targets of HIF2α both in samples with high expression (P value=0.025) and low expression of ID2 (P value=0.048) was found. Given the significant enrichment in both groups, no any significant difference in the enrichment score in the two groups (P value of ΔES=0.338) was observed. Thus, while the determination of the ID2 activity and its effects upon the HIF2α-targets connection by VIPER and CINDy allowed determination of the unidirectional positive link between high ID2 activity and HIF2α transcription, a similar analysis performed using ID2 expression contemplates the dual connection between ID2 and HIF2α.

Kapman-Meier Analysis for DYRK1A and DYRK1B in Human GBM

To test if expression of DYRK1A and DYRK1B are predictor of prognosis, patients were divided into two cohorts based on their relative expression compared to the mean expression of all patients in GBM. The first cohort contained the patients with high expression of both DYRK1A and DYRK1B (n=101) and the other cohort contained patients with low expression (n=128). Average expression for both DYRK1A and DYRK1B was used, which individually divide the patient cohort into half and half. However, when the condition that patients should display higher or lower average expression of both these genes was used, then approximately 19% for high expression and 24% for low expression were selected. Selection of these patients was entirely dependent on the overall expression of these genes in the entire cohort rather than a predefined cutoff. Kaplan-Meier survival analysis showed the significant survival benefit for the patients having the high expression of both DYRK1A and DYRK1B (P value=0.004) compared to the patients with low expression. When similar analysis was performed using only the expression of DYRK1A or DYRK1B alone, the prediction was either non-significant (DYRK1A) or less significant (DYRK1B, p-value=0.008) when compared to the predictions using the expression of both genes.

Example 2—Hypoxia Regulates Phosphorylation of ID2 by DYRK1

Figure 3A:
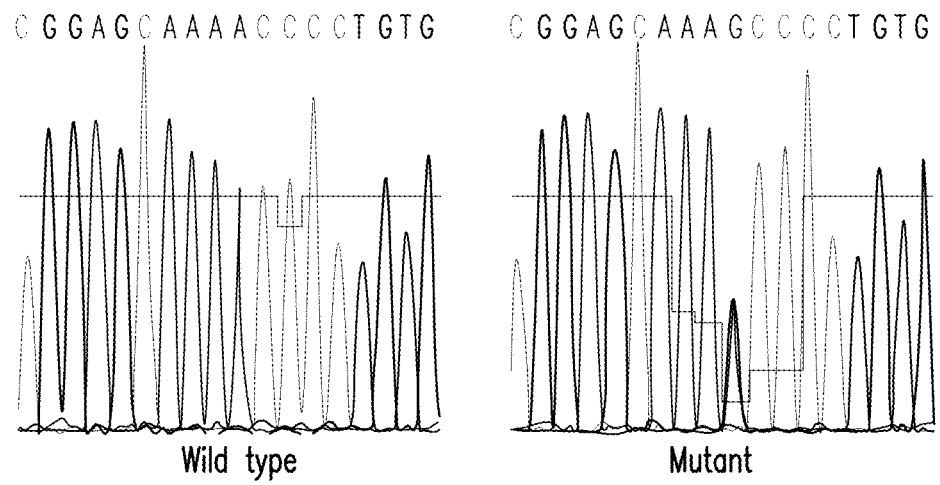
Figure 3B:
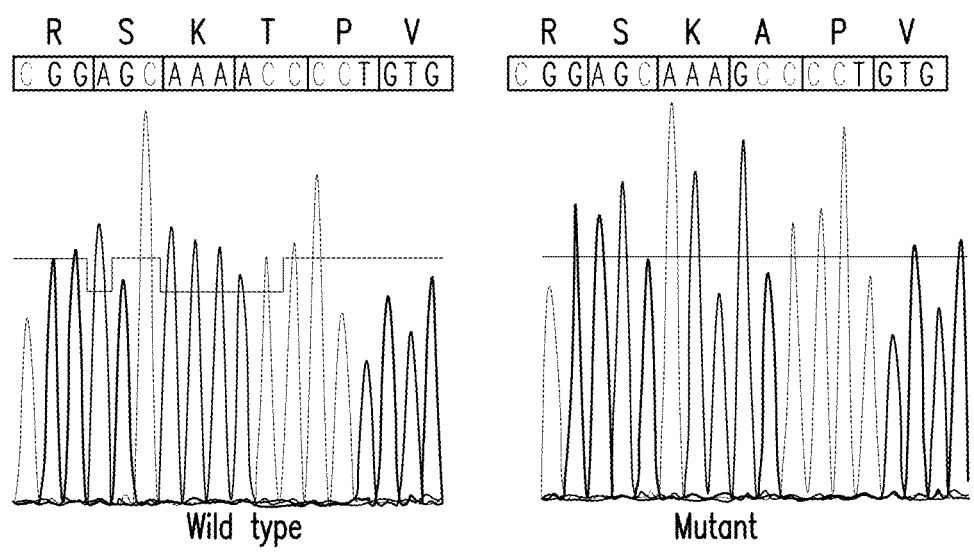

A sequencing analysis of the ID2 gene in cancer cells was performed. Results are presented in FIG. 3A and FIG. 3B and revealed that the colorectal cancer cell line HRT-18 harbors and expresses a mutant ID2 (T27A) protein. Sequencing of DNA from the colon cancer cell line HRT-18 showed a heterozygous mutation resulting in the change of codon-27 from ACC (Thr) to GCC (Ala) (right). (FIG. 3A), Both wild-type and mutant ID2(T27A) were expressed in HRT-18 colon cancer cells. Sequence analysis of representative clones (out of 20 clones) derived from HRT-18 cDNA demonstrated expression of wild-type (left panel) and mutant (right panel) alleles (FIG. 3B).

The importance of Thr 27 in ID2 is also demonstrated by its conservation across species, as illustrated in FIG. 3C.

The primary role of ID proteins is to preserve stem cell properties, a function widely documented in neural stem cells (NSCs). Therefore, to interrogate the significance of the ID2(T27A) mutation, the self-renewing capacity of ID2-null NSCs reconstituted with wild type (WT) or ID2 (T27A) was tested (FIG. 4A) Introduction of ID2(T27A) in ID2-null NSCs increased neurosphere formation in serial passages by more than 50% when compared with WT ID2 (P=0.00883-0.000229; t ratio=4.772-12.597) and caused a 2.4-fold increase in cell expansion rate (40.5±1.7 versus 16.7±0.831; P<0.0001, FIG. 4B, FIG. 4C, FIG. 4D).

From the analysis of 18 candidate kinases, the dual-specificity tyrosine-phosphorylation-regulated protein kinases 1A and 1B (DYRK1A and DYRK1B) were identified as the only enzymes able to phosphorylate Thr 27 of ID2 (FIG. 4E and FIG. 3D (presenting the results of an in vitro kinase assay using bacterially expressed GST-ID proteins and recombinant DYRK1A (10 mM) or vehicle for 24 h as analyzed by western blot using the indicated antibodies)).

The sequence surrounding the Thr 27 residue in ID2 resembles the DYRK1 phosphorylation consensus motif RX(X)(S/T)P as described in Himpel, S. et al. Specificity determinants of substrate recognition by the protein kinase DYRK1A. J. Biol. Chem. 275, 2431-2438 (2000) and is highly conserved in different species as shown in FIG. 3C.

Antibodies against a phospho-T27-ID2 peptide confirmed that ID2 is phosphorylated by WT DYRK1B as described in Lee, K., Deng, X. & Friedman, E. Mirk protein kinase is a mitogen-activated protein kinase substrate that mediates survival of colon cancer cells. Cancer Res. 60, 3631-3637 (2000), but not the inactive DYRK1B(K140R) kinase (FIG. 4A, FIG. 4F (show in phosphorylation of ID2 but not mutant ID2(T27A) by DYRK1B), FIG. 4G (showing phosphorylation of endogens ID2 by DYRK1A in U87 cells), and FIG. 4H (showing phosphorylation of endogenous ID2 by DYRK1B, but not the kinase inactive GFP-DYRK1B (K140R) in U87 cells).

Endogenous and exogenous ID2 and ID2(T27A) co-precipitated endogenous DYRK1A and DYRK1B (FIG. 4I (showing binding between endogenous DYRK1 and ID2) and FIG. 3E (presenting results when U87 cells transfected with Flag-ID2, Flag-ID2(T27A) or the empty vector were immunoprecipitated with Flag antibody and co-precipitated proteins were analyzed by western blot using DYRK1A, DYRK1B and Flag antibodies, β-actin was used as control for loading). Treatment of glioma cells with harmine, a small-molecule inhibitor of DYRK1 as described in Gockler, N. et al. Harmine specifically inhibits protein kinase DYRK1A and interferes with neurite formation. FEBS J. 276, 6324-6337 (2009), or combined short hairpin RNA (shRNA)-mediated silencing of DYRK1A and DYRK1B reduced Thr 27 phosphorylation of ID2 (FIG. 5E (showing that silencing of DYRK1 downregulates phospho-Thr27 of IDs and increases HIF2α in U87 cells) and FIG. 3F (presenting western blot results for U87 stably transfected with Flag-ID2 and treated with harmine).

The regulatory mechanisms controlling Thr 27 phosphorylation of ID2 were identified. Exposure of human GBM-derived glioma stem cells (GSCs) to hypoxia or hypoxia-mimicking agent cobalt chloride (CoCl2) caused loss of Thr 27 phosphorylation (FIG. 6A (showing that hypoxia inhibits phosphorylation of ID2 Thr27 in GSC #1123) and FIG. 7A (presenting western blot analysis with the indicated antibodies of cellular lysates of U87 glioma cells treated with 10 nM $CoCl_2$ for the indicated times). Determination of the Thr 27 phosphorylation stoichiometry of ID2 in the neuronal cell line SK—N—SN revealed that 21.08% of ID2 was phosphorylated on Thr 27 in normoxia but the phosphorylation dropped to 2.28% in a hypoxic environment (FIG. 7B (presenting western blot analysis with the indicated antibodies of SK—N-Sh cells treated with 300 mM $CoCl_2$ for the indicated times) and FIG. 7C (presenting stoichiometric evaluation of pThr-27-ID2 in SK—N-SH cells untreated or treated with $CoCl_2$ for 24 h; cellular lysates were prepared in denaturing buffer and were immunoprecipitated using pT27-ID2 antibody or normal rabbit IgIG; aliquots of whole cellular lysates (WCL, mg) and immunoprecipitates were assayed by western blot using pT27-ID2 and non-phosphorylated ID2 antibodies (upper panels); the efficiency of immunoprecipitation with anti-pT27-ID2 antibody from untreated cells was determined to calculate the percent of the T27-ID2 in the absence and in the presence of $CoCl_2$ (lower panel)).

Mirroring the reduction of Thr 27 phosphorylation of ID2, $CoCl_2$ reduced DYRK1 kinase activity (FIG. 6B (showing data from GFP-DYRK1 immunoprecipitates from U87 cells untreated or treated with $CoCl_2$ and recombinant Flag-ID2 in an in vitro kinase assay) and FIG. 7D (presenting data from an assay in which 293T cells expressing GFP-DYRK1 proteins untreated or treated with 100 mM $CoCl_2$ for 12 h were used as a source of active DYRK1 kinase; the kinase activity of anti-GFP-DYRK1 immunoprecipitates was tested in vitro using bacterially expressed and purified Flag-ID2 as a substrate; kinase reactions were evaluated by western blot using p-T27-ID2 antibodies (top); analysis of kinase reactions by Flag immunoblot showed a similar amount of ID2 protein in each kinase reaction (middle); immunocomplexes were analyzed by western blot using GFP antibody (bottom)).

$CoCl_2$ also reduced DYRK1 auto-phosphorylation, an event required for the activity of DYRK1 kinase as described in Himpel, S. et al. Identification of the autophosphorylation sites and characterization of their effects in the protein kinase DYRK1A. Biochem. J. 359, 497-505 (2001) (FIG. 7E (showing data from assays in which lysates from U251 cells expressing GFP-DYRK1 proteins untreated or treated with of 100 mM $CoCl_2$ for 6 h were immunoprecipitated using GFP antibodies; a western blot was performed using anti-p-Tyrosine (p-Tyr) or GFP antibodies; analysis of WCL showed similar expression levels of DYRK1 proteins. α-tubulin was used as control for loading), FIG. 7F (presenting data from assays in which lysates from 293T cells expressing GFP-DYRK1A untreated or treated with 100 mM $CoCl_2$ for 12 h were immunoprecipitated with anti-p-Tyr antibodies and analyzed by western blot using antibodies against GFP, α-tubulin was used as control for loading), and FIG. 7G (presenting data in which lysates from 293T cells expressing GFP-DYRK1B untreated or treated with 100 mM $CoCl_2$ for 12 h were immunoprecipitated with anti-p-Tyr antibodies and analyzed by western blot using antibodies against GFP; α-tubulin was used as control for loading)).

Similarly, exposure of GSCs to low oxygen decreased DYRK1A and DYRK1B tyrosine auto-phosphorylation (FIG. 6C (showing that hypoxia reduces tyrosine phosphorylation by DYRK1A as evaluated by anti-p-Tyr immunoprecipitation in GSC #1123 cells) and FIG. 6D (showing that hypoxia reduces tyrosine phosphorylation by DYRK1B as evaluated by anti-p-Tyr immunoprecipitation in GSC #1123 cells)).

Prolyl hydroxylases PHD1, PHD2 and PHD3 operate as direct sensors of cellular oxygen concentration as described in Kaelin, W. G. Jr & Ratcliffe, P. J. Oxygen sensing by metazoans: the central role of the HIF hydroxylase pathway. Mol. Cell 30, 393-402 (2008) and Semenza, G. L. HIF-1, O(2), and the 3 PHDs: how animal cells signal hypoxia to the nucleus. Cell 107, 1-3 (2001). Immunoprecipitation using an antibody that recognizes hydroxyprolines indicated that DYRK1A and DYRK1B carry hydroxylated prolines, and CoCl2 abrogated DYRK1 prolyl hydroxylation (FIG.

6E (showing that CoCl$_2$ inhibits proline hydroxylation of DYRK1A and DYTRK1B as shown by anti-hydroxyproline immunoprecipitation in U87 glioma cells).

DYRK1A and DYRK1B interacted in vivo with PHD1 (FIG. 6F (showing that endogenous DYRK1A and DYRK1B interact with Flag-PDH1 in U87 cells).

Further, the expression of PHD1 enhanced prolyl hydroxylation of both DYRK1A and DYRK1B (FIG. 7H (presenting data from assay in which U87 transfected with GFP-DYRK1A, GFP-DYRK1B or GFP and Flag-PHD1, Flag-PHD2, or Flag-PHD3 were immunoprecipitated using anti-hydroxyproline antibody; western blot was performed using GFP antibody (upper panels); lower panels present data for the WCL control)).

In particular, DYRK1B interacted with PHD1 through the kinase domain (FIG. 6G (showing that the kinase domain (KD), but not the N- or C-terminal domains of DYRK1B interact with PHD1 in a co-immunoprecipitation assay)). The activity of DYRK1A and DYRK1B towards Thr 27 of ID2 was potentiated by PHD1 in vitro (FIG. 6H (showing that expression of PDH1 enhances cellular DYRK1 kinase activity in an in vitro phosphorylation assay using recombinant ID2)) and in vivo (FIG. 6I (showing that expression of PHD1 enhances DYRK1 kinase activity towards ID2 Thr27 in vivo)). Thus, oxygen deprivation induces a constitutively active ID2 by inactivating DYRK1 kinases, which are positively regulated substrates of PHD1.

Example 3—Phosphorylation of ID2 by DYRK1 Destabilizes HIF2a

Human GSCs were used to interrogate the effects of DYRK1 and ID2(T27A) on HIF2α and glioma stemness. Lentiviral transduction of the DYRK1-resistant ID2(T27A) mutant in GSC #48 resulted in elevation of HIF2α and enhanced tumor sphere forming capacity as measured by limiting dilution assay (LDA) (FIG. 8A (presenting results of an assay in which GSC #48 cells were transduced with lentiviruses expressing ID2-WT, ID2(T27A), or the empty vector), FIG. 8B (presenting results in which cells were analyzed by in vitro LDA), FIG. 8C (presenting gliomasphere frequency calculated using a representative regression plot of the Data from FIG. 8B; data in the histograms represent means of 3 biological replicates±s.d.; **P=0.00163), and FIG. 8D (presenting a set of microphotographs that show representative gliomasphere cultures of cells treated as in FIG. 8A)).

Figure 8A:
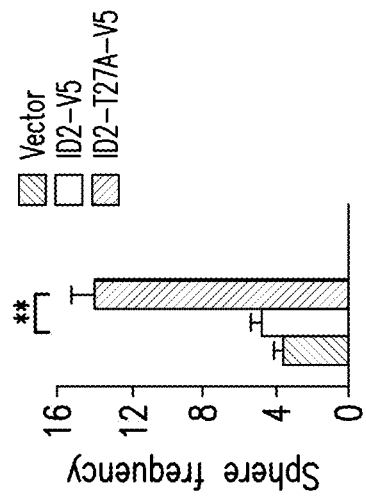
Figure 8B:
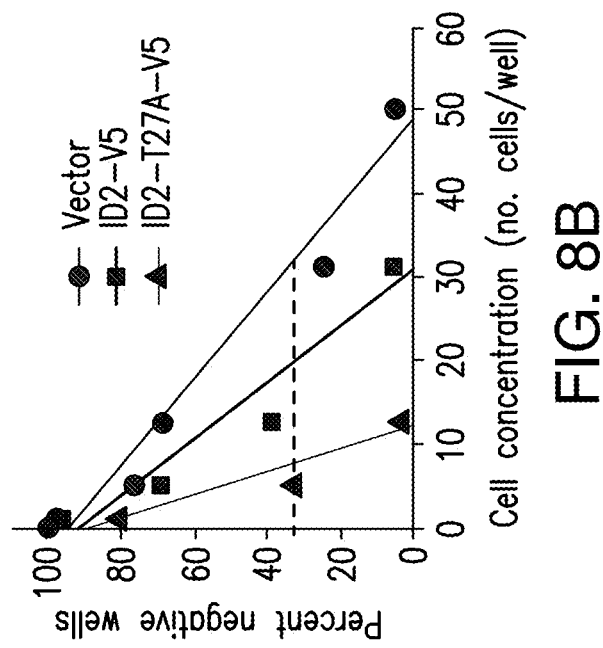
Figure 8C:
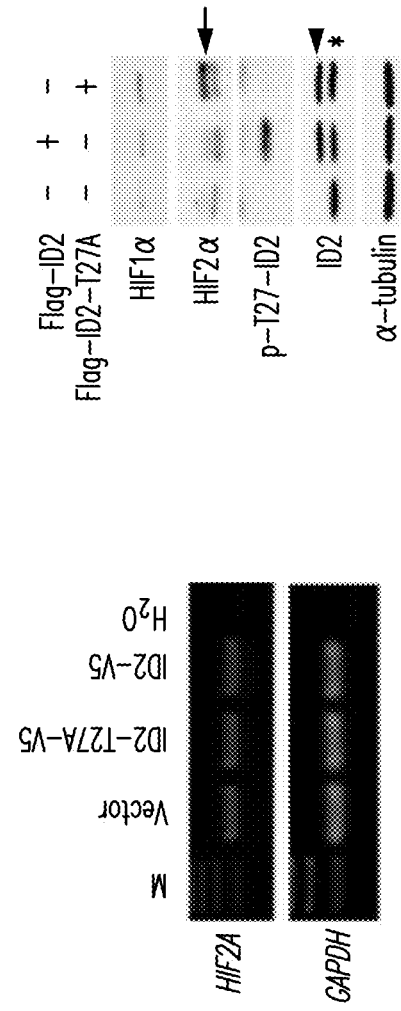
Figure 8D:
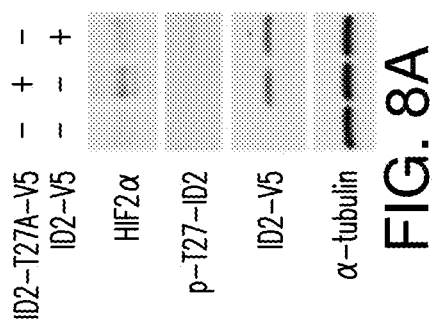
Figure 8E:
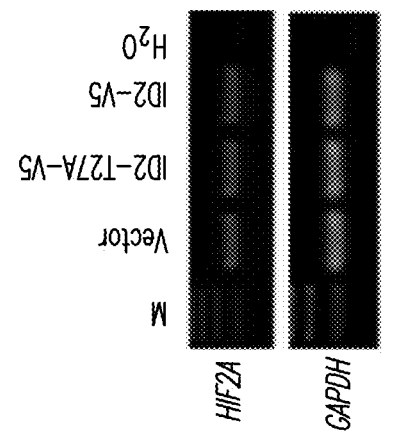

ID2(T27A)-induced accumulation of the HIF2α protein was independent of transcription (FIG. 8E (presenting semiquantitative RT-PCR analysis of HIF1α mRNAs from cells treated in in FIG. 8A)).

Figure 8F:
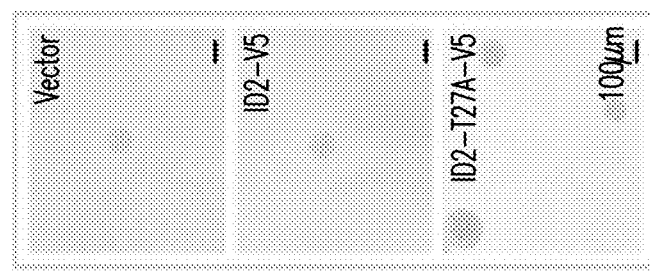

When detectable, HIF1α levels mirrored those of HIF2α but with more limited changes (FIG. 8F (presenting data from an assay in which U87 cells stably expressing Flag-ID2 or Flag-ID2(T27A) were analyzed by western blot using the indicated antibodies; arrows point to specific bands; the asterisk indicates a non-specific band)).

Expression of DYRK1 in GSC #34 and GSC #31 reduced HIF2α, the HIF2α target TGFα and the glioma stem cell marker SOX2 (FIG. 5A (showing that phosphorylation of ID2, but not the mutant ID2(T27A) by GFP-DYRK1B downregulates HIF2α), FIG. 8G (presenting data from assay in which GSC #34 cells were transduced with lentiviruses expressing DYRK1B-V5 or empty vector; cells were analyzed by western blot using the indicated antibodies; the arrow points to specific band; the asterisk indicates a non-specific band), and FIG. 8H (presenting qRT-PCR from cells treated as in FIG. 8G; data in the histograms represent means±s.d. (n=9, triplicate experiments each performed in triplicate; ***P=8.44524×10$^{-7}$ for TGFA))). Also in this case HIF2a mRNA was unchanged (FIG. 8I and FIG. 8J (presenting semiquantitative RT-PCR for HIF2α for mRNA from the assays of FIG. 5A, FIG. 5B, and FIG. 5C).

LDA and serial clonal experiments showed that the DYRK1-induced decrease of HIF2α attenuated glioma stemness (FIG. 5B (showing that decreased frequency of gliomaspheres by DYRK1B in in vitro LDA of parallel cultures is rescued by ID2(T27A); data are means of 3 biological replicates±s.d.; P=0.0031 (vector versus DYRK1B); *P=0.00022 (DYRK1B versus DYRK1B plus ID2(T27A))), FIG. 5C (presenting a set of microphotographs of representative cultures in FIG. 5B), and FIG. 5D (presenting the serial clonal experiments of cells in FIG. 5B; data are means of 3 biological replicates±s.d. of percent gliomaspheres; *P=0.00059-0.00007 for vector versus DYRK1B plus vector; *P=0.0089-0.0008 for ID2(T27A) plus DYRK1B versus DYRK1B plus vector; NS: P=0.061-0.249 for ID2(T27A) plus DYRK1B versus vector)).

However, accumulation of HIF2α, expression of SOX2 and the frequency of GSCs were restored by co-expression of DYRK1 and ID2(T27A) but not ID2(WT) (FIG. 5A-D and FIG. 8K (showing results in an assay in which GSC #31 cells were transduced with lentiviruses expressing DYRK1B and ID2, ID2(T27A), or the empty vector; cells were analyzed by LDA; representative regression plot used to calculate gliomasphere frequency in FIG. 5C).

DYRK1-mediated inhibition of gliomasphere formation was overridden by co-expression of non-degradable HIF2α (HIF2α-TM) (FIG. 8L (presenting results for an ass y in which GSC #31 cells were transduced with lentiviruses expressing DYRK1B or the empty vector in the absence or in the presence of undegradable HIF2α (HIF2α-TM); cells were analyzed by in vitro LDA; representative regression plot used to calculate the frequency of gliomaspheres in cultures from three independent infections)).

Furthermore, silencing of DYRK1A or DYRK1B upregulated HIF2α and reduced phosphorylation of Thr 27 of ID2, with maximal effects after co-silencing of both DYRK1A and DYRK1B (FIG. 5E (showing that silencing of DYRK1 downregulates phospho-Thr 27 of ID2 and increases HIF2α in U87 cells)).

Figure 9A:
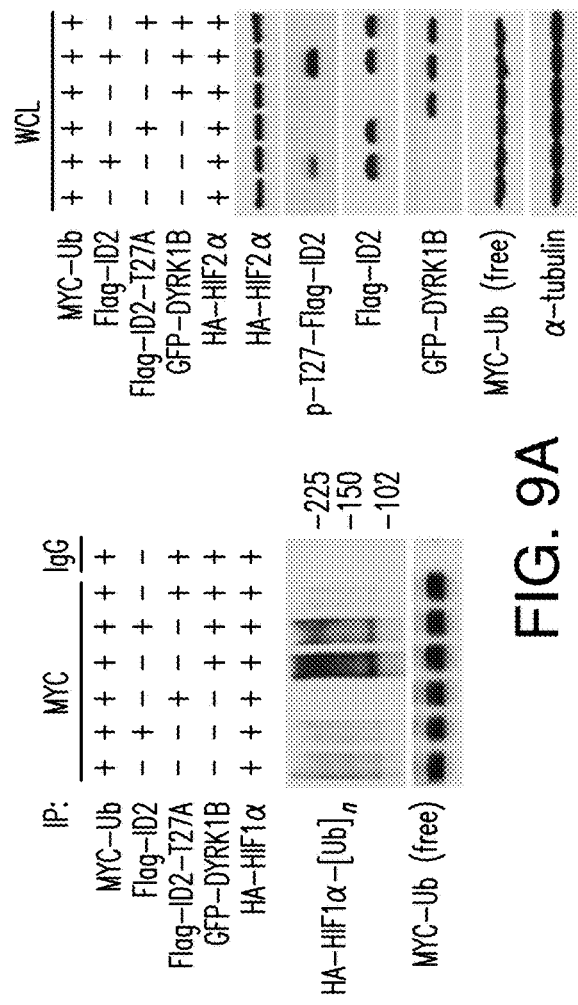

The effects of DYRK1 and ID2(T27A) on ubiquitylation and the stability of HIFα. DYRK1-mediated phosphorylation of Thr 27 triggered HIFα ubiquitylation and expression of ID2(T27A) reverted DYRK1 effect were also tested. (FIG. 5F (showing that ubiquitylation of HIF2α is enhanced by DYRK1B and reduced by ID2(T27A) as evaluate by in vivo ubiquitylation (left panels, MYC-Ub immunoprecipitation/HA-HIF2a western blot; right panels, whole cellular lysate (WCL) control) and FIG. 9A (showing results of assays of in vivo ubiquitylation of HIF1a protein; U87 cells transfected with the expression plasmids HIF1a and MYC-ubiquitin were co-transfected with Flag-ID2, Flag-ID2 (T27A), or the empty vector in the presence or in the absence of GFP-DYRK1B; after treatment with MG132 (20 mM) for 6 h, lysates were prepared in denaturing buffer and identical aliquots were immunoprecipitated with antibodies directed against MYC; an anti-HA antibody was used to detect HIF1α ubiquitin conjugates (left); whole cellular lysates (WCL) were also analyzed by western blot using the indicated antibodies (right))).

Similarly, expression of DYRK1B prevented accumulation of HIF2α under hypoxia and co-expression of ID2 (T27A) abrogated this response (FIG. 5G (showing that ID2(T27A) elevates HIF2α and opposed DYRK1B-mediated reduction in HIF2a during hypoxia).

Figure 9C:
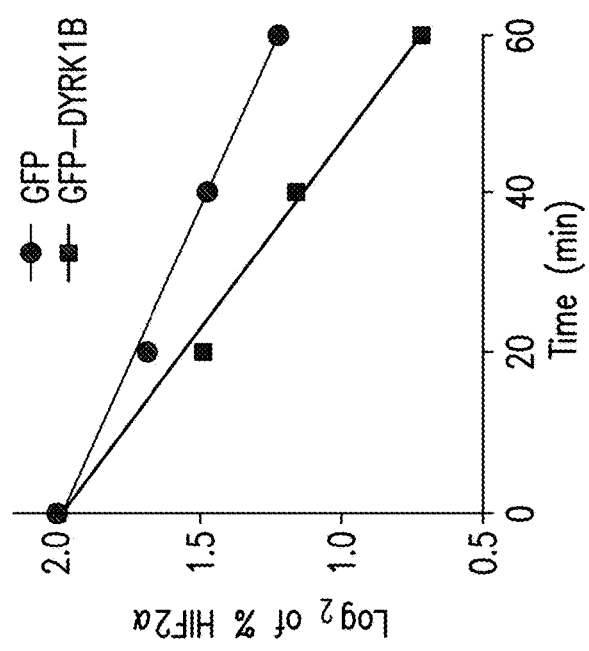
Figure 9B:
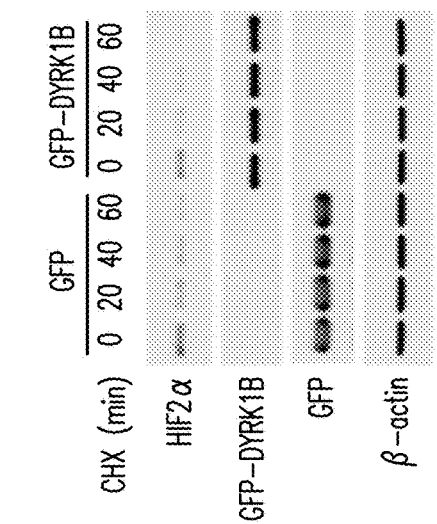

DYRK1 accelerated the decay of HIF2α during recovery from exposure to CoCl$_2$ and reduced HIF2α half-life, whole and ID2(T27A) countered these effects (FIG. 5H (showing that ID2(T27A) reverts DYRK1B-mediated decrease of HIF2α half-life during recovery from exposure to CoCl$_2$), FIG. 5I (showing quantification of HIF2α from the results in FIG. 5H), FIG. 9B (showing results of assays in which U87 cells were co-transfected with plasmids expressing HA-HIF2α and GFP-DYRK1B or GFP-vector; cells were treated with 50 mg ml$^{-1}$ of CHX for the indicated times and analyzed by western blot), and FIG. 9C (showing quantification of HIF2α protein from the experiment in FIG. 5B as the log$_2$ of the percent of HIF2α relative to untreated cells)).

Example 4—ID2 Binds and Disrupts the VCB-Cul2 Complex

Mass spectrometry analysis of ID2 immunoaffinity complexes as presented in Table 3 and Table 4, revealed that Elongin C, a component of the VCB-Cul2 ubiquitin ligase complex that includes VHL, elongin C, Elongin B, cullin 2, and RBX1 is an ID2-associated protein.

TABLE 3

List of peptides recovered after LC-MS/MS of ID2 complexes (Part A)

| Sequence | Mass | Charge | Xcorr |
|---|---|---|---|
| AKIHDIVLVGGSTR | 1465.84856 | 3 | 3.0715 |
| AKIHDIVLVGGSTR | 1465.84856 | 3 | 2.7004 |
| AKIHDIVLVGGSTR | 1465.84856 | 2 | 2.3695 |
| AKIHDIVLVGGSTR | 1465.84856 | 3 | 2.3167 |
| SQIFSTASDNQPTVTIK | 1836.93382 | 2 | 4.9468 |
| LYGSAGPPPTGEEDTAEKDEL | 2175.99284 | 2 | 4.8759 |
| IEWLESHQDADIEDFK | 1974.90798 | 2 | 4.8754 |
| LYGSAGPPPTGEEDTAEKDEL | 2175.99284 | 2 | 4.3491 |
| LYGSAGPPPTGEEDTAEKDEL | 2175.99284 | 2 | 4.1145 |
| IEWLESHQDADIEDFK | 1974.90798 | 3 | 3.9006 |
| SQIFSTASDNQPTVTIK | 1836.93382 | 2 | 3.88 |
| NELESYAYSLK | 1316.6369 | 2 | 3.8681 |
| SQIFSTASDNQPTVTIK | 1836.93382 | 2 | 3.746 |
| SQIFSTASDNQPTVTIK | 1836.93382 | 2 | 3.6332 |
| NQLTSNPENTVFDAK | 1677.80787 | 2 | 3.5277 |
| IEWLESHQDADIEDFK | 1974.90798 | 3 | 3.3991 |
| ELEEIVQPIISK | 1397.78864 | 2 | 3.3254 |
| ITPSYVAFTPEGER | 1566.77987 | 2 | 2.7954 |
| NELESYAYSLK | 1316.6369 | 2 | 2.6746 |
| NELESYAYSLK | 1316.6369 | 2 | 2.5416 |
| ITPSYVAFTPEGER | 1566.77987 | 2 | 2.3899 |
| DAGTIAGLNVMR | 1217.63069 | 2 | 2.3785 |

TABLE 3-continued

List of peptides recovered after LC-MS/MS of ID2 complexes (Part A)

| Sequence | Mass | Charge | Xcorr |
|---|---|---|---|
| NQTAEKEEFEHQQK | 1745.80892 | 3 | 3.2724 |
| NSLESYAFNMK | 1303.59874 | 2 | 3.2377 |
| NSLESYAFNMK | 1303.59874 | 2 | 3.1308 |
| NSLESYAFNMK | 1303.59874 | 2 | 2.7592 |
| NSLESYAFNMK | 1303.59874 | 2 | 2.7305 |
| NSLESYAFNMK | 1303.59874 | 2 | 2.4666 |
| SAKPVGPEDM*GATAVYELDTEK | 2324.09735 | 2 | 2.603 |
| SAKPVGPEDM*GATAVYELDTEK | 2324.09735 | 2 | 2.4483 |
| SAKPVGPEDM*GATAVYELDTEK | 2324.09735 | 2 | 2.4208 |
| SAKPVGPEDM*GATAVYELDTEK | 2324.09735 | 2 | 2.3288 |
| SAKPVGPEDM*GATAVYELDTEK | 2324.09735 | 2 | 2.3135 |
| SAKPVGPEDM*GATAVYELDTEK | 2324.09735 | 2 | 2.3111 |
| EVDEQMLNVQNK | 1446.68932 | 2 | 4.4619 |
| EVDEQMLNVQNK | 1446.68932 | 2 | 4.0857 |
| EVDEQMLNVQNK | 1446.68932 | 2 | 4.008 |
| AVLVDLEPGTMDSVR | 1601.82035 | 2 | 3.8567 |
| EIVHLQAGQCGNQIGAK | 1822.90139 | 2 | 3.8542 |
| LHFFMPGFAPLTSR | 1620.83554 | 2 | 3.7866 |
| INVYYNEATGGK | 1328.64812 | 2 | 3.3357 |
| EIVHLQAGQCGNQIGAK | 1822.90139 | 2 | 3.2542 |
| INVYYNEATGGK | 1328.64812 | 2 | 2.9854 |
| IREEYPDR | 1077.53235 | 2 | 2.6179 |
| AVLVDLEPGTM*DSVR | 1617.81636 | 2 | 2.5736 |
| IREEYPDR | 1077.53235 | 2 | 2.4756 |
| IREEYPDR | 1077.53235 | 2 | 2.3727 |
| EVDEQMLNVQNK | 1446.68932 | 3 | 2.3706 |
| TRPTTLGSSQFSGSGIDER | 1995.97308 | 3 | 4.8243 |
| GGLQSQSGTVVTTEIK | 1604.84902 | 2 | 4.7706 |
| TRPTTLGSSQFSGSGIDER | 1995.97308 | 3 | 4.4239 |
| KVPPGLPSSVYAPSPNSDDFNR | 2344.15685 | 3 | 3.8909 |
| GGLQSQSGTVVTTEIK | 1604.84902 | 2 | 3.8836 |
| QDLGLGSPAQLSSSGK | 1544.79153 | 2 | 3.8324 |
| GGLQSQSGTVVTTEIK | 1604.84902 | 2 | 3.7302 |
| QDLGLGSPAQLSSSGK | 1544.79153 | 2 | 3.6178 |
| KVPPGLPSSVYAPSPNSDDFNR | 2344.15685 | 3 | 3.4624 |
| KVPPGLPSSVYAPSPNSDDFNR | 2344.15685 | 3 | 3.4544 |
| KVPPGLPSSVYAPSPNSDDFNR | 2344.15685 | 3 | 3.4014 |
| LDDAIHVLR | 1051.58947 | 2 | 3.3431 |

TABLE 3-continued

List of peptides recovered after LC-MS/MS of ID2 complexes (Part A)

| Sequence | Mass | Charge | Xcorr |
|---|---|---|---|
| QDLGLGSPAQLSSSGK | 1544.79153 | 2 | 3.0592 |
| GSTSSSPYVAASHTPPINGSDSILGTR | 2659.2959 | 3 | 3.0528 |
| TRPTTLGSSQFSGSGIDER | 1995.97308 | 3 | 2.9841 |
| LDDAIHVLR | 1051.58947 | 2 | 2.9686 |
| TRPTTLGSSQFSGSGIDER | 1995.97308 | 3 | 2.8619 |
| VSAVSAEPPTTLPGTHPGLSETTNPMGHM | 2916.38666 | 3 | 2.8168 |
| VSAVSAEPPTTLPGTHPGLSETTNPMGHM | 2916.38666 | 3 | 2.5131 |
| DTGLPGCQSSLLR | 1403.6733 | 2 | 2.4851 |
| DTGLPGCQSSLLR | 1403.6733 | 2 | 2.3977 |
| PGTAYYSFSATSSR | 1494.686 | 2 | 2.3561 |
| LDDAIHVLR | 1051.58947 | 3 | 2.3061 |
| IEDHLDEAIHVLR | 1559.81764 | 3 | 5.0922 |
| IEDHLDEAIHVLR | 1559.81764 | 3 | 4.9046 |
| VPPGLPSSVYPPSSGEDYGR | 2060.99242 | 2 | 4.6329 |
| VPPGLPSSVYPPSSGEDYGR | 2060.99242 | 2 | 4.433 |
| VPPGLPSSVYPPSSGEDYGR | 2060.99242 | 2 | 3.881 |
| GTSQYYPSYSGSSR | 1539.67109 | 2 | 3.7661 |
| KVPPGLPSSVYPPSSGEDYGR | 2189.08738 | 3 | 3.5754 |
| KVPPGLPSSVYPPSSGEDYGR | 2189.08738 | 3 | 3.5562 |
| TSPDEDEDDLLPPEQK | 1827.81308 | 2 | 2.9657 |
| TSPDEDEDDLLPPEQK | 1827.81308 | 2 | 2.893 |
| AGATAAASEIK | 989.526216 | 2 | 2.8438 |
| VSGVVGDPQMVLSAPHPGLSEAHNPAGHM | 2891.39275 | 3 | 2.7766 |
| KVPPGLPSSVYPPSSGEDYGR | 2189.08738 | 3 | 2.7502 |
| KVPPGLPSSVYPPSSGEDYGR | 2189.08738 | 3 | 2.6432 |
| IGGIGTVPVGR | 1025.61022 | 2 | 3.1538 |
| IGGIGTVPVGR | 1025.61022 | 2 | 3.0129 |
| LPLQDVYK | 975.550961 | 2 | 2.3916 |
| TPVDDPMSLLYNMNDCYSK | 2262.95013 | 2 | 5.0806 |
| TPVDDPM*SLLYNMNDCYSK | 2278.94614 | 2 | 4.3227 |
| SKTPVDDPMSLLYNMNDCYSK | 2478.07713 | 3 | 4.3198 |
| TPVDDPMSLLYNM*NDCYSK | 2278.94614 | 2 | 4.2027 |
| TPVDDPM*SLLYNMNDCYSK | 2278.94614 | 2 | 4.1247 |
| NSLSDHSLGISR | 1285.64955 | 2 | 3.9822 |
| TPVDDPMSLLYNM*NDCYSK | 2278.94614 | 2 | 3.9732 |
| NSLSDHSLGISR | 1285.64955 | 2 | 3.9142 |
| TPVDDPM*SLLYNMNDCYSK | 2278.94614 | 2 | 3.9079 |
| NSLSDHSLGISR | 1285.64955 | 2 | 3.6019 |
| TPVDDPM*SLLYNMNDCYSK | 2278.94614 | 2 | 3.4646 |
| LKELVPSIPQNK | 1365.81004 | 2 | 3.41 |
| LKELVPSIPQNK | 1365.81004 | 2 | 3.338 |
| TPVDDPMSLLYNMNDCYSK | 2262.95013 | 2 | 3.3092 |
| TPVDDPMSLLYNM*NDCYSK | 2278.94614 | 3 | 3.2973 |
| LKELVPSIPQNK | 1365.81004 | 3 | 3.2399 |
| NSLSDHSLGISR | 1285.64955 | 2 | 3.2211 |
| LKELVPSIPQNK | 1365.81004 | 3 | 3.1592 |
| LKELVPSIPQNK | 1365.81004 | 2 | 3.1237 |
| LKELVPSIPQNK | 1365.81004 | 2 | 3.1195 |
| LKELVPSIPQNK | 1365.81004 | 2 | 3.0955 |
| TPVDDPM*SLLYNM*NDCYSK | 2294.94216 | 3 | 3.0528 |
| LKELVPSIPQNK | 1365.81004 | 2 | 3.0174 |
| LKELVPSIPQNK | 1365.81004 | 2 | 2.942 |
| LKELVPSIPQNK | 1365.81004 | 2 | 2.8417 |
| LKELVPSIPQNK | 1365.81004 | 2 | 2.8258 |
| LKELVPSIPQNK | 1365.81004 | 2 | 2.7809 |
| LKELVPSIPQNK | 1365.81004 | 2 | 2.7585 |
| LKELVPSIPQNK | 1365.81004 | 2 | 2.6244 |
| NSLSDHSLGISR | 1285.64955 | 2 | 2.6186 |
| NSLSDHSLGISR | 1285.64955 | 2 | 2.4724 |
| LKELVPSIPQNK | 1365.81004 | 3 | 2.4252 |
| NSLSDHSLGISR | 1285.64955 | 2 | 2.4186 |
| ELVPSIPQNK | 1124.63101 | 2 | 2.4098 |
| ELVPSIPQNK | 1124.63101 | 2 | 2.4087 |
| SKTPVDDPM*SLLYNMNDCYSK | 2494.07314 | 3 | 2.3313 |
| SNSFFEGVDWEHIR | 1722.78709 | 2 | 4.1304 |
| ERPAAISIEIK | 1226.71033 | 2 | 3.2344 |
| ERPAAISIEIK | 1226.71033 | 2 | 2.8678 |
| ERPAAISIEIK | 1226.71033 | 3 | 2.7401 |
| DWVFINYTYK | 1348.65722 | 2 | 2.5763 |
| DWVFINYTYK | 1348.65722 | 2 | 2.4834 |
| IINEPTAAAIAYGLDR | 1687.90137 | 2 | 5.7404 |
| IINEPTAAAIAYGLDR | 1687.90137 | 2 | 4.9175 |
| IINEPTAAAIAYGLDR | 1687.90137 | 2 | 4.8957 |

TABLE 3-continued

List of peptides recovered after LC-MS/MS of ID2 complexes (Part A)

| Sequence | Mass | Charge | Xcorr |
| --- | --- | --- | --- |
| NQVALNPQNTVFDAK | 1658.84967 | 2 | 4.8117 |
| NQVALNPQNTVFDAK | 1658.84967 | 2 | 4.3831 |
| NQVALNPQNTVFDAK | 1658.84967 | 2 | 4.3501 |
| DAGVIAGLNVLR | 1197.695 | 2 | 4.3183 |
| IINEPTAAAIAYGLDR | 1687.90137 | 3 | 4.3118 |
| AQIHDLVLVGGSTR | 1465.81217 | 2 | 4.3026 |
| AQIHDLVLVGGSTR | 1465.81217 | 2 | 4.1075 |
| DAGVIAGLNVLR | 1197.695 | 2 | 3.9758 |
| IINEPTAAAIAYGLDR | 1687.90137 | 2 | 3.9028 |
| NALESYAFNMK | 1287.60381 | 2 | 3.833 |
| IINEPTAAAIAYGLDR | 1687.90137 | 2 | 3.8205 |
| NALESYAFNMK | 1287.60381 | 2 | 3.8048 |
| IINEPTAAAIAYGLDR | 1687.90137 | 3 | 3.7669 |
| NALESYAFNMK | 1287.60381 | 2 | 3.5327 |
| LVNHFVEEFK | 1261.65755 | 2 | 3.5134 |
| ELEQVCNPIISGLYQGAGGPGPGGFGAQGPK | 3055.47277 | 3 | 3.4706 |
| TTPSYVAFTDTER | 1487.70128 | 2 | 3.3575 |
| FGDPVVQSDMK | 1222.57727 | 2 | 3.3508 |
| FGDPVVQSDMK | 1222.57727 | 2 | 3.3198 |
| CQEVISWLDANTLAEK | 1876.88949 | 2 | 3.3085 |
| DAGVIAGLNVLR | 1197.695 | 2 | 3.2009 |
| TTPSYVAFTDTER | 1487.70128 | 2 | 3.1661 |
| NALESYAFNMK | 1287.60381 | 2 | 3.115 |
| FEELCSDLFR | 1315.57726 | 2 | 3.1043 |
| DAGVIAGLNVLR | 1197.695 | 2 | 3.0286 |
| LLQDFFNGR | 1109.57382 | 2 | 2.9548 |
| LLQDFFNGR | 1109.57382 | 2 | 2.9254 |
| DAGVIAGLNVLR | 1197.695 | 2 | 2.8929 |
| AQIHDLVLVGGSTR | 1465.81217 | 2 | 2.8051 |
| LVNHFVEEFK | 1261.65755 | 3 | 2.7603 |
| FEELCSDLFR | 1315.57726 | 2 | 2.7384 |
| FEELCSDLFR | 1315.57726 | 2 | 2.7031 |
| LVNHFVEEFK | 1261.65755 | 2 | 2.6906 |
| LLQDFFNGR | 1109.57382 | 2 | 2.6833 |
| TTPSYVAFTDTER | 1487.70128 | 2 | 2.6357 |
| LLQDFFNGR | 1109.57382 | 2 | 2.5635 |
| LLQDFFNGR | 1109.57382 | 2 | 2.4999 |
| AFYPEEISSMVLTK | 1614.8084 | 2 | 2.4371 |
| KFGDPVVQSDMK | 1350.67223 | 2 | 2.4285 |
| DAGVIAGLNVLR | 1197.695 | 2 | 2.3538 |
| LLQDFFNGR | 1109.57382 | 2 | 2.3447 |
| IINEPTAAAIAYGLDK | 1659.89522 | 2 | 4.8552 |
| NQVAMNPTNTVFDAK | 1649.79519 | 2 | 4.4803 |
| SENVQDLLLLDVTPLSLGIETAGGVMTVLIK | 3238.78549 | 3 | 4.0671 |
| FDDAVVQSDMK | 1254.56709 | 2 | 3.8255 |
| RFDDAVVQSDMK | 1410.6682 | 2 | 3.7114 |
| IINEPTAAAIAYGLDK | 1659.89522 | 2 | 3.6598 |
| NQVAMNPTNTVFDAK | 1649.79519 | 2 | 3.6068 |
| FDDAVVQSDMK | 1254.56709 | 2 | 3.5128 |
| IINEPTAAAIAYGLDK | 1659.89522 | 2 | 3.4404 |
| TVTNAVVTVPAYFNDSQR | 1981.9978 | 2 | 3.3165 |
| DAGTIAGLNVLR | 1199.67427 | 2 | 3.2788 |
| NQVAMNPTNTVFDAK | 1649.79519 | 2 | 3.2252 |
| TVTNAVVTVPAYFNDSQR | 1981.9978 | 3 | 3.1446 |
| TVTNAVVTVPAYFNDSQR | 1981.9978 | 3 | 2.9947 |
| SFYPEEVSSMVLTK | 1616.78767 | 2 | 2.9937 |
| SQIHDIVLVGGSTR | 1481.8071 | 2 | 2.8961 |
| SQIHDIVLVGGSTR | 1481.8071 | 2 | 2.8895 |
| TVTNAVVTVPAYFNDSQR | 1981.9978 | 2 | 2.6701 |
| SQIHDIVLVGGSTR | 1481.8071 | 3 | 2.549 |
| RFDDAVVQSDMK | 1410.6682 | 3 | 2.327 |
| ELEEIVQPLISK | 1397.78864 | 2 | 3.0181 |
| ELEEIVQPLISK | 1397.78864 | 2 | 2.8524 |
| SDGALLLGASSLSGR | 1403.74894 | 2 | 5.0384 |
| SDGALLLGASSLSGR | 1403.74894 | 2 | 3.782 |
| SDGALLLGASSLSGR | 1403.74894 | 2 | 3.7192 |
| SDGALLLGASSLSGR | 1403.74894 | 2 | 3.7112 |
| SDGALLLGASSLSGR | 1403.74894 | 2 | 3.699 |
| SDGALLLGASSLSGR | 1403.74894 | 2 | 3.6308 |
| DSVFLSCSEDNR | 1428.58456 | 2 | 3.3025 |
| DSVFLSCSEDNR | 1428.58456 | 2 | 3.203 |
| EWNLPPNAPACMER | 1684.73556 | 2 | 3.1604 |
| AGADTHGRLLQGNICNDAVTK | 2211.07204 | 3 | 2.6795 |
| AAILPTSIFLTNK | 1388.81479 | 2 | 4.2286 |

TABLE 3-continued

List of peptides recovered after LC-MS/MS of ID2 complexes (Part A)

| Sequence | Mass | Charge | Xcorr |
|---|---|---|---|
| VPEEEKDTNVQVLMVLGAGR | 2184.1329 | 3 | 3.8451 |
| AAILPTSIFLTNK | 1388.81479 | 2 | 3.6058 |
| DDIIENAPTTHTEEYSGEEK | 2277.99938 | 2 | 3.5973 |
| VPLVAPEDLR | 1108.63609 | 2 | 3.1922 |
| VPLVAPEDLR | 1108.63609 | 2 | 3.1217 |
| DDGVSIPGEYTSFLAPISSSK | 2170.05508 | 2 | 3.0351 |
| DLNCVPEIADTLGAVAK | 1785.88367 | 2 | 2.9999 |
| DDIIENAPTTHTEEYSGEEK | 2277.99938 | 3 | 2.9205 |
| DWNTLIVGK | 1045.56768 | 2 | 2.8511 |
| DDGVSIPGEYTSFLAPISSSK | 2170.05508 | 2 | 2.5935 |
| DLNCVPEIADTLGAVAK | 1785.88367 | 2 | 2.5718 |
| DWNTLIVGK | 1045.56768 | 2 | 2.5542 |
| AVFVDLEPTVIDEVR | 1701.90578 | 2 | 5.3909 |
| SIQFVDWCPTGFK | 1584.73008 | 2 | 4.044 |
| AVFVDLEPTVIDEVR | 1701.90578 | 2 | 3.9632 |
| SIQFVDWCPTGFK | 1584.73008 | 2 | 3.8282 |
| SIQFVDWCPTGFK | 1584.73008 | 2 | 3.6667 |
| AVFVDLEPTVIDEVR | 1701.90578 | 2 | 3.2257 |
| SIQFVDWCPTGFK | 1584.73008 | 2 | 3.1661 |
| EIIDLVLDR | 1085.6201 | 2 | 3.1445 |
| DYEEVGVDSVEGEGEEEGEEY | 2348.90488 | 2 | 3.118 |
| EIIDLVLDR | 1085.6201 | 2 | 2.6184 |
| EIIDLVLDR | 1085.6201 | 2 | 2.5862 |
| MAVTFIGNSTAIQELFK | 1869.97791 | 2 | 4.9472 |
| ALTVPELTQQVFDAK | 1659.89522 | 2 | 4.0127 |
| ISVYYNEATGGK | 1301.63723 | 2 | 3.1793 |
| EIVHIQAGQCGNQIGAK | 1822.90139 | 3 | 2.9661 |
| ISVYYNEATGGK | 1301.63723 | 2 | 2.8298 |
| EIVHIQAGQCGNQIGAK | 1822.90139 | 3 | 2.7309 |
| ISVYYNEATGGK | 1301.63723 | 2 | 2.6835 |
| STNGDTFLGGEDFDQALLR | 2055.96181 | 2 | 3.4221 |
| TTPSVVAFTADGER | 1450.71727 | 2 | 2.3736 |
| STNGDTFLGGEDFDQALLR | 2055.96181 | 2 | 2.3339 |
| NLNHSLPSDFTFQNMNSK | 2093.97095 | 3 | 4.0124 |
| LSDFGLCTGLK | 1210.59219 | 2 | 3.4797 |
| LSDFGLCTGLK | 1210.59219 | 2 | 3.4651 |
| NLNHSLPSDFTFQNMNSK | 2093.97095 | 3 | 3.2553 |
| LSDFGLCTGLK | 1210.59219 | 2 | 3.1808 |
| LGLEDFESLK | 1150.59905 | 2 | 3.1727 |
| DIKPDNLLLDSK | 1370.75259 | 2 | 2.9033 |
| IGAPGVEEIK | 1012.56734 | 2 | 2.9011 |
| DIKPDNLLLDSK | 1370.75259 | 2 | 2.9005 |
| LSDFGLCTGLK | 1210.59219 | 2 | 2.7732 |
| LGLEDFESLK | 1150.59905 | 2 | 2.7373 |
| IGAPGVEEIK | 1012.56734 | 2 | 2.7156 |
| ETLTFPPEVPISEK | 1586.83123 | 2 | 2.5835 |
| DIKPDNLLLDSK | 1370.75259 | 2 | 2.5795 |
| LGLEDFESLK | 1150.59905 | 1 | 2.5413 |
| DIKPDNLLLDSK | 1370.75259 | 3 | 2.5234 |
| ETLTFPPEVPISEK | 1586.83123 | 2 | 2.4752 |
| LGLEDFESLK | 1150.59905 | 2 | 2.4312 |
| ETLTFPPEVPISEK | 1586.83123 | 2 | 2.3168 |
| EFDEDVYNHKTPESNIKMK | 2324.08636 | 3 | 2.6751 |
| EFDEDVYNHKTPESNIKMK | 2324.08636 | 3 | 2.4225 |
| EFDEDVYNHKTPESNIKMK | 2324.08636 | 3 | 2.3366 |
| AMLSGPGQFAENETNEVNFR | 2211.01353 | 2 | 2.5405 |
| AMLSGPGQFAENETNEVNFR | 2211.01353 | 2 | 2.3213 |

TABLE 3

List of peptides recovered after LC-MS/MS of ID2 complexes (Part B)

Description

IPI:IPI00002965.2|SWISS-
PROT:P34931|REFSEQ_NP:NP_005518|REFSEQ_XP:XP_166348; XP
IPI:IPI00002965.2|SWISS-
PROT:P34931|REFSEQ_NP:NP_005518|REFSEQ_XP:XP_166348; XP
IPI:IPI00002965.2|SWISS-
PROT:P34931|REFSEQ_NP:NP_005518|REFSEQ_XP:XP_166348; XP
IPI:IPI00002965.2|SWISS-
PROT:P34931|REFSEQ_NP:NP_005518|REFSEQ_XP:XP_166348; XP

TABLE 3-continued

List of peptides recovered after LC-MS/MS of ID2 complexes (Part B)

Description

IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003362.1|SWISS-
PROT:P11021|REFSEQ_NP:NP_005338|TREMBL:Q9UK02|ENSEMBL:
IPI:IPI00003865.1|SWISS-
PROT:P11142|REFSEQ_NP:NP_006588|TREMBL:Q96IS6; Q96H53; Q
IPI:IPI00003865.1|SWISS-
PROT:P11142|REFSEQ_NP:NP_006588|TREMBL:Q96IS6; Q96H53; Q
IPI:IPI00003865.1|SWISS-
PROT:P11142|REFSEQ_NP:NP_006588|TREMBL:Q96IS6; Q96H53; Q
IPI:IPI00003865.1|SWISS-
PROT:P11142|REFSEQ_NP:NP_006588|TREMBL:Q96IS6; Q96H53; Q
IPI:IPI00003865.1|SWISS-
PROT:P11142|REFSEQ_NP:NP_006588|TREMBL:Q96IS6; Q96H53; Q
IPI:IPI00003865.1|SWISS-
PROT:P11142|REFSEQ_NP:NP_006588|TREMBL:Q96IS6; Q96H53; Q
IPI:IPI00007343.1|SWISS-
PROT:O15541|REFSEQ_NP:NP_008909|ENSEMBL:ENSP0000024541
IPI:IPI00007343.1|SWISS-
PROT:O15541|REFSEQ_NP:NP_008909|ENSEMBL:ENSP0000024541
IPI:IPI00007343.1|SWISS-
PROT:O15541|REFSEQ_NP:NP_008909|ENSEMBL:ENSP0000024541
IPI:IPI00007343.1|SWISS-
PROT:O15541|REFSEQ_NP:NP_008909|ENSEMBL:ENSP0000024541
IPI:IPI00007343.1|SWISS-
PROT:O15541|REFSEQ_NP:NP_008909|ENSEMBL:ENSP0000024541
IPI:IPI00007343.1|SWISS-
PROT:O15541|REFSEQ_NP:NP_008909|ENSEMBL:ENSP0000024541
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T

TABLE 3-continued

List of peptides recovered after LC-MS/MS of ID2 complexes (Part B)
Description

IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00007752.1|SWISS-
PROT:P05217|REFSEQ_NP:NP_006079|TREMBL:Q96HX0; Q9BUU9 T
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00012966.1|SWISS-
PROT:Q99081|REFSEQ_NP:NP_003196|TREMBL:Q9NQY7; Q9NQY1; Q
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN

TABLE 3-continued

List of peptides recovered after LC-MS/MS of ID2 complexes (Part B)

Description

IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00013929.1|SWISS-
PROT:P15923|REFSEQ_NP:NP_003191|REFSEQ_XP:XP_209195|EN
IPI:IPI00014424.1|SWISS-
PROT:Q05639|REFSEQ_NP:NP_001949|ENSEMBL:ENSP0000021718
IPI:IPI00014424.1|SWISS-
PROT:Q05639|REFSEQ_NP:NP_001949|ENSEMBL:ENSP0000021718
IPI:IPI00014424.1|SWISS-
PROT:Q05639|REFSEQ_NP:NP_001949|ENSEMBL:ENSP0000021718
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409

TABLE 3-continued

List of peptides recovered after LC-MS/MS of ID2 complexes (Part B)

Description

IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00025399.1|SWISS-
PROT:Q02363|REFSEQ_NP:NP_002157|ENSEMBL:ENSP0000023409
IPI:IPI00027251.1|REFSEQ_NP:NP_009202|TREMBL:Q15208; Q9UPD3|ENSEMBL:E
NSP0000032
IPI:IPI00027251.1|REFSEQ_NP:NP_009202|TREMBL:Q15208; Q9UPD3|ENSEMBL:E
NSP0000032
IPI:IPI00027251.1|REFSEQ_NP:NP_009202|TREMBL:Q15208; Q9UPD3|ENSEMBL:E
NSP0000032
IPI:IPI00027251.1|REFSEQ_NP:NP_009202|TREMBL:Q15208; Q9UPD3|ENSEMBL:E
NSP0000032
IPI:IPI00027251.1|REFSEQ_NP:NP_009202|TREMBL:Q15208; Q9UPD3|ENSEMBL:E
NSP0000032
IPI:IPI00027251.1|REFSEQ_NP:NP_009202|TREMBL:Q15208; Q9UPD3|ENSEMBL:E
NSP0000032
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat
IPI:IPI00033946.1|REFSEQ_NP:NP_005337|ENSEMBL:ENSP00000211738
Tax_Id = 9606 heat TABLE 3-continued List of peptides recovered after LC-MS/MS of ID2 complexes (Part B)

Description

IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00033946.1|REFSEQ_NP:NP_005337|ENSEMBL:ENSP00000211738 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat
IPI:IPI00037070.1|REFSEQ_NP:NP_694881|ENSEMBL:ENSP00000278904 Tax_Id = 9606 heat

TABLE 3-continued

List of peptides recovered after LC-MS/MS of ID2 complexes (Part B)

Description

IPI:IPI00058182.3|ENSEMBL:ENSP00000304307 Tax_Id = 9606
IPI:IPI00058182.3|ENSEMBL:ENSP00000304307 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00104397.1|ENSEMBL:ENSP00000294856 Tax_Id = 9606
IPI:IPI00105804.2|ENSEMBL:ENSP00000298831 Tax_Id = 9606
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00107521.1|REFSEQ_NP:NP_006100|TREMBL:Q9UKH1|ENSEMBL:ENSP00000216350 Ta
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142632.1|SWISS-PROT:P05209|ENSEMBL:ENSP00000323079
Tax_Id = 9606 Tubuli
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00142634.1|SWISS-
PROT:P05218|TREMBL:Q96B85|REFSEQ_XP:XP_212565|ENSEMBL:
IPI:IPI00180885.1|ENSEMBL:ENSP00000322820 Tax_Id = 9606
IPI:IPI00180885.1|ENSEMBL:ENSP00000322820 Tax_Id = 9606
IPI:IPI00180885.1|ENSEMBL:ENSP00000322820 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606

TABLE 3-continued

List of peptides recovered after LC-MS/MS of ID2 complexes (Part B)
Description

IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00182362.1|ENSEMBL:ENSP00000229812 Tax_Id = 9606
IPI:IPI00183173.1|ENSEMBL:ENSP00000298937 Tax_Id = 9606
IPI:IPI00183173.1|ENSEMBL:ENSP00000298937 Tax_Id = 9606
IPI:IPI00183173.1|ENSEMBL:ENSP00000298937 Tax_Id = 9606
IPI:IPI00183645.1|REFSEQ_NP:NP_005639|TREMBL:Q15369|ENSEMBL:ENSP00000284811; EN
IPI:IPI00183645.1|REFSEQ_NP:NP_005639|TREMBL:Q15369|ENSEMBL:ENSP00000284811; EN

TABLE 3

List of peptides recovered after LC-MS/MS of ID2 complexes (Part C)

| Protein | Blank | Blank |
| --- | --- | --- |
| heat shock 70 kDa protein 1-like | HSPA1L, HSP 84 | NP_005518 |
| heat shock 70 kDa protein 1-like | | |
| heat shock 70 kDa protein 1-like | | |
| heat shock 70 kDa protein 1-like | | |
| 78 kDa glucose-regulated protein precursor | HSPA5, GRP-78 | NP_005338 |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| 78 kDa glucose-regulated protein precursor | | |
| heat shock cognate 71 kDa protein isoform 1 | HSPA8, LAP-1 | NP_006588 |
| heat shock cognate 71 kDa protein isoform 1 | | |
| heat shock cognate 71 kDa protein isoform 1 | | |
| heat shock cognate 71 kDa protein isoform 1 | | |
| heat shock cognate 71 kDa protein isoform 1 | | |
| heat shock cognate 71 kDa protein isoform 1 | | |
| RING finger protein 113A | RNF113A | NP_008909 |
| RING finger protein 113A | | |
| RING finger protein 113A | | |
| RING finger protein 113A | | |
| RING finger protein 113A | | |
| RING finger protein 113A | | |
| tubulin beta-4B chain | TUBB4B | NP_006079 |
| tubulin beta-4B chain | | |
| tubulin beta-4B chain | | |
| tubulin beta-4B chain | | |
| tubulin beta-4B chain | | |
| tubulin beta-4B chain | | |
| tubulin beta-4B chain | | |
| tubulin beta-4B chain | | |
| tubulin beta-4B chain | | |
| tubulin beta-4B chain | | |
| transcription factor 12 isoform b | TCF-12, bHLHb20 | NP_003196 |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| transcription factor 12 isoform b | | |
| Transcription factor E2-alpha | TCF3 | NP_003191 |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |
| Transcription factor E2-alpha | | |

TABLE 3-continued

List of peptides recovered after LC-MS/MS of ID2 complexes (Part C)

| Protein | Blank | Blank |
|---|---|---|
| Elongation factor 1-alpha 2 | EEF1A2 | NP_001949 |
| Elongation factor 1-alpha 2 | EEF1A2 | |
| Elongation factor 1-alpha 2 | EEF1A2 | |
| DNA-binding protein inhibitor ID-2 | ID2 | NP_002157 |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| DNA-binding protein inhibitor ID-2 | ID2 | |
| Serine/threonine-protein kinase 38 | STK38 | NP_009202 |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Heat shock 70 kDa protein 1A/1B | HSPA1A | NP_005337 |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock 70 kDa protein 1A/1B | HSPA1A | |
| Heat shock cognate 71 kDa protein | HSPA8, LAP-1 | NP_694881 |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| Heat shock cognate 71 kDa protein | HSPA8, LAP-1 | |
| 78 kDa glucose-regulated protein | HSPA5, GRP-78 | NP_005338 |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| 78 kDa glucose-regulated protein | HSPA5, GRP-78 | |
| Protein arginine N-methyltransferase 5 | PRMT5 | NP_006100 |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Protein arginine N-methyltransferase 5 | PRMT5 | |
| Tubulin alpha-1B chain | TUBA1B | TUBA1B |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin alpha-1B chain | TUBA1B | |
| Tubulin beta chain | TUBB | TUBB |
| Tubulin beta chain | TUBB | |
| Tubulin beta chain | TUBB | |
| Tubulin beta chain | TUBB | |
| Tubulin beta chain | TUBB | |

TABLE 3-continued

List of peptides recovered after LC-MS/MS of ID2 complexes (Part C)

| Protein | Blank | Blank |
|---|---|---|
| Tubulin beta chain | TUBB | |
| Tubulin beta chain | TUBB | |
| GR75_HUMAN Stress-70 protein | HSPA9 | P38646 |
| GR75_HUMAN Stress-70 protein | HSPA9 | |
| GR75_HUMAN Stress-70 protein | HSPA9 | |
| Serine/threonine-protein kinase 38 | STK38 | Q15208 |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Serine/threonine-protein kinase 38 | STK38 | |
| Elongator complex protein 4 | C11orf19, PAXNEB | Q96EB1 |
| Elongator complex protein 4 | C11orf19, PAXNEB | |
| Elongator complex protein 4 | C11orf19, PAXNEB | |
| Transcription elongation factor B polypeptide 1 | TCEB1, Elongin-C | NP_005639 |
| Transcription elongation factor B polypeptide 1 | TCEB1, Elongin-C | |

TABLE 3

List of peptides recovered after LC-MS/MS of ID2 complexes (Part D)

| Blank | Ave SC | Max SC | Num of Expt. (found) | Calculated score [(#peptide*#xcorr)/ (AveSC*MaxSC* Found# of Expt.) |
|---|---|---|---|---|
| HSPA1L | 22.6 | 189 | 389 | 7.39419E−06 |
| HSPA5 | 16.9 | 112 | 360 | 0.000130674 |
| HSPA8 | 39.2 | 332 | 396 | 3.80977E−06 |
| RNF113A | 2.1 | 5 | 7 | 0.212489796 |
| TUBB4B | 29.9 | 310 | 376 | 1.79237E−05 |
| TCF12 | 1.2 | 2 | 6 | 7.705479167 |
| TCF3 | 1 | 1 | 3 | 23.7636 |
| EEF1A2 | 13.4 | 175 | 343 | 1.1763E−05 |
| ID2 | | | | |
| STK38 | 41.1 | 381 | 168 | 9.42036E−06 |
| HSPA1B | 42.9 | 331 | 395 | 4.50311E−05 |

TABLE 3-continued

List of peptides recovered after LC-MS/MS of ID2 complexes (Part D)

| Blank | Ave SC | Max SC | Num of Expt. (found) | Calculated score [(#peptide*#xcorr)/ (AveSC*MaxSC* Found# of Expt.) |
|---|---|---|---|---|
| HSPA8 | 39.2 | 332 | 396 | 1.88416E−05 |
| HSPA5 | 16.9 | 112 | 360 | 5.31505E−05 |
| PRMT5 | 156.6 | 2950 | 175 | 6.79967E−07 |
| TUBA1B | 38.9 | 314 | 389 | 1.24803E−05 |
| TUBB | 37.5 | 338 | 382 | 7.15231E−06 |
| HSPA9 | 19 | 160 | 307 | 1.10002E−05 |
| STK38 | 41.1 | 381 | 168 | 2.89789E−05 |
| ELP4 | 5.3 | 16 | 22 | 0.004301726 |
| TCEB1 | 1.5 | 4 | 46 | 0.01840942 |

TABLE 4

List of ID2-associated proteins ranked by the CRAPome specificity score (Part A)

| Sequence | Mass | Charge | Xcorr |
|---|---|---|---|
| TPVDDPMSLLYNMNDCYSK | 2262.95013 | 2 | 5.0806 |
| IEDHLDEAIHVLR | 1559.81764 | 3 | 5.0922 |
| TRPTTLGSSQFSGSGIDER | 1995.97308 | 3 | 4.8243 |
| SAKPVGPEDM*GATAVYELDTEK | 2324.09735 | 2 | 2.603 |
| AMLSGPGQFAENETNEVNFR | 2211.01353 | 2 | 2.5405 |
| EFDEDVYNHKTPESNIKMK | 2324.08636 | 3 | 2.6751 |
| SQIFSTASDNQPTVTIK | 1836.93382 | 2 | 4.9468 |
| ELEEIVQPLISK | 1397.78864 | 2 | 3.0181 |
| IINEPTAAAIAYGLDR | 1687.90137 | 2 | 5.7404 |
| NLNHSLPSDFTFQNMNSK | 2093.97095 | 3 | 4.0124 |
| IINEPTAAAIAYGLDK | 1659.89522 | 2 | 4.8552 |
| EVDEQMLNVQNK | 1446.68932 | 2 | 4.4619 |
| AVFVDLEPTVIDEVR | 1701.90578 | 2 | 5.3909 |
| IGGIGTVPVGR | 1025.61022 | 2 | 3.1538 |
| STNGDTFLGGEDFDQALLR | 2055.96181 | 2 | 3.4221 |
| SNSFFEGVDWEHIR | 1722.78709 | 2 | 4.1304 |
| AKIHDIVLVGGSTR | 1465.84856 | 3 | 3.0715 |
| MAVTFIGNSTAIQELFK | 1869.97791 | 2 | 4.9472 |
| NQTAEKEEFEHQQK | 1745.80892 | 3 | 3.2724 |
| AAILPTSIFLTNK | 1388.81479 | 2 | 4.2286 |

TABLE 4

List of ID2-associated proteins ranked by the CRAPome specificity score (Part B)
Description IPI:IPI00025399.1|SWISS-
PROT:Q02363|REFSEQ_NP:NP_002157|ENSEMBL:ENSP0000023409
IPI:IPI00013929.1|SWISS-
PROT:P15923|REFSEQ_NP:NP_003191|REFSEQ_XP:XP_209195|EN
IPI:IPI00012966.1|SWISS-
PROT:Q99081|REFSEQ_NP:NP_003196|TREMBL:Q9NQY7; Q9NQY1; Q
IPI:IPI00007343.1|SWISS-
PROT:O15541|REFSEQ_NP:NP_008909|ENSEMBL:ENSP0000024541
IPI:IPI00183645.1|REFSEQ_NP:NP_005639|TREMBL:Q15369|ENSEMBL:ENSP00000284811; EN
IPI:IPI00183173.1|ENSEMBL:ENSP00000298937 Tax_Id = 9606
IPI:IPI00003362.1|SWISS-
PROT:P11021|REFSEQ_NP:NP_005338|TREMBL:Q9UK02|ENSEMBL:
IPI:IPI00058182.3|ENSEMBL:ENSP00000304307 Tax_Id = 9606
IPI:IPI00033946.1|REFSEQ_NP:NP_005337|ENSEMBL:ENSP00000211738
Tax_Id = 9606 heat
IPI:IPI00182362.1|ENSEMBL:ENSP00000229812 Tax_Id = 9606
IPI:IPI00037070.1|REFSEQ_NP:NP_694881|ENSEMBL:ENSP00000278904
Tax_Id = 9606 heat
IPI:IPI00007752.1|SWISS-
PROT:P05217|REFSEQ_NP:NP_006079|TREMBL:Q96HX0; Q9BUU9 T
IPI:IPI00142632.1|SWISS-PROT:P05209|ENSEMBL:ENSP00000323079
Tax_Id = 9606 Tubuli
IPI:IPI00014424.1|SWISS-
PROT:Q05639|REFSEQ_NP:NP_001949|ENSEMBL:ENSP0000021718
IPI:IPI00180885.1|ENSEMBL:ENSP00000322820 Tax_Id = 9606
IPI:IPI00027251.1|REFSEQ_NP:NP_009202|TREMBL:Q15208; Q9UPD3|ENSEMBL:ENSP0000032
IPI:IPI00002965.2|SWISS-
PROT:P34931|REFSEQ_NP:NP_0055181|REFSEQ_XP:XP_166348; XP
IPI:IPI00142634.1|SWISS-
PROT:P05218|TREMBL:Q96B85|REFSEQ_XP:XP_212565|ENSEMBL:
IPI:IPI00003865.1|SWISS-
PROT:P11142|REFSEQ_NP:NP_006588|TREMBL:Q96IS6; Q96H53; Q
IPI:IPI00107521.1|REFSEQ_NP:NP_006100|TREMBL:Q9UKH1|ENSEMBL:ENSP00000216350 Ta

TABLE 4

List of ID2-associated proteins ranked by the CRAPome specificity score (Part C)

| Protein | Blank | Blank | Blank |
|---|---|---|---|
| DNA-binding protein inhibitor ID-2 | ID2 | | NP_002157 |
| Transcription factor E2-alpha | TCF3 | | NP_003191 |
| transcription factor 12 isoform b | TCF-12, bHLHb20 | NP_003196 | |
| RING finger protein 113A | RNF113A | | NP_008909 |
| Transcription elongation factor B polypeptide 1 | TCEB1, Elongin-C | NP_005639 | |
| Elongator complex protein 4 | C11orf19, PAXNEB | Q96EB1 | |
| 78 kDa glucose-regulated protein precursor | HSPA5, GRP-78 | NP_005338 | |
| 78 kDa glucose-regulated protein | HSPA5, GRP-78 | NP_005338 | |
| Heat shock 70 kDa protein 1A/1B | HSPA1A | | NP_005337 |
| Serine/threonine-protein kinase 38 | STK38 | | Q15208 |
| Heat shock cognate 71 kDa protein | HSPA8, LAP-1 | NP_694881 | |
| tubulin beta-4B chain | TUBB4B | | NP_006079 |
| Tubulin alpha-1B chain | TUBA1B | | TUBA1B |
| Elongation factor 1-alpha 2 | EEF1A2 | | NP_001949 |
| GR75_HUMAN Stress-70 protein | HSPA9 | | P38646 |
| Serine/threonine-protein kinase 38 | STK38 | | NP_009202 |
| heat shock 70 kDa protein 1-like | HSPA1L, HSP 84 | NP_005518 | |
| Tubulin beta chain | TUBB | | TUBB |
| heat shock cognate 71 kDa protein isoform 1 | HSPA8, LAP-1 | NP_006588 | |
| Protein arginine N-methyltransferase 5 | PRMT5 | | NP_006100 |

TABLE 4-continued

List of ID2-associated proteins ranked by the CRAPome specificity score (Part D)

| Blank | Ave SC | Max SC | Num of Expt. (found) | Calculated score [(#peptide*#xcorr)/ (AveSC*MaxSC* Found# of Expt.) |
|---|---|---|---|---|
| ID2 | | | | |
| TCF3 | 1 | 1 | 3 | 23.7636 |
| TCF12 | 1.2 | 2 | 6 | 7.70547917 |
| RNF113A | 2.1 | 5 | 7 | 0.2124898 |
| TCEB1 | 1.5 | 4 | 46 | 0.01840942 |
| ELP4 | 5.3 | 16 | 22 | 0.00430173 |
| HSPA5 | 16.9 | 112 | 360 | 0.00013067 |
| HSPA5 | 16.9 | 112 | 360 | 5.3151E−05 |
| HSPA1B | 42.9 | 331 | 395 | 4.5031E−05 |
| STK38 | 41.1 | 381 | 168 | 2.8979E−05 |
| HSPA8 | 39.2 | 332 | 396 | 1.8842E−05 |
| TUBB4B | 29.9 | 310 | 376 | 1.7924E−05 |
| TUBA1B | 38.9 | 314 | 389 | 1.248E−05 |
| EEF1A2 | 13.4 | 175 | 343 | 1.1763E−05 |
| HSPA9 | 19 | 160 | 307 | 1.1E−05 |
| STK38 | 41.1 | 381 | 168 | 9.42E−06 |
| HSPA1L | 22.6 | 189 | 389 | 7.39E−06 |
| TUBB | 37.5 | 338 | 382 | 7.15E−06 |
| HSPA8 | 39.2 | 332 | 396 | 3.81E−06 |
| PRMT5 | 156.6 | 2950 | 175 | 6.80E−07 |

The direct interaction of ID2 with Elongin C and VHL was confirmed in vitro and in vivo (FIG. 10A) showing that recombinant ID2 interacts with elongin C and VHL in a GST pulldown assay (input 10%)), FIG. 9D (showing results of assays in which IMR32 cells were co-transfected with ID2 and Flag-VHL or Flag-HIF1α expression vectors; immunoprecipitation was performed using Flag antibody and immunocomplexes and whole cellular lysates (WCL) were analyzed by western blot using the indicated antibodies) and FIG. 9E (showing results of an assay in which IMR32 cells transfected with Flag-VHL expression vector were used for IgG or ID2 antibody immunoprecipitation Immunocomplexes and WCL were analyzed by western blot; the arrow points to the specific Flag-VHL band; the asterisk indicates IgG light chain)). ID2 was unable to bind to HIFα proteins (FIG. 9D).

VHL and elongin C interacted strongly with ID2, weakly with ID1 and ID3, and did not bind to ID4 (FIG. 10B (presenting co-immunoprecipitation results that demonstrate that VHL preferentially interacts with ID2), FIG. 9F (showing results of Flag immunoprecipitation of binding reactions of in vitro translated Flag-ID and HA-elongin C proteins; immunocomplexes were analyzed by western blot for HA and Flag), and FIG. 9G (showing the results of assay in which Flag-ID proteins and HA-VHL were translated and incubated in vitro; Flag immunocomplexes were analyzed by western blot for HA and Flag)).

The interaction between ID2 and VHL was mediated by the amino-terminal region of ID2 that includes Thr 27 and did not require the HLH domain (amino acids 35-76((FIG. 10C (showing immunoprecipitation and western blot analysis). A more detailed mapping of the regions involved in the VHL-ID2 interaction revealed that amino acids 15-35 of ID2 and the SOCS box of VHL (amino acids 154-174) were required for the binding (FIG. 10D (showing that the N terminus of GST-ID2 is required for the interaction with in vitro translated HA-VHL) and FIG. 10E (showing that amino acids 154-174 of in vitro translated HA-VHL mediate interaction with GST-ID2 (input 10%)).

Lys 159 provides the VHL contact surface for binding to Cul2 as described in Kershaw, N. J. & Babon, J. J. VHL: cullin-g the hypoxic response. Structure 23, 435-436 (2015). The K159E mutation impaired the interaction with ID2 (FIG. 10E). Consistent with ID2 deletion mapping analysis, an ID2 peptide composed of amino acids 14-34 bound to both VHL and components of the VCB complex pre-assembled in insect cells. However, addition of a phosphate to Thr 27 or mutation of Thr 27 to a bulky hydrophobic amino acid (T27W) prevented the binding to both VHL and the VCB complex (FIG. 10F (showing that phosphorylation of ID2 Thr 27 or the ID2(T27W) mutation disrupt the ID2-VHL interaction as analysed by in vitro streptavidin pull down of biotinylated ID2 peptides in the presence of recombinant VCB-Cul2) and FIG. 9H (showing the results of an in vitro streptavidin pulldown assay of biotinylated ID2 peptides (amino acid 14-34 WT, pT27, and T27W) and in vitro translated HA-VHL; bound polypeptides were detected by western blot)).

Figure 11A:
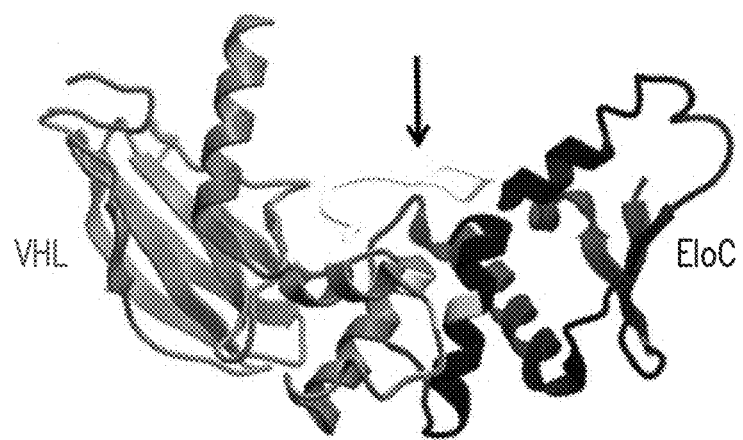
FIG. 11A-11D show the effects of molecular docking of an ID2 (15-31) peptide on the VHL-Elongin C complex.

These findings were corroborated by computational molecular docking whereby a N-terminally-derived ID2 peptide (amino acids 15-31) docked preferentially to a groove on the molecular surface of VHL:Elongin C with the N-terminal half of its interaction surface contacting the SOCS box of VHL that binds Cul2 (primarily Lys 159) and the C-terminal half (including Thr 27) fitting snugly into a hydrophobic pocket mostly contributed by the elongin C surface (FIG. 11A (showing a ribbon representation of the backbone of the VHL-Elongin C complex and the predicted binding conformation of the ID2 peptide. VHL (red ribbon), Elongin C (blue ribbon) and the docked ID2 peptide (purple ribbon); Cul2 contact residues are colored yellow ribbon in both VHL and Elongin C; the arrow indicates the ID2 peptide), FIG. 11C (showing the complex of FIG. 11A rotated 90 degrees around an axis parallel to the page so that the perspective is from the arrow shown in FIG. 11A), and FIG. 11D (showing an .electrostatic molecular surface representation of the VHL-elongin C complex with the docked ID2 peptide; the perspective is the same as in FIG. 11C; the T27 side chain is shown as space-filling spheres and is indicates by the red arrow; the N-terminus and C-terminus of the ID2 peptide are indicated by purple arrows)).

Figure 11B:
Figure 11C:
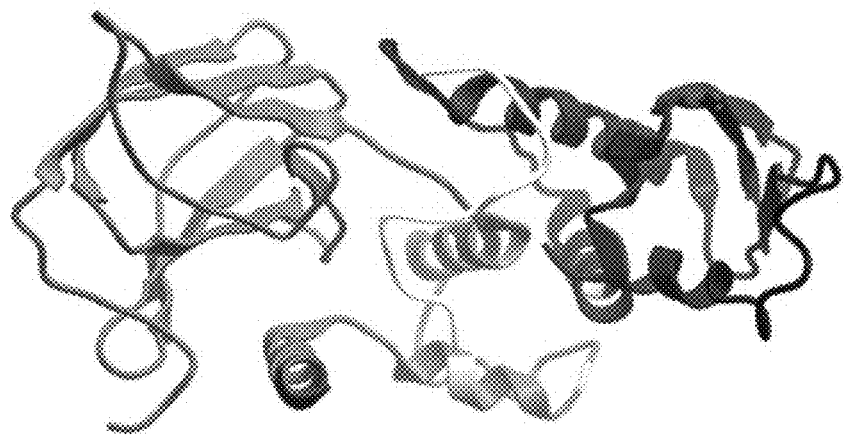
Figure 11D:
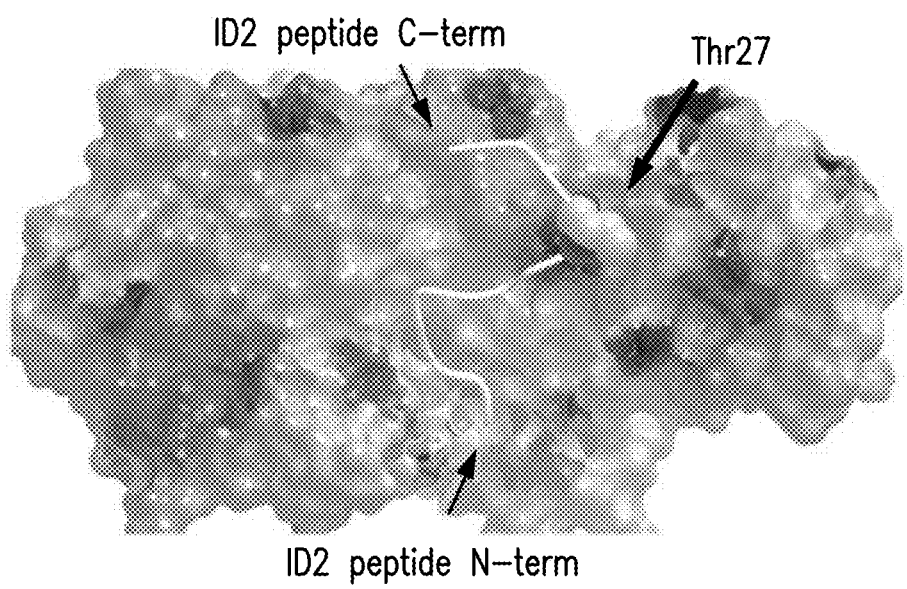

Mutating Thr 27 to phospho-Thr 27 and re-docking resulted in unfavorable energy and displacement of the peptide from this location on the complex (FIG. 11B (showing the docking result for the phospho-Thr-27-ID2 peptide shown from the same perspective as in FIG. 11A)).

DYRK1 disrupted the interaction between VHL and WT ID2 but did not affect the binding of VHL to ID2(T27A) (FIG. 10G (showing co-immunoprecipitation results demonstrating that DYRK1B-mediate phosphorylation of ID2 disrupts ID2 interaction with VHL in vivo)).

Figure 12B:
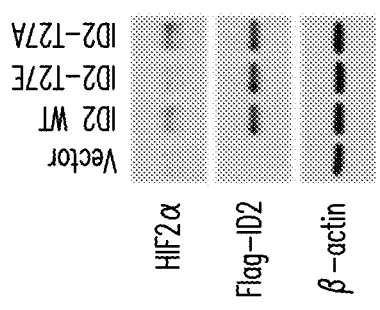
FIG. 12A-12G show the effects of DYRK1-mediated phosphorylation of ID2 on dissociation of the VCB-Cul2 complex.
Figure 12A:
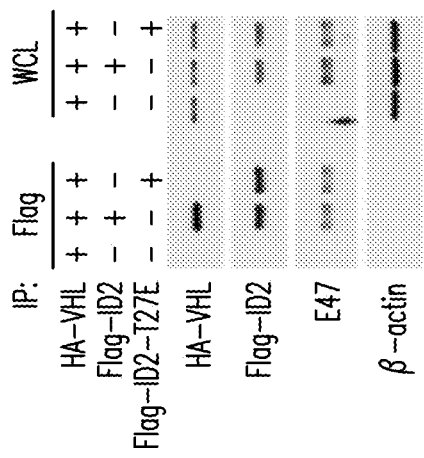

The phosphomimic ID2(T27E) mutant failed to bind VHL and did not promote accumulation of HIF2α (FIG. 12A (showing results of an in vivo binding assay using lysates from U87 cells co-transfected with HA-VHL and Flag-ID2 or Flag-ID2(T27E) expression vectors; flag immunocomplexes were analyzed by western blot using HA and Flag antibodies; whole cell lysates (WCL) were analyzed by western blot using the indicated antibodies; binding of Flag-ID2 and Flag-ID2(T27E) to the bHLH protein E47 is shown as a control for ID2 binding) and FIG. 12B (showing results of assays in which U87 cells were transfected with Flag-ID2, Flag-ID2(T27A) or Flag-ID2(T27E) plasmids; cellular lysates were analyzed by western blot using the indicated antibodies)).

An in vitro assay was performed using purified proteins that included bacterially expressed Flag-ID2, enzymatically active recombinant DYRK1B and baculovirus-expressed VCB-Cul2 complex or purified VHL. In this system, ID2 bound to VCB-Cul2 complex and VHL in the absence of active DYRK1B, but the interaction was disrupted by DYRK1-mediated phosphorylation of Thr 27 (FIG. 10H (showing in vitro phosphorylation of recombinant ID2 by purified DYRK1B blocks ID2 interaction with VHL and elongin C in the reconstituted VCB-Cul2 complex) and FIG. 12C (showing in vitro binding between purified Flag-ID2 an His0VHL following in vitro kinase reaction using recombinant DYRK1B and Flag-ID2)).

In the VCB-Cul2 complex, the Cul2 subunit provides the scaffold module for the interaction with the ubiquitin-conjugating enzyme (E2) as described in Kamura, T. et al. Rbx1, a component of the VHL tumor suppressor complex and SCF ubiquitin ligase. Science 284, 657-661 (1999) and Ohta, T., Michel, J. J., Schottelius, A. J. & Xiong, Y. ROC1, a homolog of APC11, represents a family of cullin partners with an associated ubiquitin ligase activity. Mol. Cell 3, 535-541 (1999). To express ID2(T27A), ID2 was loaded onto VCB, and the Cul2/RBX1 module dissociated from the complex in the absence of changes in the total cellular levels of Cul2 and RBX1 (FIG. 10I (showing that ID2(T27A) displaces Cul2 from VCB complex in a co-immunoprecipitation assay in U87 cells)). Challenging the pre-assembled VCB complex with increasing amounts of recombinant Flag-ID2 resulted in progressive dissociation of Cul2 (FIG. 10J (showing progressive dissociation of Cul2 from recombinant VCB complex by increasing concentration of purified Flag-ID2)).

Figure 12D:
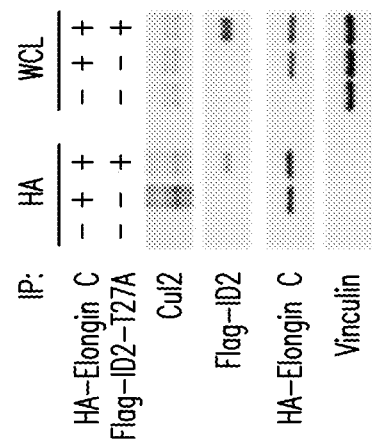
Figure 12C:
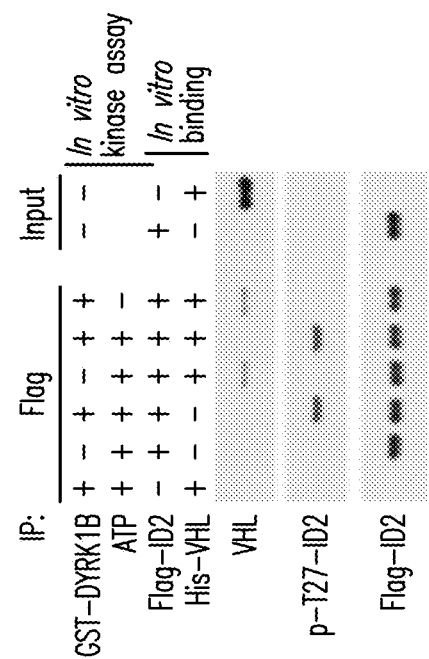
Figure 12G:
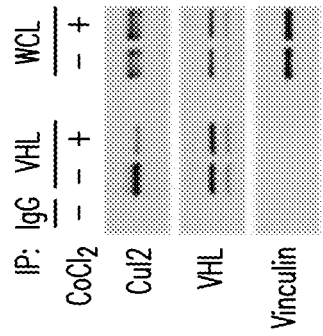
Figure 12E:
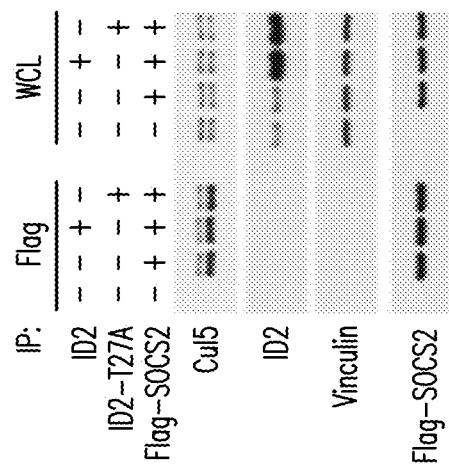

Expression of ID2(T27A) triggered a comparable block of Elongin C-Cul2 association whereas it did not affect the assembly of a Cul5-based complex containing SOCS2, a SOCS protein that cannot bind to ID2(T27A) (FIG. 12D (showing the results of analysis of the HA-Elongin C immunocomplexes in U87 cells transfected with HA-Elongin C in the absence or presence of Flag-ID2 (T27A); anti-HA immunoprecipitation reactions and WCL were analyzed by western blot using antibodies against Cul2, HA (Elongin C), and Flag (ID2) and FIG. 12E (showing analysis of the Flag-SOCS2 immunocomplexes in U87 cells transfected with ID2, ID2(T27A) or the empty vector; flag immunoprecipitation reactions and WCL were analyzed by western blot using antibodies against Cul5, ID2, and Flag (SOCS2)).

Figure 12F:
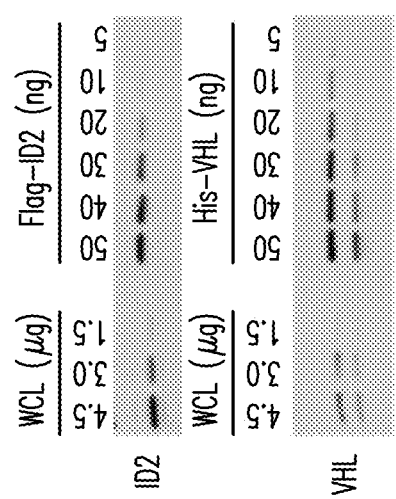

In glioma cells in which ID2 and VHL are present at a molar ratio of 5.7:1 (FIG. 12F (showing stoichiometric analysis of ID2 and VHL in cellular lysates; decreasing amount of WCL from $1\times10^6$ U87 cells and purified proteins were assayed by western blot (left); regression plots of densitometry analysis were used to determine ID2 and VHL protein concentration and the ID2:VHL ratio (right))), hypoxia signalling promoted the association between endogenous VHL and ID2 while dissociating Cul2 (FIG. 10K (showing silencing of ID2 in U87 cells reverts $CoCl_2$-mediated dissociation of Cul2 from VHL as evaluated by Co-IP-WB; data for whole cellular lysates (WCL) is also presented) and FIG. 12G (showing the results of immunoprecipitation of endogenous VHL in U87 cells in the presence and in the absence of $CoCl_2$; Cul2 and VHL are analyzed by western blot; vinculin is shown as loading control)). Silencing of ID2 rescued the dissociation of Cul2 from VCB complex and prevented HIF2α elevation (FIG. 10K). Together, these findings indicate that ID2 activation stabilizes HIF2α by disabling VCB ubiquitin ligase via dissociation of Cul2.

Example 5—A DYRK1-ID2 Pathway Controls HIF2α in Glioma

To determine whether activation of ID2 enhances HIF2α transcriptional activity in an unbiased fashion, CINDy, an algorithm for high-fidelity reconstruction of post-translational causal dependencies was used to interrogate whether ID2 can affect the activity of HIF2α on its targets in the context of GBM. When applied to a collection of 548 TCGA-derived GBM samples, ID2 activity emerged as the modulator of the transcriptional connection between HIF2α and its activated target genes (FIG. 13A (showing significant and positive targets of HIF2α correlate with HIF2α in GBM with high ID2 activity compared to a set of random genes by GSEA) and FIG. 13B (showing correlations are not significant in GMB with low ID2 activity)).

Figure 14A:
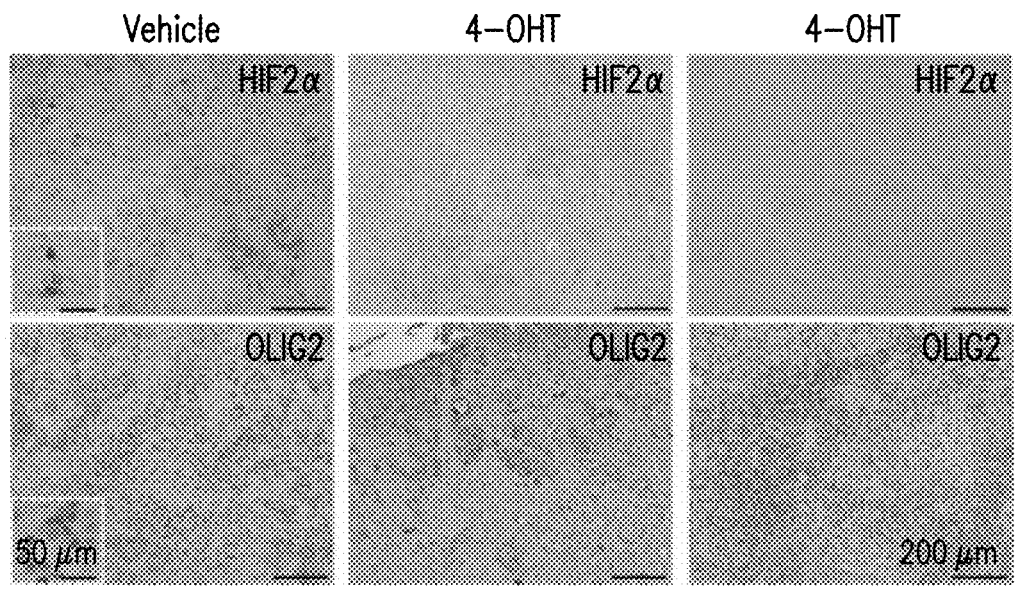
FIG. 14A-14F show the effects of DYRK1 on proliferation of human glioma.

The activity of ID2 was estimated by the VIPER algorithm, a computational tool designed to infer protein activity from gene expression data. When GBM samples were divided into two groups based on ID2 activity, samples with higher ID2 activity showed significantly stronger correlation between HIF2α and its targets than a set of random genes (P=0.001) (FIG. 13A). This positive correlation was absent in the cohort of GBM with low ID2 activity (P=0.093) (FIG. 13B). Consistent with these observations, a marked reduction of HIF2α protein was detected following acute deletion of the Id1 and Id2 genes in a mouse model of malignant glioma (FIG. 14A (showing results from an assay in which malignant glioma were induced in $Id1^{Flox/Flow}$-$Id2^{Flox/Flox}$-$Id2^{-/-}$ mice via injection of lentivirus expressing RAS-V12-IRES-CRE-ER linked to U6-shp53 cassette into the dentate gyrus; mice were treated for 5 days with tamoxifen or vehicle and euthanized 2 days later; tumors were analyzed by immunohistochemistry using HIF2α and OLIG2 antibodies; nuclei were counterstained with haematoxylin)).

Figure 13C:
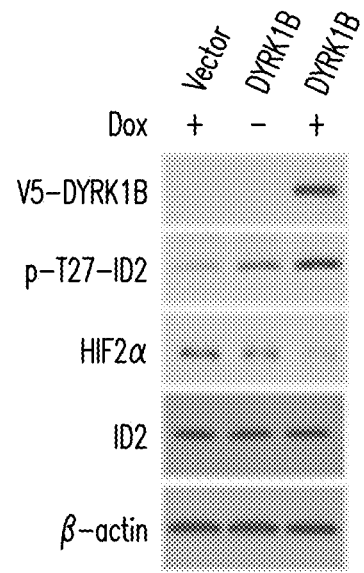
Figure 13D:
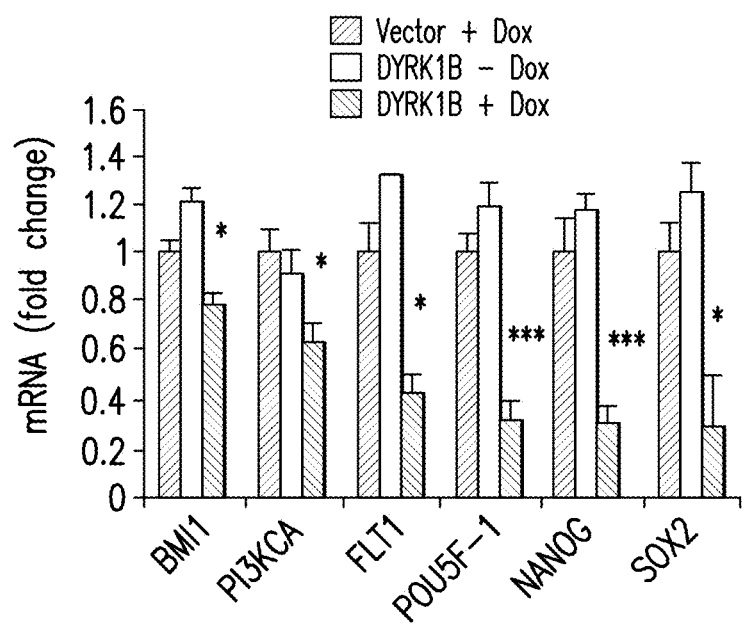

The effects of DYRK1 expression in mouse models of human glioma were also studied. Tetracycline-induced expression of DYRK1B at levels comparable to normal brain (FIG. 14B (showing western blot analysis of DYRK1B in U87 cells stably expressing a doxycycline inducible DYRK1B or the empty vector; cells were treated with 0.75 mg ml$^{-1}$ doxycycline or vehicle for 36 h; lysates of adult mouse cortex (CX) and cerebellum (CB) were used to compare exogenous DYRK1B with endogenous levels of the protein)), downregulated HIF2α in glioma cells in vitro and in sub-cutaneous xenografts and reduced the expression of the HIF2α targets that promote stem cell functions (FIG. 13C (showing inducible expression of DYRK1B in U87 causes ID2 Thr 27 phosphorylation and downregulation of HIF2α), FIG. 13D (showing qRT-PCR from cells treated as in c; n=9 (3 biological replicates performed in triplicates) ±s.d. BMI1: *P=0.0470; PI3KCA: *P=0.0279; FLT1: *P=0.0246; POU5F-1: *P=0.000796344; NANOG: *P=0.000737396; SOX2: *P=0.028884239 (DYRK1B−Dox versus DYRK1B+Dox)), and FIG. 13E (showing that inducible expression of DYRK1B downregulates HIF2α in subcutaneous xenografts of U87 cells as indicated by immunostaining)).

Figure 13E:
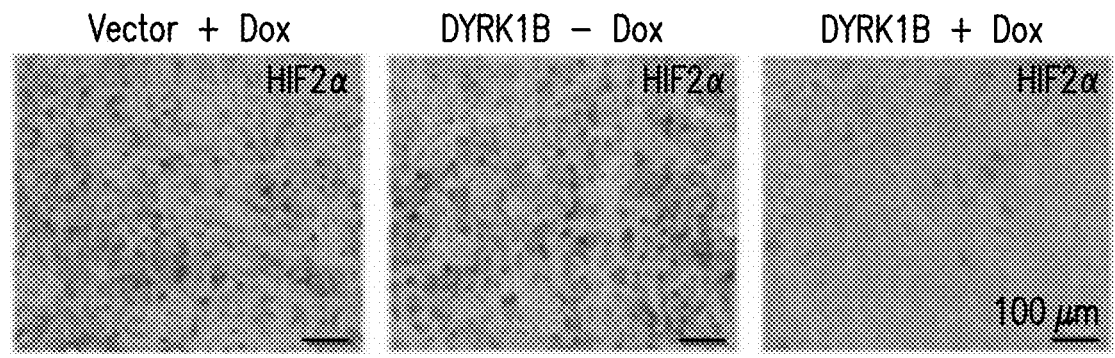
Figure 13F:
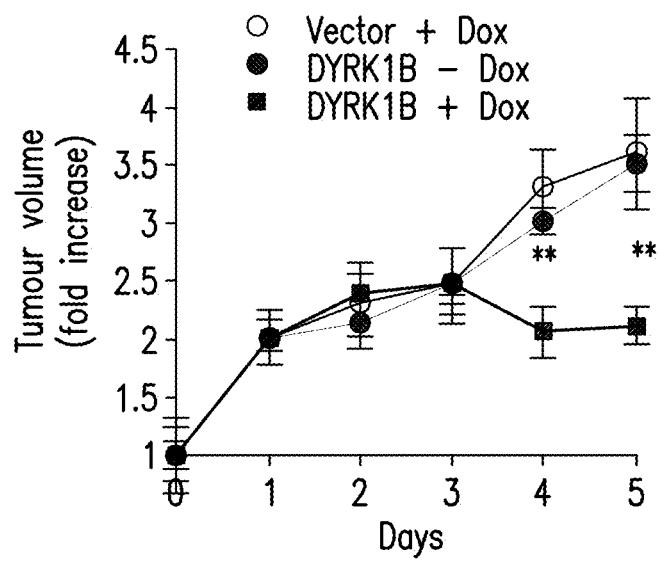
Figure 13G:
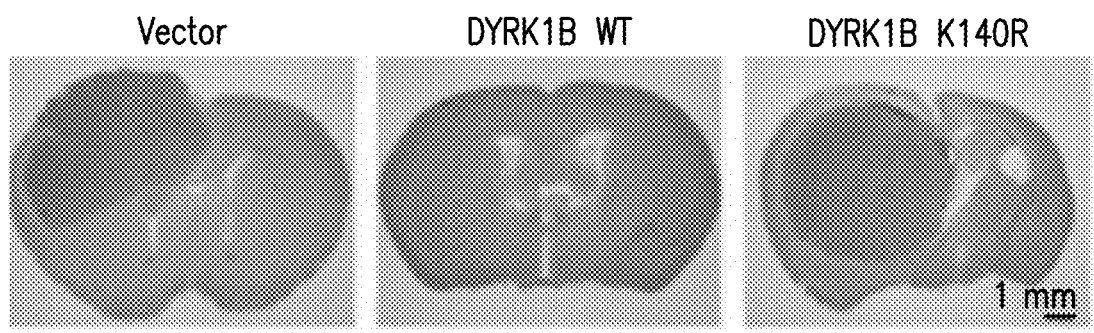
Figure 13H:
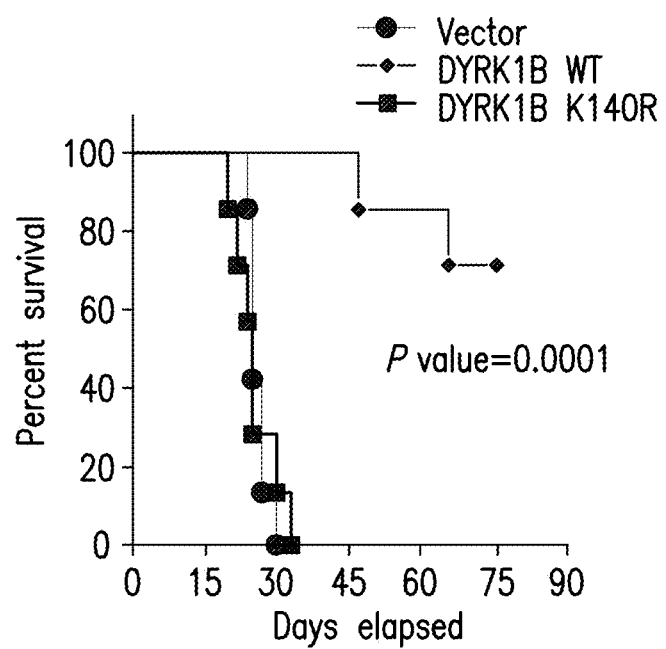

Expression of DYRK1B also inhibited tumor cell proliferation in vivo, resulting in tumor reduction (FIG. 13F (showing that inducible expression of DYRK1B causes tumor growth inhibition in mice treated as in FIG. 13E; doxycycline (Dox) treatment started at day 0 (n=7 mice per group; : P=0.0040 and 0.0069, DYRK1B−Dox versus DYRK1B+Dox at day 4 and day 5, respectively)), and FIG. 14C (showing tissue sections from experiment in FIG. 13E and FIG. 13.F that were analyzed by immunostaining using BrdU antibodies), and FIG. 14D (showing quantification of BrdU positive cells from the experiment in FIG. 14C; data in the histograms represent means±s.d. (n=5; *P=3.065× 10$^7$, DYRK1B−Dox versus DYRK1B+Dox); asterisks indicate statistical significance by two-tailed t-test.)

Figure 14B:
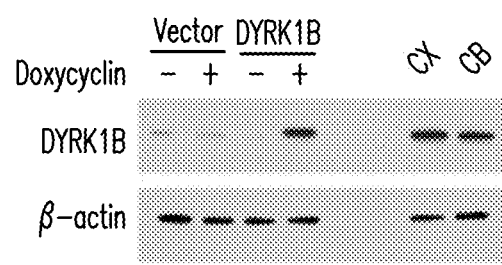
Figure 14C:
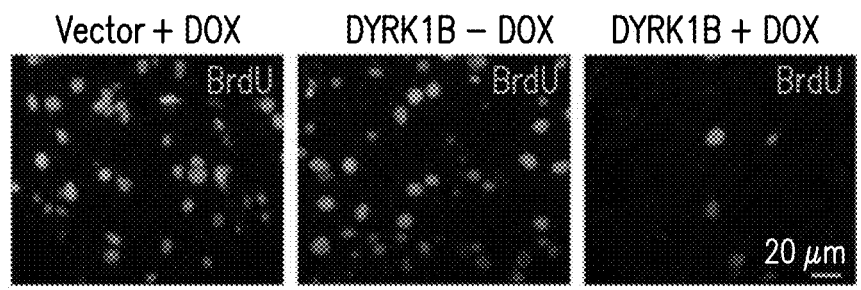
Figure 14D:
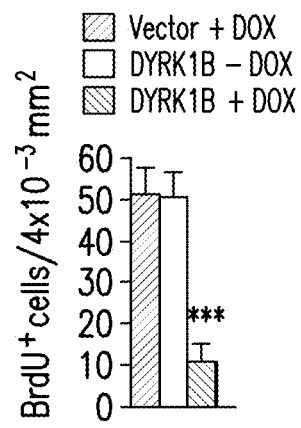
Figure 14E:
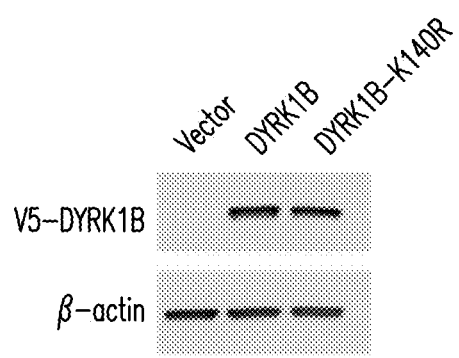

The anti-tumor effects of DYRK1B(WT) or the kinase inactive K140R mutant were evaluated in an orthotopic model of glioma (FIG. 14E (showing western blot analysis of ectopically expressed V5-DYRK1B, V5-DYRK1B-K140R in U87 cells)). Animals bearing glioma cells that expressed DYRK1B(WT) manifested significantly increased survival and tumor latency relative to mice bearing DYRK1B(K140R) or vector transduced cells (FIG. 13G (showing expression of DYRK1B WT but not DYRK1B (K140R) inhibits orthotopic growth of U87 (haematoxylin & eosin staining of brain cross-sections); mice injected with U87-vector or DYRK1B(K140R) were euthanized on day 25; mice injected with U87-DYRK1B were euthanized on day 70) and FIG. 13H (showing a Kaplan-Meier analysis of mice in FIG. 13G (n=7 animals per group))).

Figure 14F:
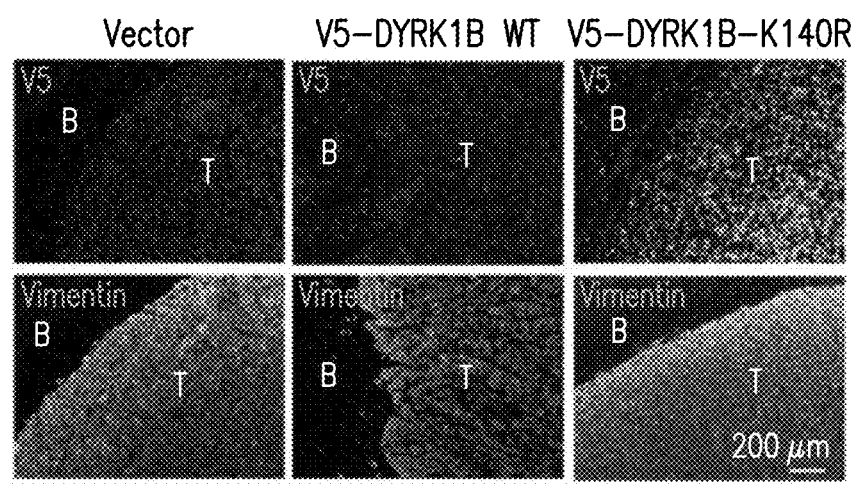

Two out of seven mice in the DYRK1B(WT) group developed tumors that failed to express exogenous DYRK1B (FIG. 14F (showing brain cross-sections of mice intracranially injected with U87 cells in FIG. 14E as analyzed by immunofluorescence using V5 antibody (red, upper panels) to identify exogenous DYRK1B and human vimentin antibody (red, lower panels) to identify human glioma cells; nuclei were counterstained with DAPI (blue). T, tumor; B, brain)). This result suggests that active DYRK1 kinase is incompatible with tumor growth in this glioma model.

Figure 13I:
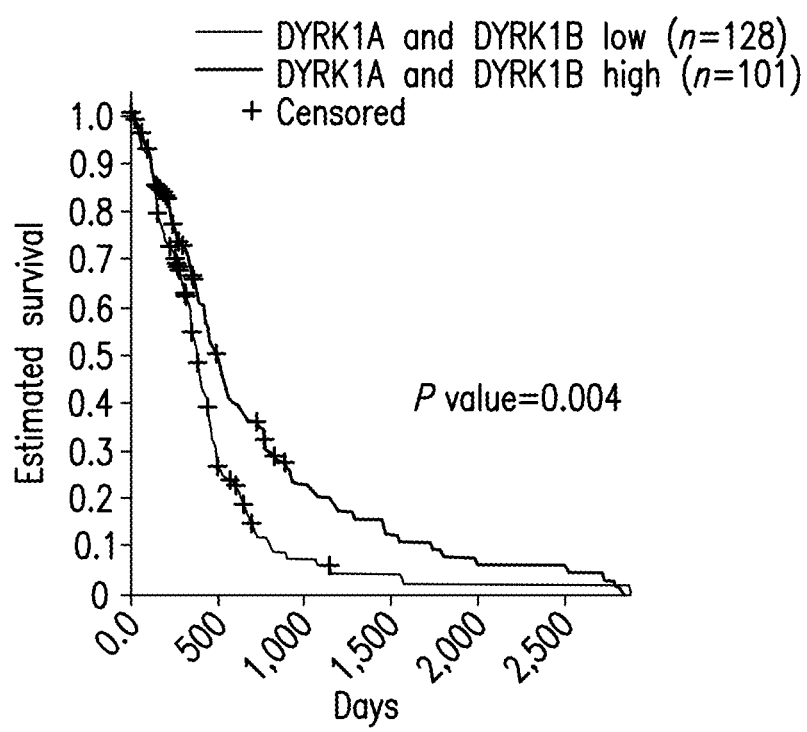
Figure 15A:
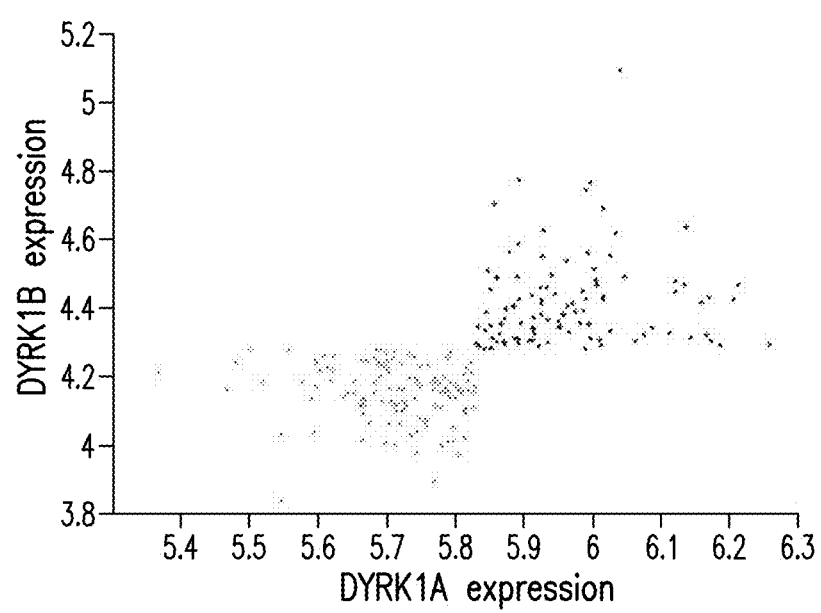
FIG. 15A-15B show analysis of DYRK1 A, DYRK1B and ID2 expression in human GBM.
Figure 15B:
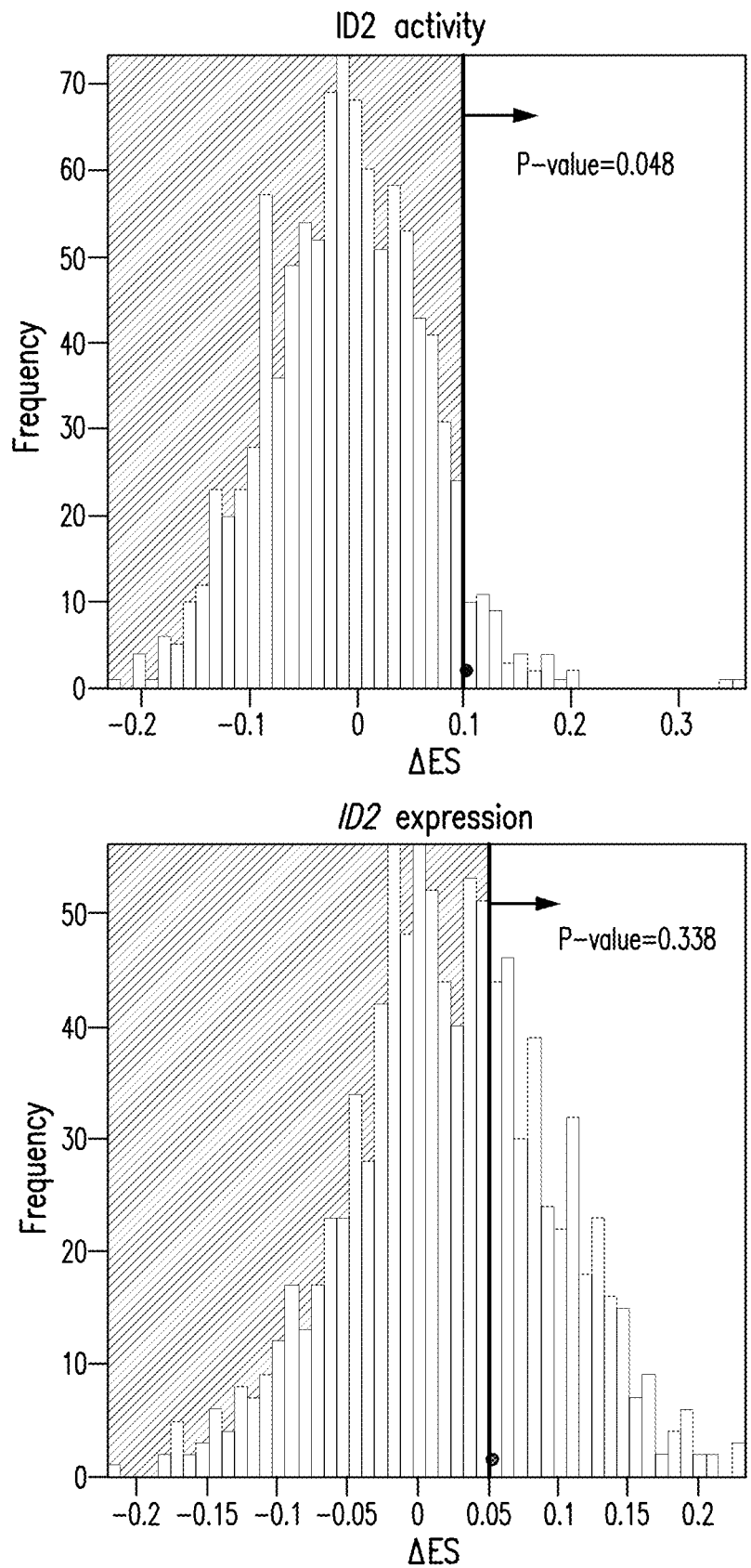

Finally, higher DYRK1A and DYRK1B predicted a more favorable clinical outcome for GBM patients, thus supporting the clinical significance of DYRK1 activity in glioma (FIG. 13I and FIG. 15A (showing scatter plot showing the expression of DYRK1A and DYRK1B in GBM; blue and red dots indicate GBM samples with high or low expression of both DYRK1A and DYRK1B, respectively; GBM samples were used for Kaplan-Meier survival analysis to evaluate the prognostic power of the expression of DYRK1A and DYRK1B shown in FIG. 13I)).

The present disclosure makes mention of various scientific references, which are each incorporated by reference herein.

We claim:

1. A method of treating a cancer or a tumor in a patient, the method comprising: administering to the patient a composition comprising an isolated Dual-Specificity Tyrosine-Phosphorylation-Regulated Protein Kinase 1 (DYRK1) protein in an amount and for a time sufficient to increase degradation of Hypoxia-Inducible Factor-α (HIFα) in cancer cells or tumor cells in the patient and/or to decrease half-life of HIFα in the cancer cells or tumor cells in the patient.

2. The method of claim 1, wherein the HIFα comprises HIF2α.

3. The method of claim 1, wherein the administering increases phosphorylation of Thr 27 of Inhibitor of DNA Binding-2 (ID2) protein in the cancer cells or tumor cells as compared to untreated cancer cells or tumor cells.

4. The method of claim 1, wherein the administering increases dissociation of ID2 from a von-Hippel Lindau (VHL) protein in the cancer cells or tumor cells as compared to untreated cancer cells or tumor cells.

5. The method of claim 1, wherein the administering increases ubiquitylation of the HIFα in the cancer cells or tumor cells as compared to untreated cancer cells or tumor cells.

6. The method of claim 1, wherein the cancer or tumor is a glioma, a retinoblastoma, an ewings sarcoma, or a lymphoma.

7. The method of claim 1, wherein the administering delays or prevents the progression of one or more symptoms of the cancer or the tumor for at least a set period of time, causes a regression of one or more symptoms of the cancer or the tumor for at least a set period of time, and/or causes the disappearance of one or more symptoms of the cancer or the tumor for at least a set period of time.

8. The method of claim 1, wherein the DYRK1 protein is a recombinant DYRK1 protein.

\* \* \* \* \*